(12) United States Patent
Sánchez Reillo et al.

(10) Patent No.: US 8,207,321 B2
(45) Date of Patent: Jun. 26, 2012

(54) METHOD OF OBTAINING IDOLOCARBAZOLES USING BIOSYNTHETIC REBECCAMYCIN GENES

(75) Inventors: César Sánchez Reillo, Oviedo (ES); Alfredo Fernandez Braña, Oviedo (ES); José Antonio Salas Fernandez, Oviedo (ES); Carmen Mendez Fernandez, Oviedo (ES)

(73) Assignee: Universidad De Oviedo, Oviedo (ES)

( * ) Notice: Subject to any disclaimer, the term of this patent is extended or adjusted under 35 U.S.C. 154(b) by 1529 days.

(21) Appl. No.: 10/493,000

(22) PCT Filed: Oct. 17, 2002

(86) PCT No.: PCT/ES02/00492
§ 371 (c)(1),
(2), (4) Date: Feb. 13, 2007

(87) PCT Pub. No.: WO03/033706
PCT Pub. Date: Apr. 24, 2003

(65) Prior Publication Data
US 2008/0004326 A1   Jan. 3, 2008

(30) Foreign Application Priority Data

Oct. 19, 2001 (ES) ....................... 0102312

(51) Int. Cl.
C07H 21/04 (2006.01)
C07H 21/02 (2006.01)
C07H 21/00 (2006.01)
C12P 1/00 (2006.01)
C12N 1/12 (2006.01)
C12N 15/00 (2006.01)

(52) U.S. Cl. ..................... 536/23.2; 536/23.7; 536/25.4; 435/252.1; 435/320.1; 435/41

(58) Field of Classification Search .......................... None
See application file for complete search history.

(56) References Cited

FOREIGN PATENT DOCUMENTS
EP      0 769 555      4/1997

OTHER PUBLICATIONS

Genbank accession No. AB023953, publicly available on May 12, 2000, Retrieved from the Internet <URL: http://www.ncbi.nlm.nih.gov/nuccore/5725108?ordinalpos=1&itool=EntrezSystem2.PEntrez.Sequence.Sequence_ResultsPanel.Sequence_RVDocSum>.*
Taft et al Trends in Genetics 22(12):649-653, 2006.*
Linder, Lab. Anim. 30(5):34-39, 2001.*
Bilbo et al, Lab. Anim. 30(1):24-29, 2001.*
Holschneider et al, Int. J. Dev. Neuroscience 18 :615-618, 2000.*
Wood. Comp. Med. 50(1): 12-15, 2000.*
Sigmund, Arterioscler. Throm. Vasc. Biol. 20:1425-1429, 2000.*
Kappel et al. Current Opinion in Biotechnology 3:558-553 1992.*
Ohuchi et al. (Cloning and expression of a gene encoding N-glycosyltransferase (ngt) from Saccharothrix aerocolonigenes ATCC39243, J. Antibiot. 53 (4), pp: 393-403 (2000), Abstract, Retrieved from the Internet <URL:http://www.ncbi.nlm.nih.gov/pubmed/10866221>).*
Hyun et al. (The Biosynthesis of Indolocarbazoles in a Heterologous E. coli Host, Genbank Accession No. AF534707, publicly available on Aug. 29, 2002, Retrieved from the Internet <URL:http://www.ncbi.nlm.nih.gov/nuccore/22536119>).*
Ohuchi et al. (Cloning and expression of a gene encoding N-glycosyltransferase (ngt) from Saccharothrix aerocolonigenes ATCC39243, J. Antibiot. 53 (4), pp: 393-403 (2000)).*
Ohuchi, T., et al. "Cloning and Expression of a Gene Encoding N-Glycosyltrasferase (NGT) from Saccharothrix aerocolonigenes ATCC39243." The Journal of Antibiotics (2000) vol. 53, No. 4, pp. 393-403.
Sanchez et al., The Biosynthetic Gene Cluster for the Antitumor Rebeccamycin: Characterization and Generation of Indolocarbazole Derivatives; Chemistry and Biology, 9: 519-531, 2002.
Sanchez et al., Combinatorial Biosynthesis of Antitumor Indolocarbazole Compounds, PNAS, 102: 461-466, 2005.

* cited by examiner

Primary Examiner — Suzanne M Noakes
Assistant Examiner — Jae W Lee
(74) Attorney, Agent, or Firm — Ladas & Parry LLP

(57) ABSTRACT

Method for production of indolocarbazoles by using rebeccamycin biosynthetic genes. The invention is based on utilization of rebeccamycin biosynthetic genes from *Saccharothrix aerocolonigenes* for production of indolocarbazoles in related microorganisms (*Streptomyces* spp.). Method includes the isolation of a DNA fragment from *Saccharothrix aerocolonigenes* ATCC39243 containing the rebeccamycin biosynthesis gene cluster and the expression of these genes in *Streptomyces albus*, achieving production of rebeccamycin and derivatives. The invention is suitable for use in the pharmaceutical field.

30 Claims, 14 Drawing Sheets

A

B

US 8,207,321 B2

METHOD OF OBTAINING IDOLOCARBAZOLES USING BIOSYNTHETIC REBECCAMYCIN GENES

FIELD OF THE INVENTION

The invention refers to the pharmaceutical field and particularly to compounds with potential application in oncology, with indolocarbazole chemical structure and obtained by fermentation of transformed microorganisms.

BACKGROUND OF THE INVENTION

Rebeccamycin (FIG. 1, A) is a natural product of *Saccharothrix aerocolonigenes* ATCC39243, a Gram-positive bacterium of the actinomycetes group (Bush et al. *J. Antibiot.* 40: 668-678, 1987). Actinomycetes are natural soil inhabitants with great industrial and biotechnological interest, especially the *Streptomyces* genus, because they are the source of many known bioactive compounds. Many of these compounds have pharmaceutical application due to their antitumor, antibacterial, antifungal, antiparasitic, or immunosupressor activity. Rebeccamycin shows antibacterial activity against Gram-positive bacteria such as *Staphylococcus aureus, Micrococcus luteus* and *Streptococcus faecalis* (Bush et al. *J. Antibiot.* 40: 668-678, 1987). However, its major significance resides in its antitumor activity, demonstrated in vivo against several tumors implanted in mice, and in vitro against several tumor cell lines (Bush et al. *J. Antibiot.* 40: 668-678, 1987). There are currently two rebeccamycin derivatives in clinical trials for their future use as antineoplasic agents (NB-506, NSC655649).

Because of its chemical structure, rebeccamycin belongs to the indolocarbazole family of natural products. Since their discovery in 1977, more than 60 indolocarbazole natural products have been described, which can be classified in three groups containing either an indolo[2,3-a]pyrrolo[3,4-c]carbazole core (e.g. rebeccamycin), an indolo[2,3-a]carbazole core (e.g. tjipanazoles), or a bis-indolylmaleimide core (e.g. arcyriarubin). Due to their novel structures and the wide variety of activities displayed (antimicrobial, antifungal, immunosupressor, antitumor, etc.), this group of alkaloids has attracted great interest. In particular, indolopyrrolocarbazoles constitute a new class of antitumor agents, which can be further classified in two subgroups according to their mechanism of action. One subgroup consists of protein kinase inhibitors (especially protein kinase C inhibitors), and includes staurosporine (FIG. 1, B) and analogs. The second subgroup consists of DNA-damaging agents acting on topoisomerase I or II, but not on protein kinases, and includes rebeccamycin (FIG. 1, A) and analogs. Several indolocarbazoles have already entered clinical trials in the USA, Japan and Europe, including protein kinase inhibitors (UCN-01, CGP41251, CEP-751) and DNA-damaging agents (NB-506, NSC655649) (Akinaga et al. *Anti-Cancer Drug Design* 15: 43-52, 2000).

Nowadays there is a great need for new antitumor agents, with improved activity, lower undesirable secondary effects, and greater selectivity, as compared to drugs currently in use. Traditionally, pharmaceutical companies have developed new drugs by using two major approaches: (1) screening for new natural products, and (2) chemical synthesis and/or modification of specific compounds. These methods are still useful, but they usually need very important inputs of resources (time, money, energy), because analysis of thousands of products is generally required to find a new promising compound. Development of the genetic engineering of microorganisms has set the stage for generation of new bioactive compounds through manipulation of genes involved in biosynthesis of antitumor agents, mainly from actinomycetes. These techniques can also be used to improve present production levels of known natural drugs, as wild type strains usually yield low concentrations of the desired metabolite.

The chemical structures of most indolocarbazole natural products consist of two components: the indolocarbazole aglycon, and one or more sugar moieties. The indolocarbazole aglycon is biosynthesized from two tryptophan molecules, at least in the case of indolopyrrolocarbazoles. The sugar moiety present in rebeccamycin is a 4-O-methyl-β-D-glucose (FIG. 1, A). In the case of staurosporine, the sugar is an L-rhamnose derivative (FIG. 1, B). Recently, some genes involved in biosynthesis of the sugar moieties for the two mentioned indolocarbazoles have been reported:

(1) A chromosomal region of *Streptomyces longisporoflavus* DSM10189 involved in biosynthesis of the staurosporine sugar. This DNA region was able to complement a mutation impairing biosynthesis of the sugar moiety. There are not any reported evidences for the involvement of the mentioned DNA region in biosynthesis of the indolocarbazole aglycon (U.S. Pat. No. 6,210,935).

(2) A gene, called ngt, that codes for the rebeccamycin N-glucosyltransferase of *Saccharothrix aerocolonigenes* ATCC39243, responsible for sugar transfer to the indolocarbazole aglycon (Ohuchi et al. *J. Antibiot.* 53: 393-403, 2000). There are not any reported evidences for the involvement of the identified DNA region in the biosynthesis of the indolocarbazole aglycon. The DNA sequence of the ngt gene has previously been used for bioconversion of indolocarbazole aglycons to D-glucosilated derivatives. The procedure consisted of adding a particular indolocarbazole aglycon (either chemically synthesized or isolated from a producer strain) to the culture broth of a *Streptomyces lividans* strain harboring a plasmid containing the ngt gene, and isolating the glucosylated product from the culture (Ohuchi et al. *J. Antibiot.* 53: 393-403, 2000).

With the mentioned exception of the ngt gene (Ohuchi et al. *J. Antibiot.* 53: 393-403, 2000), there are not any previously reported descriptions of the nucleotide sequence which the present invention refers to. Moreover, there are not any previously reported descriptions of nucleotide sequences involved in biosynthesis of an indolocarbazole aglycon.

It was also known in the prior art (EP 0769555 A1) a gene encoding glycosyltransferase activity derived from *Saccharothrix aerocolonigenes* ATCC39243 strain, recombinant vectors having that gene, host cells transformed with such a vector, a process for preparing glycosyltransferase by culturing such a transformed host cell and a process for preparing glycosylated indolopyrrolocarbazole derivatives by culturing such a transformed host cell and using indolopyrrolocarbazole derivatives as starting compounds.

BRIEF DESCRIPTION OF THE INVENTION

The present invention refers to a method for production of indolocarbazoles by using rebeccamycin biosynthetic genes, which includes the following steps:

(1) Isolation of a chromosomal region from *Saccharothrix aerocolonigenes*, the said chromosomal region containing (among other genes) a gene encoding the rebeccamycin N-glucosyltransferase.

(2) Transfer of the ability to biosynthesize rebeccamycin to a *Streptomyces* spp. microorganism, by introduction of said chromosomal region.

(3) Determination and analysis of the nucleotide sequence of the gene cluster responsible for rebeccamycin biosynthesis.
(4) Expression of certain genes from the mentioned gene cluster in a host organism, in order to produce rebeccamycin-derived indolocarbazoles.

Other aspect of present invention is the use of an indolocarbazole or an indolocarbazole precursor thus obtained in the production of active compositions for the treatment of tumor processes.

Molecular biology techniques used in the present invention are described in Kieser et al. (Practical *Streptomyces* genetics, The John Innes Foundation, Norwich, United Kingdom, 2000) and Sambrook et al. (Molecular cloning: a laboratory manual, Cold Spring Harbor Laboratory Press, Cold Spring Harbor, N.Y., USA, 1989).

Step 1. Isolation of a chromosomal region from *Saccharothrix aerocolonigenes* which contains (among others) a gene encoding the rebeccamycin N-glucosyltransferase.

Example 1

Construction of a Genomic Library of the DNA of *Saccharothrix aerocolonigenes* ATCC39243

In order to isolate genomic DNA from *Saccharothrix aerocolonigenes* ATCC39243, a concentrated suspension of spores from this organism was used to inoculate 250-ml Erlenmeyer flasks containing 25 ml TSB medium (tryptone soya broth, Oxoid), and they were incubated at 28° C. for 48 hours. Cells were harvested by centrifugation and processed following the method for isolation of genomic DNA described in Kieser et al. (Practical *Streptomyces* genetics, The John Innes Foundation, Norwich, UK, 2000). This genomic DNA was then partially digested with restriction enzyme Sau3AI, yielding DNA fragments of about 30 kb in size. The requisite amount of enzyme and digestion time were determined empirically by analysis of the digestion using agarose gel electrophoresis. The enzymatic reaction was stopped by quick freezing, followed by phenol/chloroform extraction and ethanol precipitation.

For preparation of a genomic library of the DNA of *Saccharothrix aerocolonigenes* we used vector pKC505, which can replicate in both *Escherichia coli* and *Streptomyces* spp. Vector pKC505 was completely cleaved with restriction enzyme HpaI, followed by phenol/chloroform extraction and ethanol precipitation, and then treated with alkaline phosphatase (Boehringer Mannheim). After phosphatase inactivation, the vector was completely digested with restriction enzyme BamHI, followed by phenol/chloroform extraction and ethanol precipitation. The vector was then ligated to the (previously obtained) partially-digested genomic DNA by using T4 DNA ligase (New England Biolabs). This ligation mixture was in vitro packaged into lambda phage particles by using a DNA Packaging Kit (Boehringer Mannheim). The phage suspension was used to infect *Escherichia coli* ED8767 cells, and transductants were selected on plates containing TSA medium (tryptone soya broth [Oxoid] plus 2% agar) containing 20 µg/ml tobramycin. About 3000 randomly-chosen transductant colonies were grown on microtiter plates, forming a genomic library representative of the genomic DNA of *Saccharothrix aerocolonigenes*. For preservation, glycerol was added (25% final concentration) to the microtiter plates, which were stored at −70° C.

Example 2

Analysis of the *Saccharothrix aerocolonigenes* Genomic Library Using an ngt Probe The identification of those clones in the genomic library containing rebeccamycin biosynthetic genes was done by colony hybridization, using as a probe an internal fragment of the ngt gene from *Saccharothrix aerocolonigenes* encoding rebeccamycin N-glucosyltransferase (Ohuchi et al. *J. Antibiot.* 53: 393-403, 2000). A fragment of the ngt gene was obtained by standard PCR techniques, using genomic DNA from *Saccharothrix aerocolonigenes* as template (obtained following Example 1) and synthetic oligonucleotides CS003 SEQ ID NO: 20 and CS004 SEQ ID NO: 21, designed from the reported ngt sequence (Ohuchi et al. *J. Antibiot.* 53: 393-403, 2000). The identity of the amplified DNA fragment was confirmed by its cloning into vector pUC19 followed by nucleotide sequencing using standard molecular biology techniques. This DNA fragment was used as a probe in colony hybridization against the *Saccharothrix aerocolonigenes* genomic library. For this purpose, we used a DIG DNA Labeling and Detection Kit (Boehringer Mannheim) following standard procedures and manufacturer's recommendations. Several positive clones were obtained, and the corresponding cosmids were studied by Southern analysis using the same ngt probe. Four cosmids were selected that contained the ngt gene and showed overlapping restriction maps: (cosmids 10A4, 14E8, 17A12 and 24B2). Strain *E. coli* ED8767 harboring cosmid 14E8 was deposited on Oct. 10, 2001 at the Spanish Type Culture Collection (Colección Española de Cultivos Tipo, CECT), Universidad de Valencia, Campus de Burjassot, 46100 Burjassot (Valencia, Spain) with accession number CECT 5984.

Step 2. Transfer of the ability to biosynthesize rebeccamycin to a *Streptomyces* spp. microorganism by introduction of said chromosomal region.

Example 3

Transfer of the Ability to Biosynthesize Rebeccamycin to *Streptomyces albus*

Vector pKC505 (as a control) and the four cosmids including the ngt gene were separately introduced into a *Streptomyces* spp. strain by protoplast transformation, following a method described in Kieser et al (Practical *Streptomyces* genetics, The John Innes Foundation, Norwich, UK, 2000). The chosen host strain was *Streptomyces albus* J1074, which does not produce rebeccamycin or any other similar metabolites, though for this purpose any other actinomycete may be used as far as vector pKC505 can replicate in said microorganism. Several colonies from each transformation were grown at 28° C. for 10 days in solid R5A medium containing 25 µg/ml apramycin and 2.2% agar. R5A medium is modified R5 medium described by Fernández et al. (*J. Bacteriol.* 180: 4929-4937, 1998). These cultures were acetone extracted, and the resulting extracts were analyzed by bioassay and by HPLC, screening for rebeccamycin. Bioassays were performed following standard microbiological techniques using the bacterium *Micrococcus luteus* ATCC1024, which is sensitive to rebeccamycin. The extracts obtained from *S. albus* J1074/14E8 transformants and *S. albus* J1074/17A12 transformants inhibited *M. luteus* growth, while the extracts obtained from control *S. albus* J1074/pKC505 had no apparent effect.

HPLC analysis was performed in a reversed-phase column (Symmetry C18, 4.6×250 mm, Waters), with acetonitrile and 0.1% trifluoroacetic acid in water as solvents. A linear gradient from 20% to 75% acetonitrile in 20 minutes, at a flow rate of 1 ml/min, was used. Detection and spectral characterization of peaks were performed with a photodiode array detector and Millennium software (Waters), and two-dimension chromatograms were extracted at 316 nm. HPLC analysis of extracts from S. albus J1074/14E8 and S. albus J1074/17A12 resulted in similar chromatograms, with two new peaks (FIG. 2, B) not detected in the extract from control S. albus J1074/pKC505 (FIG. 2, A). The major peak eluted with same retention time than a sample of pure rebeccamycin (FIG. 2, C) and showed rebeccamycin characteristic absorption spectrum. The minor peak, while having a different retention time, also showed rebeccamycin-like absorption spectrum. This minor peak could correspond to a rebeccamycin degradation product, as sometimes it is detected in HPLC chromatograms of pure rebeccamycin samples.

The compound corresponding to the major peak was purified as follows. Spores of strain S. albus J1074/14E8 were inoculated in TSB medium (tryptone soya broth, Oxoid) containing 25 μg/ml apramycin, followed by incubation for 24 hours at 30° C. and 250 rpm. This seed culture was used to inoculate (at 2.5%, v/v) eight 2-liter Erlenmeyer flasks containing 400 ml of R5A medium. After incubation for 5 days at 30° C. and 250 rpm, cells were harvested by centrifugation (12000 rpm, 30 min). The relevant compound was found largely associated with the mycelium; therefore, the supernatant was discarded. The mycelium was extracted with 400 ml acetone, shaken for 2 hours, centrifuged, and the organic extract was evaporated in vacuo. This material was dissolved in 5 ml DMSO:acetone mixture (50:50) and chromatographed in a μBondapak C18 radial compression cartridge (PrepPak Cartridge, 25×100 mm, Waters), via isocratic elution with acetonitrile:water (55:45) at 10 ml/min. The purified compound was collected after multiple injections, dried in vacuo and finally lyophilized. This compound was analyzed by MALDI-ToF mass spectrometry using a Voyager-DE STR Biospectrometry Workstation. As result of this, a major peak was obtained with a mass of 568 corresponding to rebeccamycin, and a secondary peak with a mass of 392 corresponding to rebeccamycin aglycon.

Rebeccamycin production levels obtained in strain S. albus J1074/14E8 were several fold greater than the levels observed in the same conditions with the natural strain Saccharothrix aerocolonigenes ATCC39243.

Example 4

Transfer of the Ability for Rebeccamycin Resistance

Rebeccamycin displays antibacterial activity against some Gram-positive bacteria (Bush et al. J. Antibiot. 40: 668-678, 1987), and it produces a weak inhibition of growth against some Streptomyces spp. including S. albus J1074. Therefore, cosmids 14E8 and 17A12, which conferred the ability to produce rebeccamycin, should also confer resistance to rebeccamycin. In order to confirm this point, we studied the effect of exogenously added rebeccamycin on the growth of S. albus J1074/14E8 and control strain S. albus J1074/pKC505. For this purpose, spores of each strain were used to inoculate plates of Bennett's agar (Kieser et al. Practical Streptomyces genetics, The John Innes Foundation, Norwich, UK, 2000) containing 25 μg/ml apramycin. Different amounts of rebeccamycin (dissolved in acetone) were added to paper discs placed on this pre-seeded medium. The plates were left at 4° C. for an hour to allow diffusion of the rebeccamycin solution, and then they were incubated at 28° C. for 4 days. In the described conditions, growth of control strain S. albus J1074/pKC505 was totally inhibited by 100 μg rebeccamycin, whereas S. albus J1074/14E8 was fully resistant to 100 and 200 μg rebeccamycin.

Step 3. Determination and analysis of the nucleotide sequence of the gene cluster responsible for rebeccamycin biosynthesis.

Example 5

Determination and Analysis of the Nucleotide Sequence of the Insert in Cosmid 14E8

Cosmid 14E8 was chosen for further study, and the complete DNA sequence of its insert was determined. Sequencing was performed on double-stranded DNA templates in pUC18, using the dideoxynucleotide chain termination method and the Cy5 AutoCycle Sequencing Kit (Amersham Pharmacia Biotech). Both DNA strands were sequenced, using an Alf-Express automatic DNA sequencer (Amersham Pharmacia Biotech). Computer-aided sequence analysis was carried out using software by the University of Wisconsin Genetics Computer Group (GCG). The determined sequence (SEQ ID NO:1) consisted of 25,681 nucleotides. Computer-aided analysis of this sequence revealed the presence of 16 complete open reading frames (ORFs) and two incomplete ORFs (FIG. 3). Gene products deduced for these ORFs were compared to proteins of known function (available in public databases) by using the BLAST program. This allowed us to propose putative functions for most of the ORFs, as shown in Table 1.

TABLE 1

| Gene | Position | Amino acids | Deduced function | Notes |
|------|----------|-------------|------------------|-------|
| orfD13 | 1-136 | 44 | | SEQ ID NO: 2 |
| OrfR5 | 302-3313 complement | 1003 | regulatory protein | SEQ ID NO: 3 |
| OrfR4 | 3395-4027 complement | 210 | dipeptidase | SEQ ID NO: 4 |
| OrfD1 | 4402-5718 | 438 | esterase | SEQ ID NO: 5 |
| OrfR3 | 5946-6347 complement | 133 | | SEQ ID NO: 6 |
| OrfD2 | 6581-7768 | 395 | | SEQ ID NO: 7 |
| OrfR2 | 7841-9106 complement | 421 | N-glucosyltransferase | SEQ ID NO: 8 |
| OrfD3 | 9316-10737 | 473 | L-tryptophan oxidase | SEQ ID NO: 9 |
| OrfD4 | 10734-13775 | 1013 | | SEQ ID NO: 10 |
| OrfD5 | 13772-15361 | 529 | monooxygenase | SEQ ID NO: 11 |
| OrfD6 | 15358-16551 | 397 | cytochrome P450 | SEQ ID NO: 12 |
| OrfD7 | 16578-17399 | 273 | methyltransferase | SEQ ID NO: 13 |
| OrfD8 | 17730-20501 | 923 | regulatory protein | SEQ ID NO: 14 |
| OrfD9 | 20498-21010 | 170 | flavin reductase | SEQ ID NO: 15 |
| orfD10 | 21007-22287 | 426 | membrane transporter | SEQ ID NO: 16 |
| orfD11 | 22271-23863 | 530 | tryptophan halogenase | SEQ ID NO: 17 |
| OrfR1 | 23933-25354 complement | 473 | membrane transporter | SEQ ID NO: 18 |
| orfD12 | 25439-25681 | 81 | regulatory protein | SEQ ID NO: 19 |

Step 4. Expression of certain genes from the mentioned gene cluster in a host organism, in order to produce rebeccamycin-derived indolocarbazoles.

Example 6

Construction of Recombinant Plasmids pREB5, pREB6 and pREB7

In order to determine the minimal amount of DNA needed to direct the biosynthesis of rebeccamycin or rebeccamycin derivatives, three new plasmids were constructed (pREB5, pREB6 and pREB7) containing fragments of the insert present in cosmid 14E8 (FIG. 4). For this purpose, standard molecular biology techniques were used as described in Sambrook et al. (Molecular cloning: a laboratory manual, Cold Spring Harbor Laboratory Press, Cold Spring Harbor, N.Y., USA, 1989).

Plasmid pREB5 was made by inserting a DNA fragment encompassing nucleotides 7119 (Bg/II) and 17783 (EcoRI) of SEQ ID NO:1 into vector pWHM3 (Kieser et al. Practical *Streptomyces genetics*, The John Innes Foundation, Norwich, UK, 2000). Plasmid pREB6 was constructed by inserting a DNA fragment encompassing nucleotides 8562 (Bg/II) and 17783 (EcoRI) of SEQ ID NO:1 into vector pEM4 (Quirós et al. *Mol. Microbiol.* 28: 1177-1185, 1998). Finally, plasmid pREB7 was made by inserting a DNA fragment encompassing nucleotides 7119 (Bg/II) and 22241 (EcoRI) of SEQ ID NO:1 into vector pWHM3 (Kieser et al. Practical *Streptomyces* genetics, The John Innes Foundation, Norwich, UK, 2000).

All three plasmids can replicate in high copy number in *E. coli* and in *Streptomyces*, due to the choice of vectors used for their construction. In pREB5 and pREB7, putative expression of the included genes might occur due to their own natural promoter and regulatory sequences. However, plasmid pREB6 contains an additional promoter, from the erythromycin resistance gene (ermE) of *Saccharopolyspora erythraea*, which would cause a constitutive expression of the included genes. Choice of different vectors and/or addition of particular promoter or regulatory sequences allow the expression of the mentioned genes in different organisms.

Example 7

Production of Rebeccamycin Intermediates in *Streptomyces albus* Directed by Plasmids pREB5, pREB6 and pREB7

Plasmids pREB5, pREB6, pREB7, and control pEM4 were separately introduced into *Streptomyces albus* J1074 by protoplast transformation, as described in Kieser et al. (Practical *Streptomyces* genetics, The John Innes Foundation, Norwich, UK, 2000). We chose again *Streptomyces albus* J1074 as host strain but many other actinomycetes can be utilized, due to the wide host range of the vectors used for construction of pREB5, pREB6 and pREB7. Transformants were grown and extracts were obtained that were analyzed by HPLC, under conditions described in Example 3.

Extracts obtained from transformants *S. albus* J1074/pREB5 did not appear to contain any indolocarbazole, and their HPLC chromatograms were essentially identical to those of extracts from control strain *S. albus* J1074/pEM4 (FIG. 5, A).

HPLC analysis of extracts from transformants *S. albus* J1074/pREB6 (FIG. 5, B) showed a new product, which we called RM62, with an elution time different to that of rebeccamycin (FIG. 5, D). Comparison of RM62 absorption spectrum (FIG. 6, B) to that of rebeccamycin (FIG. 6, A) indicates that RM62 is actually an indolocarbazole, derivative or precursor of rebeccamycin. This finding suggests that the lack of indolocarbazole production in *S. albus* J1074/pREB5 is due to a low expression of the included genes, and this defect is circumvented in pREB6 by the additional promoter from the erythromycin resistance gene.

HPLC analysis of extracts from transformants *S. albus* J1074/pREB7 (FIG. 5, C) showed two new products: RM761 (minor product) and RM762. Both RM761 and RM762 had elution times different to that of rebeccamycin (FIG. 5, D), but their absorption spectra (FIG. 6, C-D) indicate that they are rebeccamycin derivatives or precursors. Comparison of these results to those obtained with pREB5 and pREB6 suggests that the DNA fragment included in pREB7 contains some regulatory element (probably orfD8) that stimulates the expression of the indolocarbazole biosynthetic genes.

Introduction, in a particular organism of rebeccamycin biosynthetic genes described within the present invention can be utilized for different purposes, including:

(1) If the said organism does not naturally produce any kind of indolocarbazole, rebeccamycin biosynthetic genes can be utilized for:
 (a) Production of rebeccamycin, by using the complete gene cluster.
 (b) Production of rebeccamycin biosynthetic intermediates, by the use of a part of the gene cluster.
 (c) Obtaining an organism resistant to rebeccamycin.
(2) If additional genes from different organisms are introduced into an organism as the one described in paragraph (1), production of rebeccamycin derivatives can be achieved. For instance, if a gene encoding for a particular tryptophan modifier enzyme (e.g. hydroxylase) is introduced, rebeccamycin derivatives with specifically modified indolocarbazole aglycons (e.g. hydroxylated at certain positions) can be obtained. Another example: if one or several genes involved in biosynthesis of a particular sugar are introduced, it is possible to obtain rebeccamycin derivatives with new sugars in place of 4-O-methyl-β-D-glucose.
(3) If the said organism naturally produces some kind of indolocarbazole (such as staurosporine, K-252a, UCN-01, J-104303, AT-2433, arcyriaflavins, arciryarubin, arcyriacianin, arcyroxocin, arcyriaverdin, etc.), rebeccamycin biosynthetic genes can be utilized for:
 (a) Yield improvement in the production of the said indolocarbazole, by using a regulatory gene such as orfD8.
 (b) Production of new ("hybrid") indolocarbazoles, by the use of the complete rebeccamycin gene cluster or by the use of a part of the gene cluster. For instance, if gene orfD11 (or both genes orfD9 and orfD11) coding for a tryptophan halogenase is introduced, new halogenated indolocarbazoles can be obtained. Another example: if gene orfR2 or gene orfD7 (or both) are introduced, new indolocarbazoles with modified sugars can be obtained.
(4) If the said organism naturally produces some non-indolocarbazole metabolites biosynthesized from tryptophan (such as violacein), rebeccamycin biosynthetic genes can be used for production of new ("hybrid") derivatives of the said metabolites, in a similar way to that described in paragraph (3b).

SEQUENCE LISTING

<160> NUMBER OF SEQ ID NOS: 21

Figure 1:
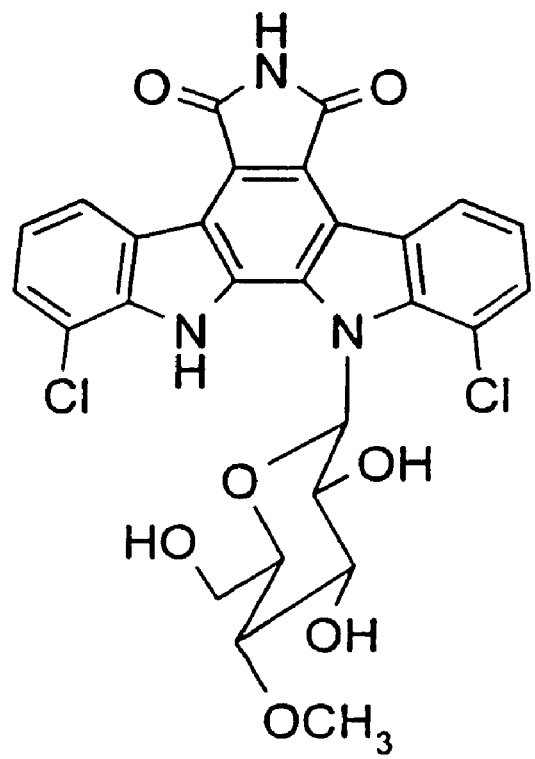
FIG. 1. Structures of rebeccamycin (A) and staurosporine (B).
Figure 1:
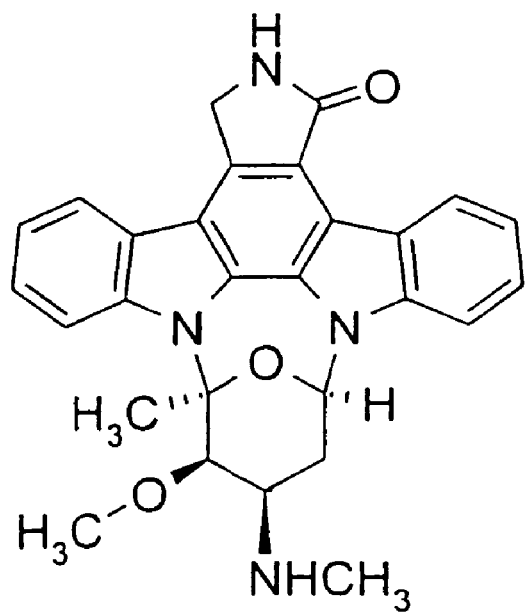
Figure 2:
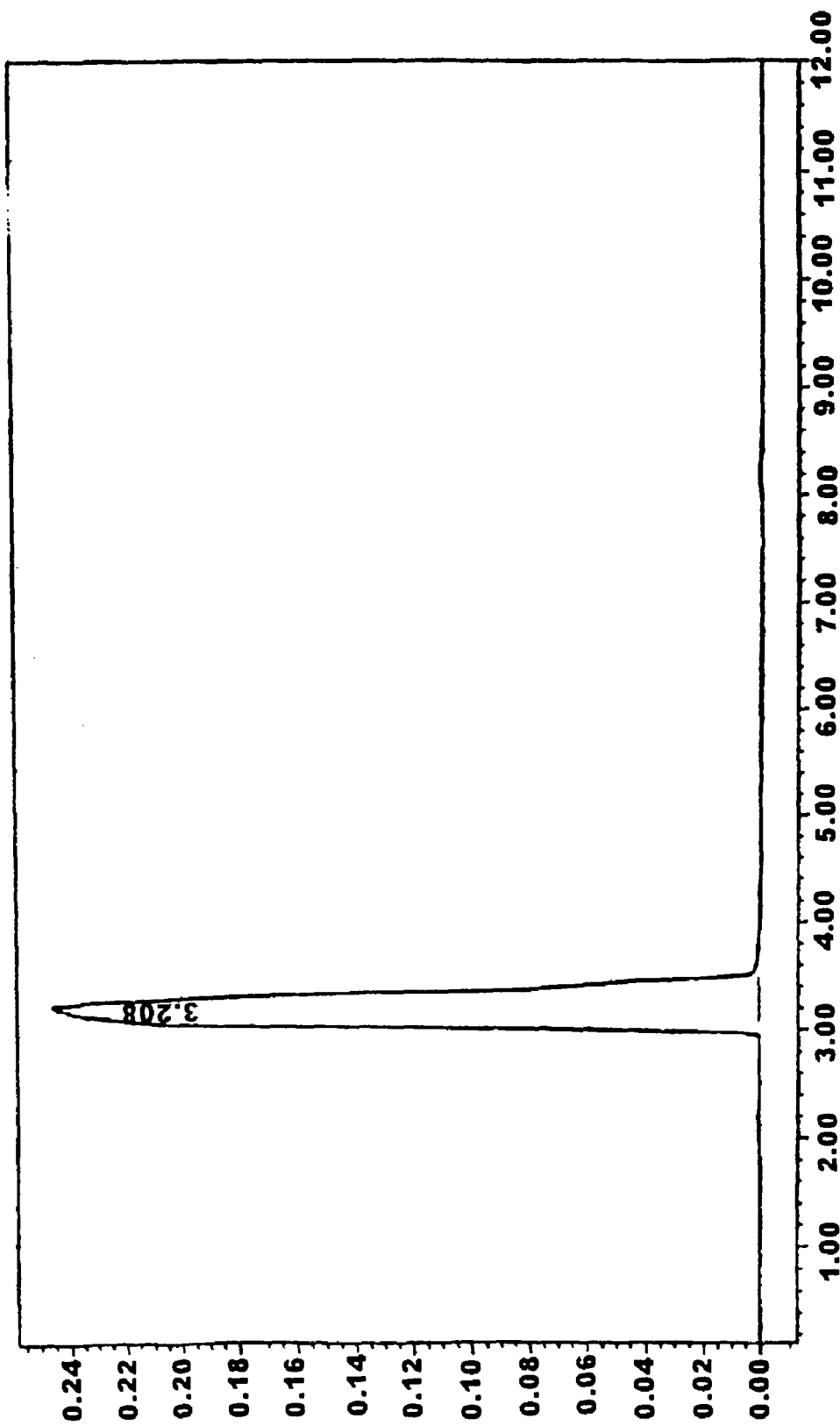
FIG. 2. HPLC analysis of:
(A) An extract from *Streptomyces albus* J1074/pKC505.
(B) An extract from *S. albus* J1074/14E8.
(C) A sample of pure rebeccamycin.
Figure 2:
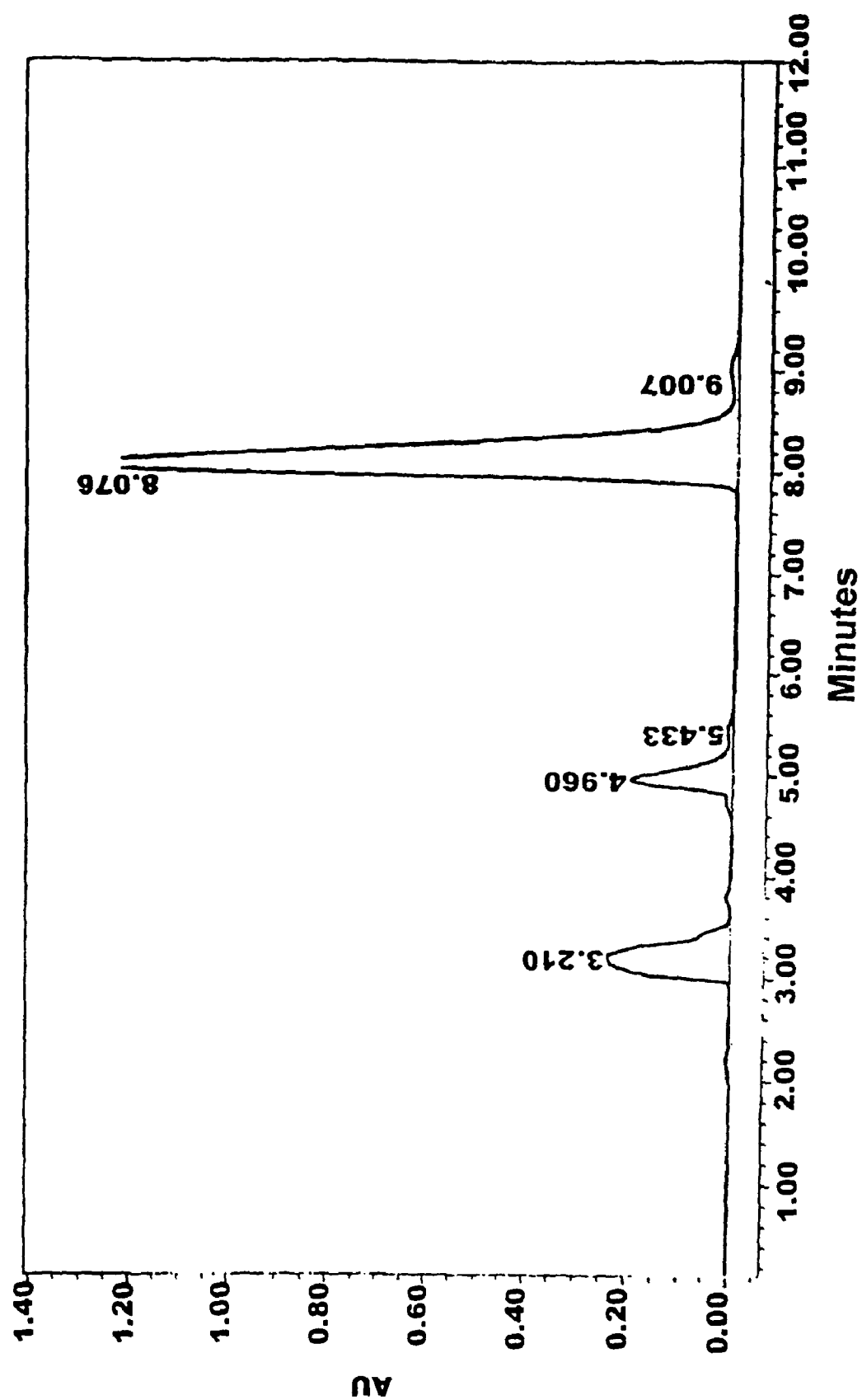
Figure 2:
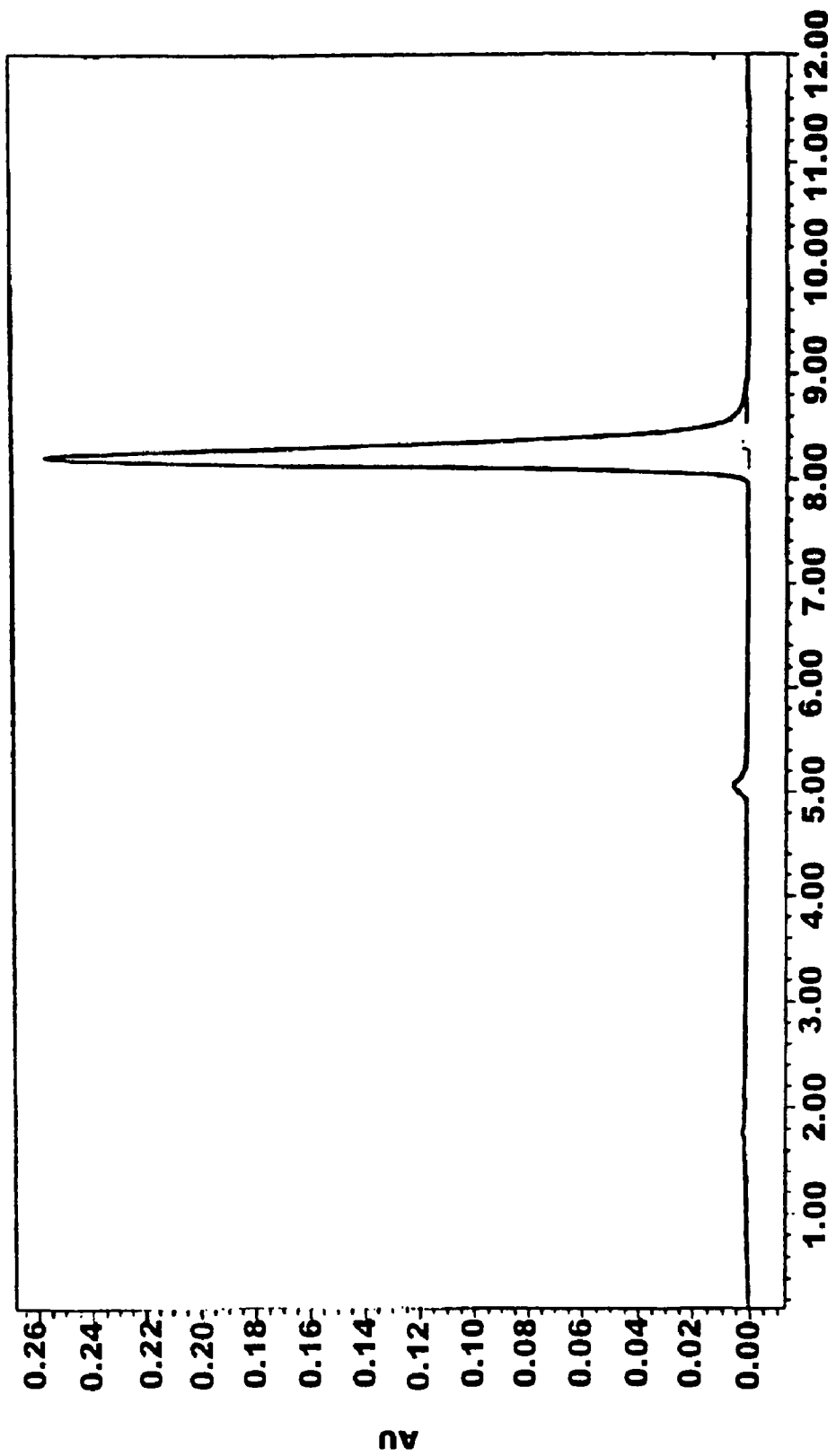
Figure 3:
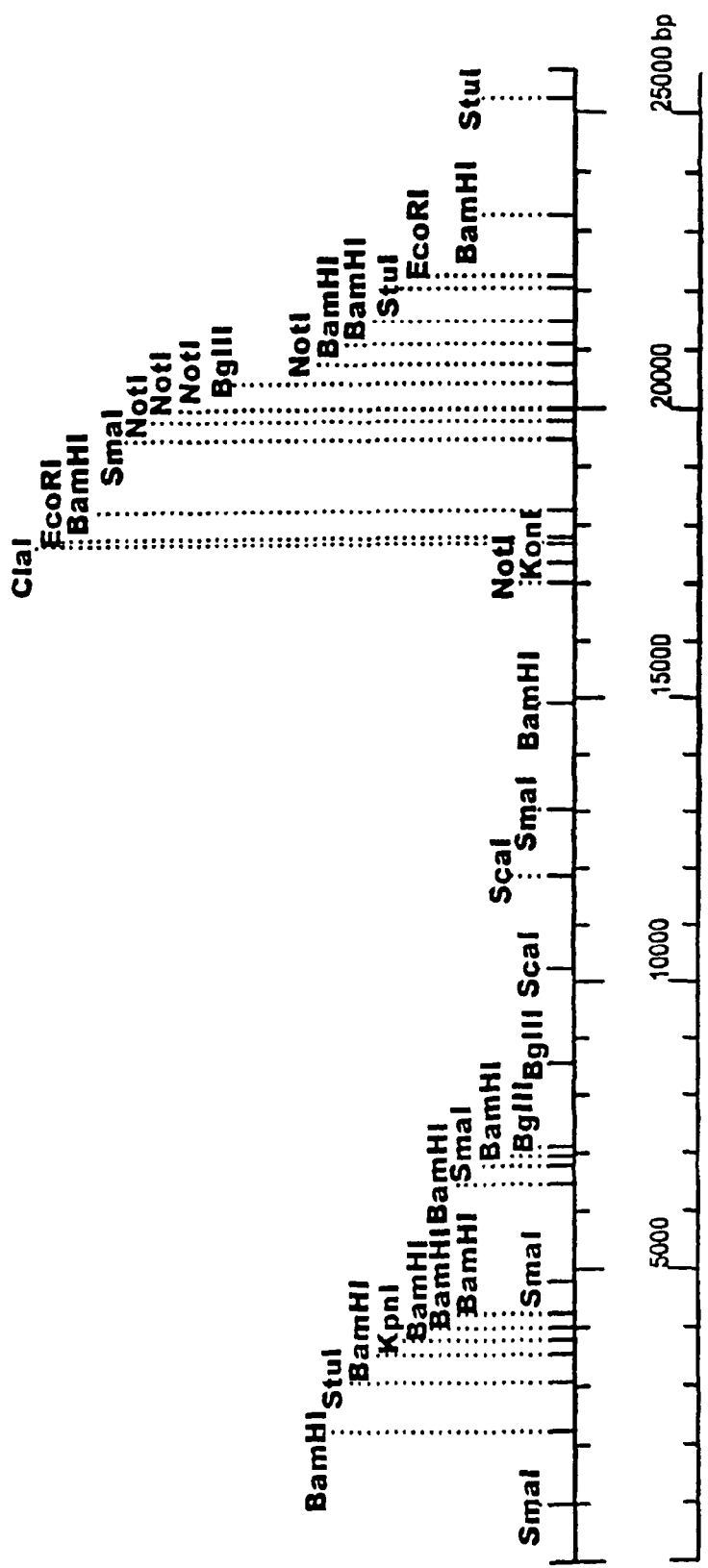
FIG. 3. Restriction map of the insert contained in cosmid 14E8, which includes the rebeccamycin biosynthetic gene cluster.
Figure 4:
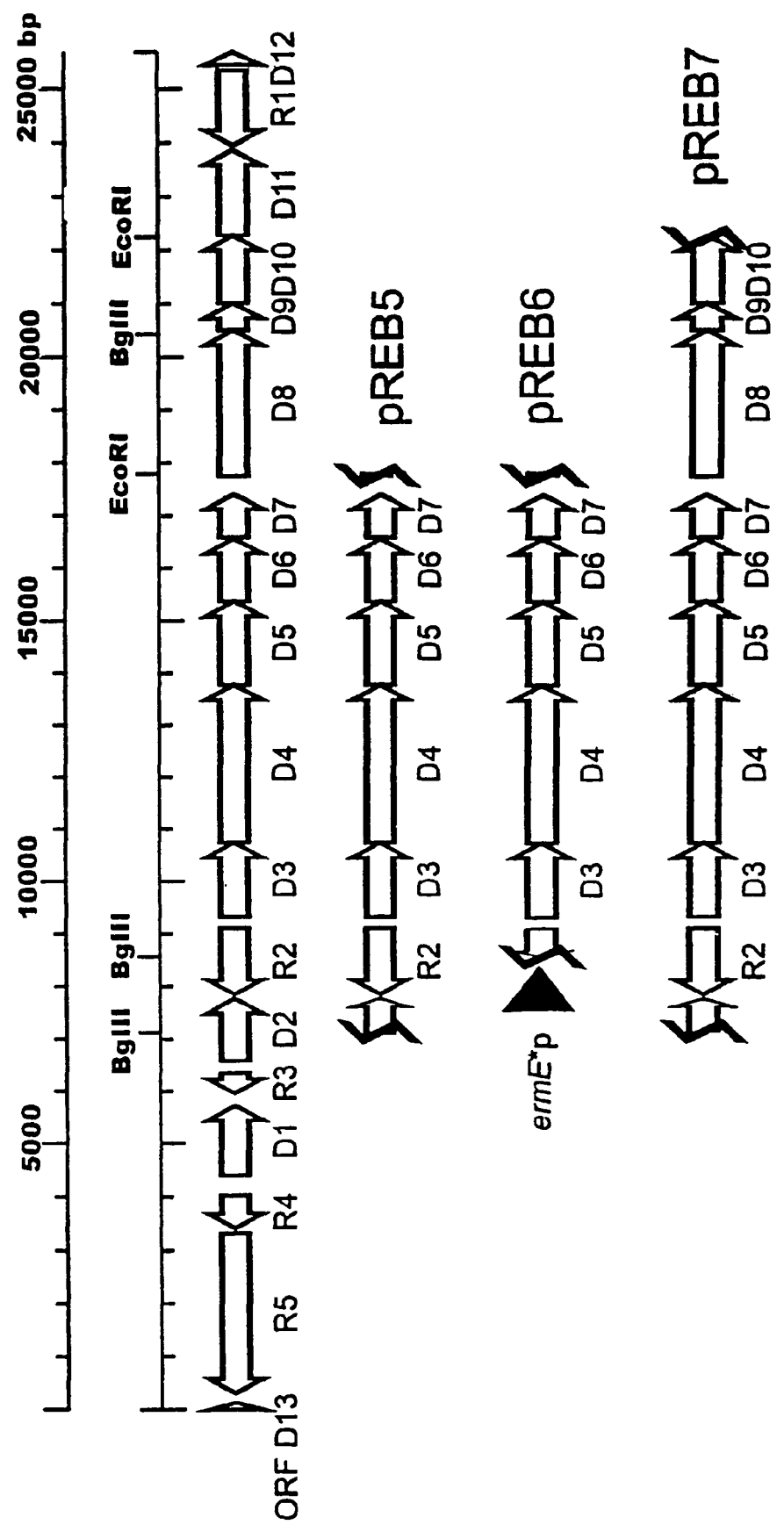
FIG. 4. Scheme of inserts included in plasmids pREB5, pREB6 and pREB7.
Figure 5:
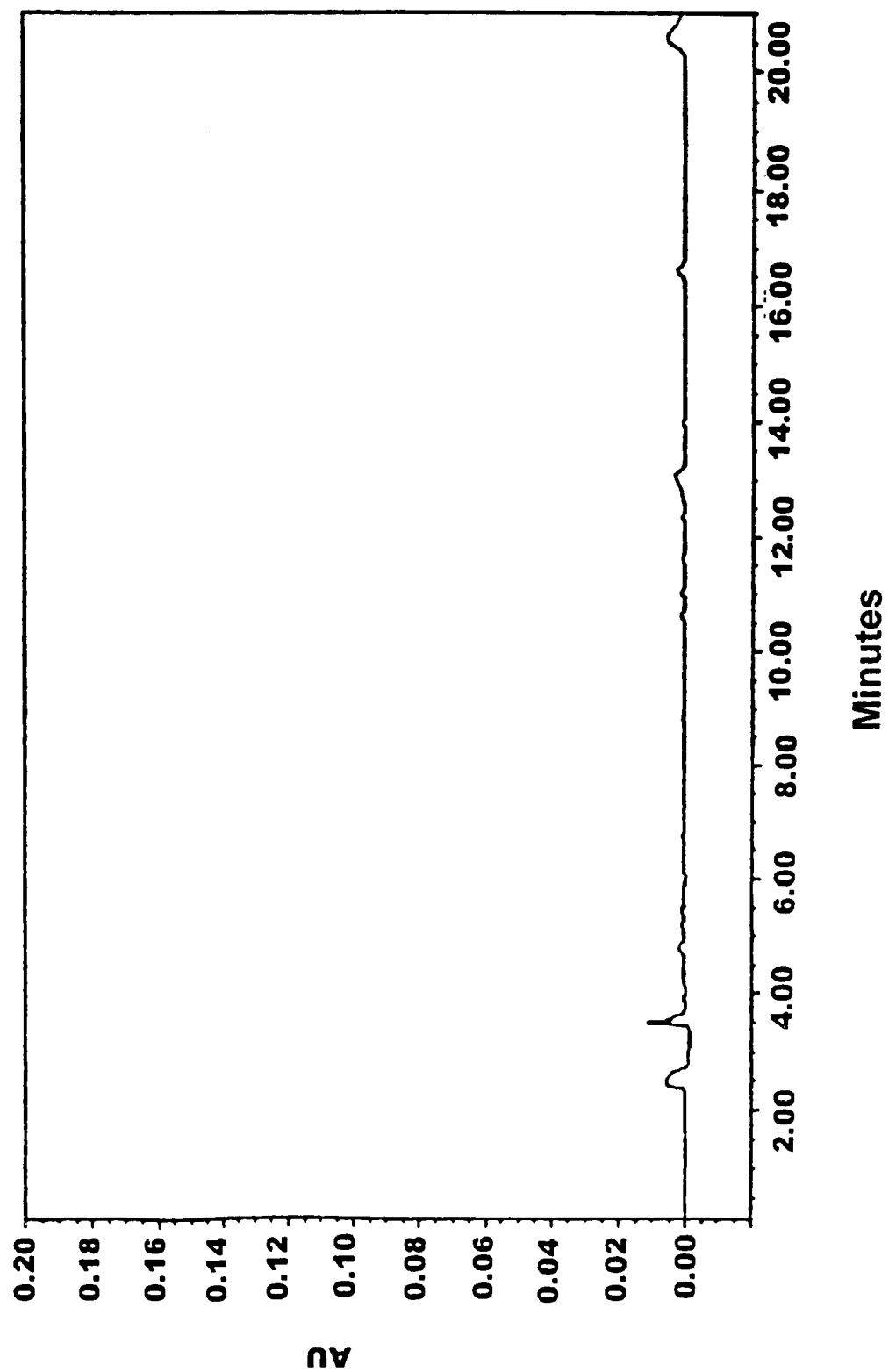
FIG. 5. HPLC analysis of:
(A) An extract from *S. albus* J1074/pEM4.
(B) An extract from *S. albus* J1074/pREB6. The major peak corresponds to product RM62.
(C) An extract from *S. albus* J1074/pREB7. The major peak corresponds to product RM762. The minor peak, around minute 12.3, corresponds to product RM761.
(D) A sample of pure rebeccamycin.
Figure 5:
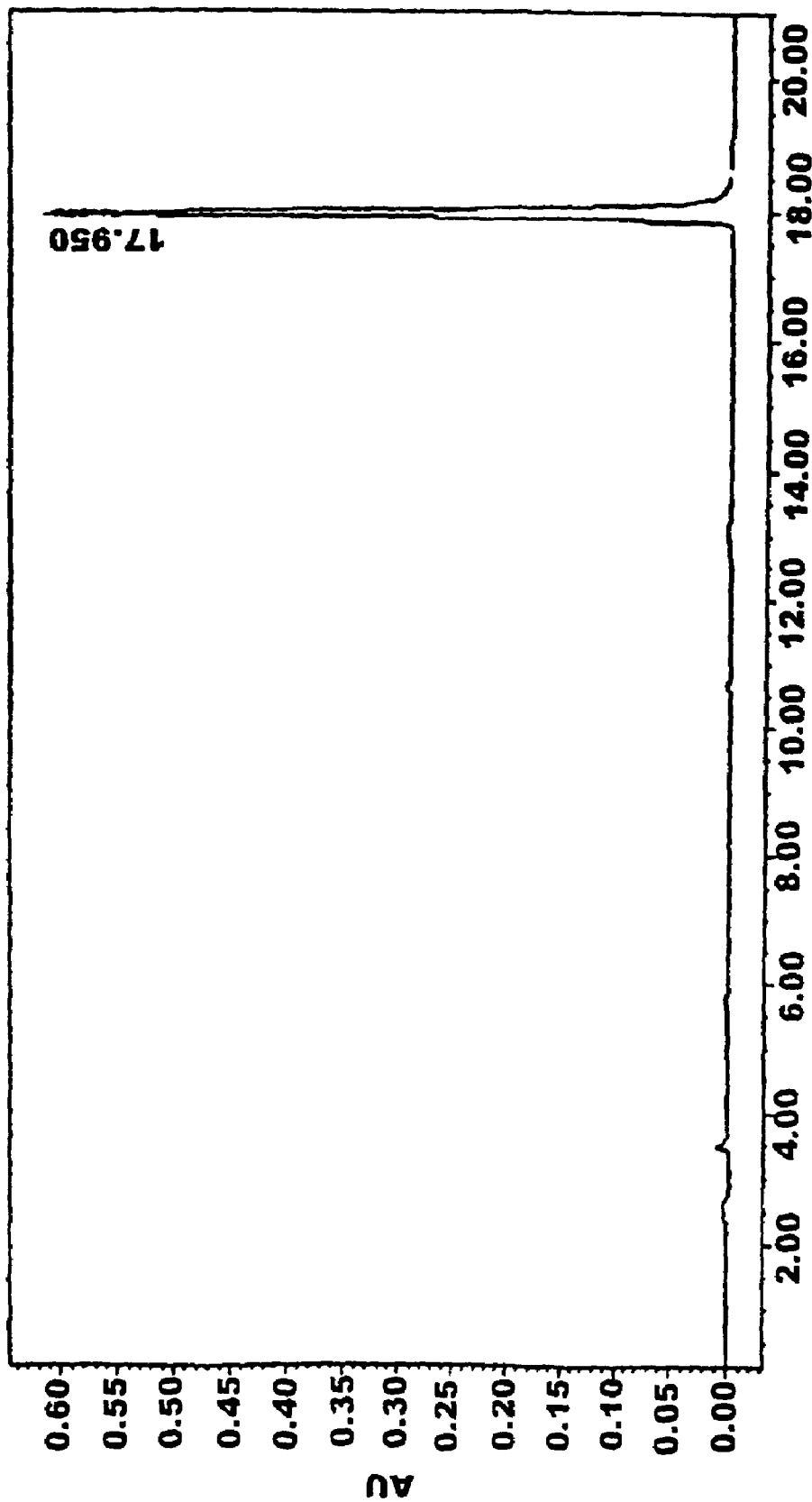
Figure 5C:
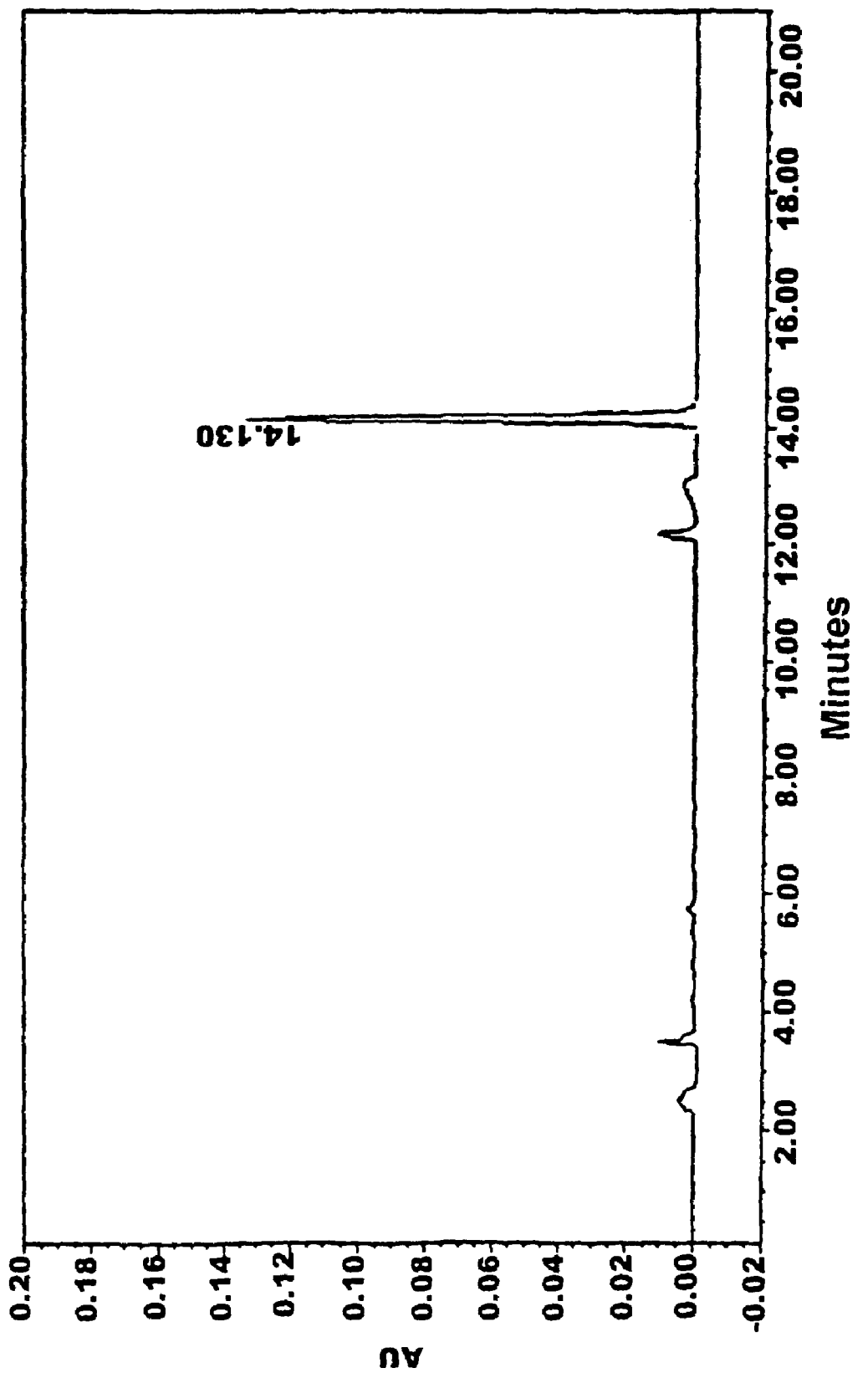
Figure 5:
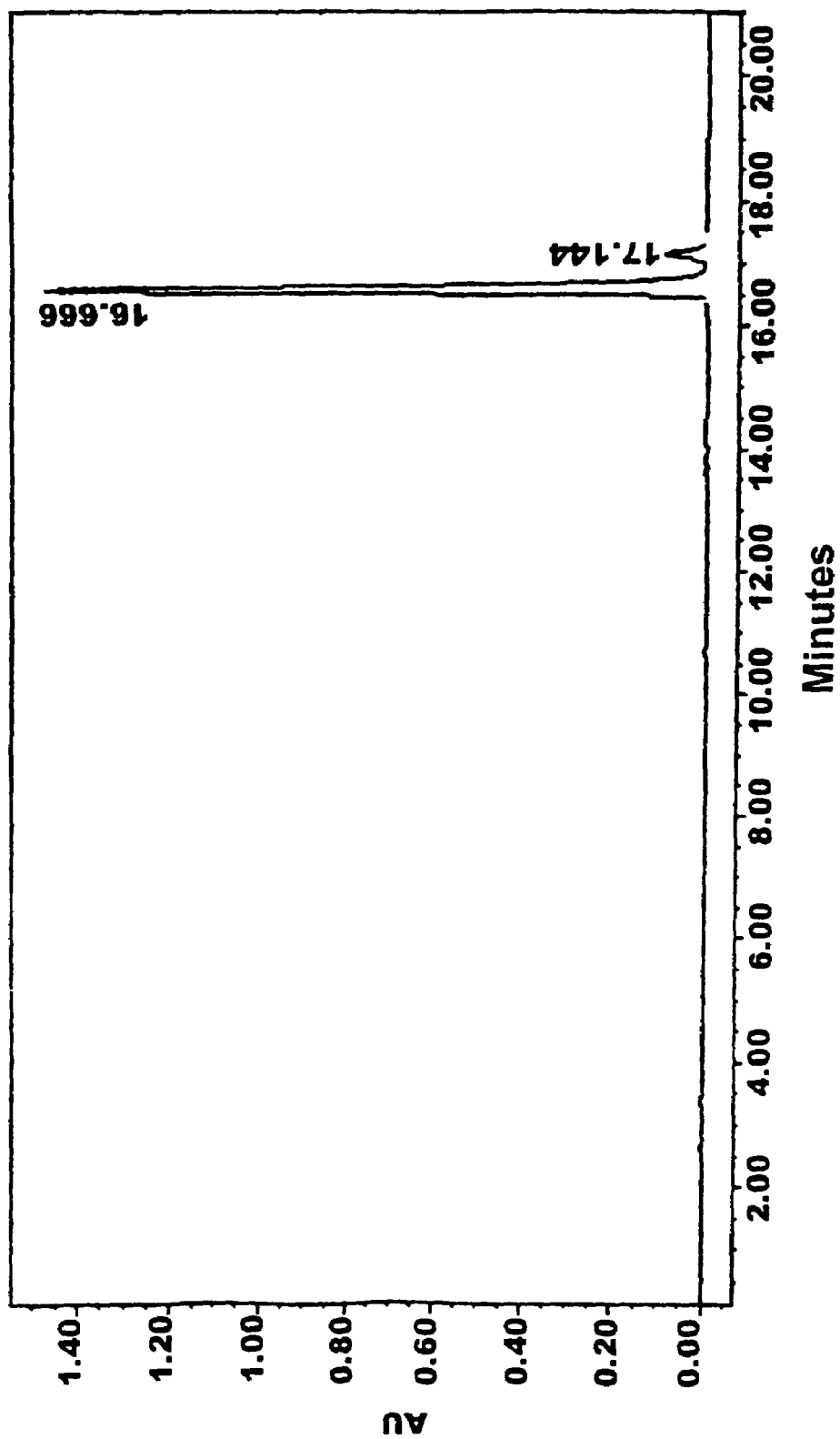
Figure 6:
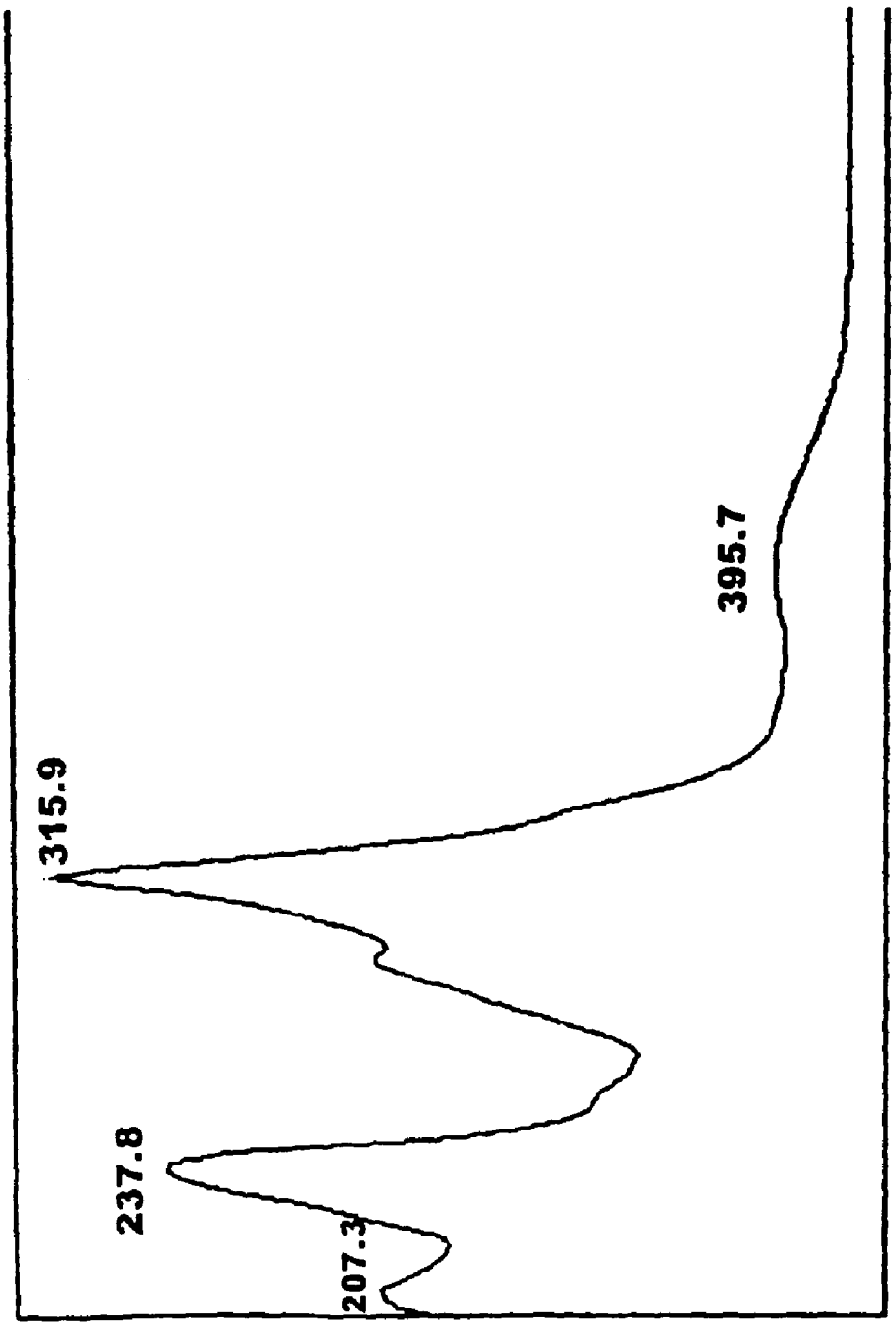
FIG. 6. Absorption spectra of:
(A) Rebeccamycin.
(B) Product RM62, from an *S. albus* J1074/pREB6 extract.
(C) Product RM761, from an *S. albus* J1074/pREB7 extract.
(D) Product RM762, from an *S. albus* J1074/pREB7 extract.
Figure 6:
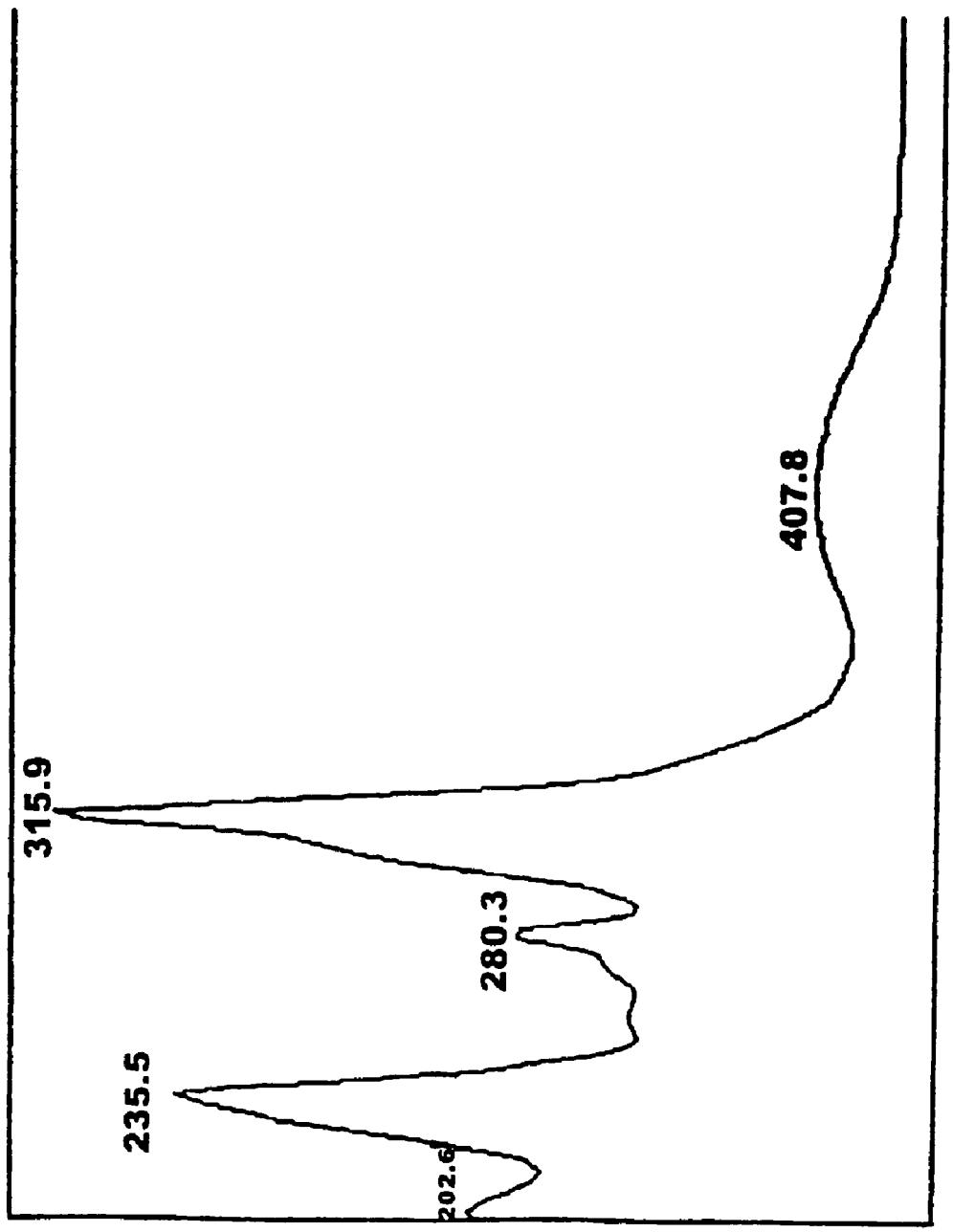
Figure 6:
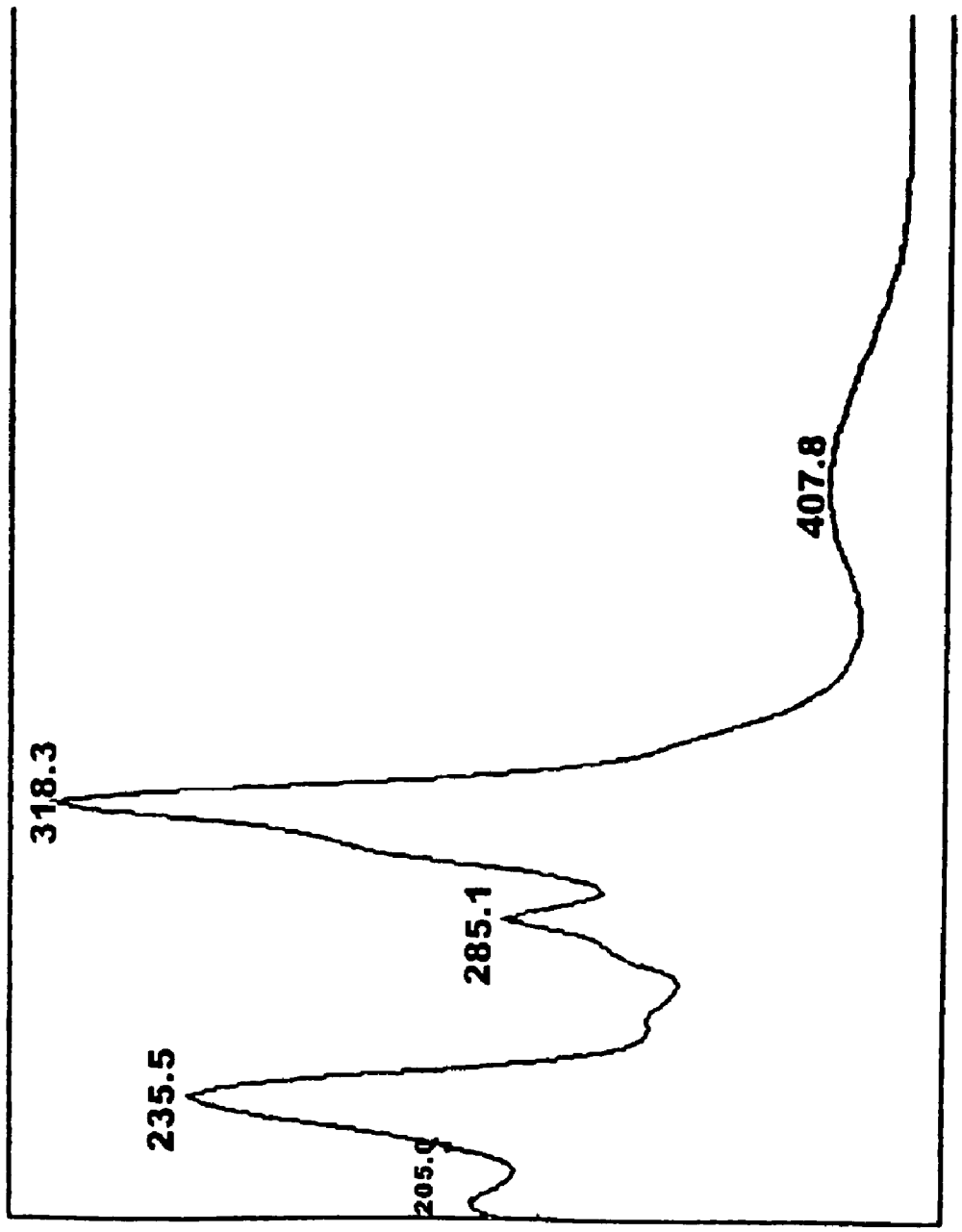
Figure 6:
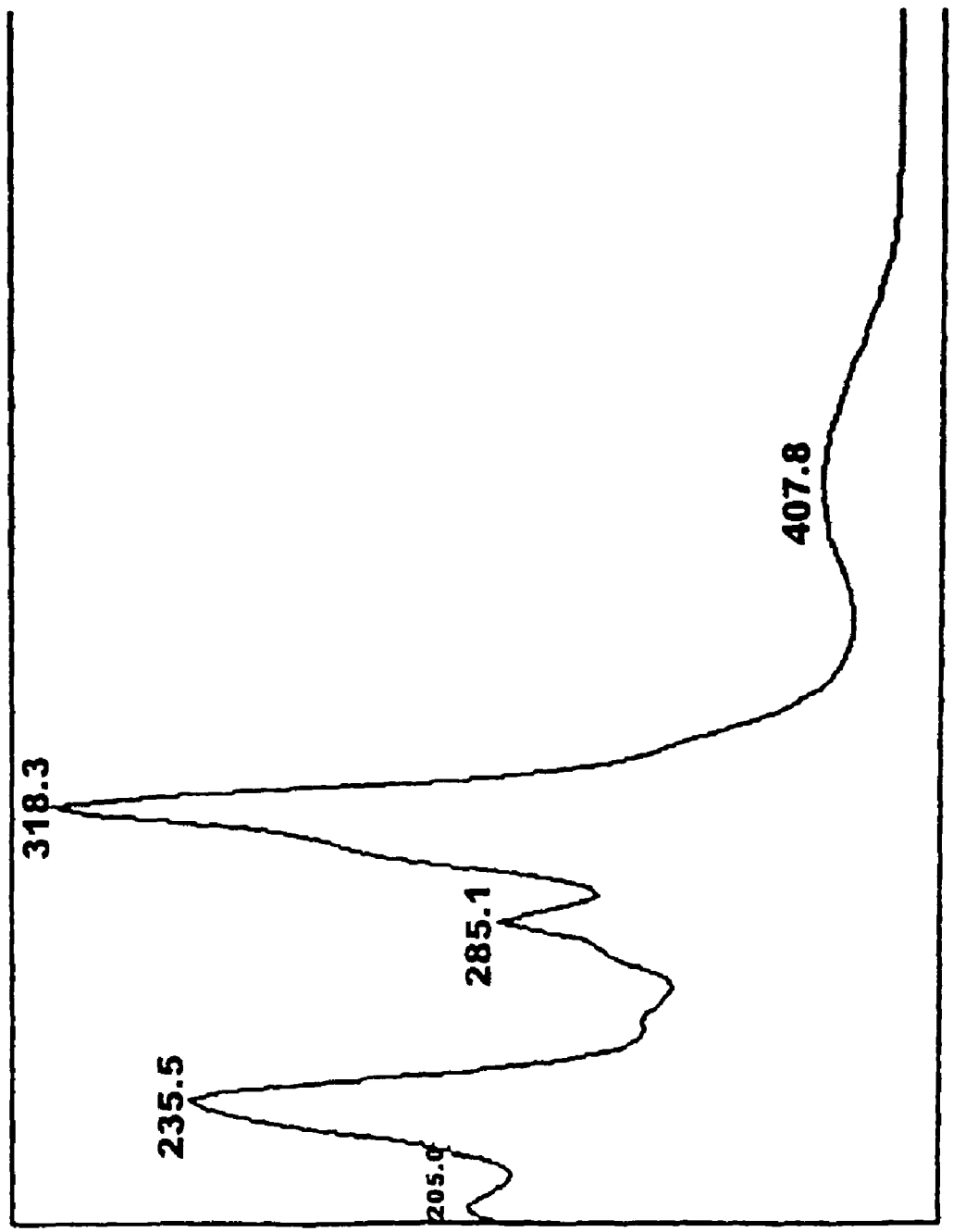

<210> SEQ ID NO 1
<211> LENGTH: 25681
<212> TYPE: DNA
<213> ORGANISM: Saccharothrix australiensis

<400> SEQUENCE: 1

```
gatcttcacg tacgccgacc acaacggtcg gcatattcgg ttcggcgtgg acttctattg      60
cggcggcacg gcaagtctcg ccgaaccaga agttagcacg cgccacgacg gccgaactcc     120
catttcccga ggttaggacg taaggagtcc cacgaggagt tgactggcgg acacgatttc     180
atccgaacgg cacgtatctg gcctttaccg gtgagttctc gagattccgt cccgcctgtg     240
gcaggttcta caccgggccc atcgtccaca gtggaacgag cggcagaccg tccgcgcgga     300
tctacaccgg cagttcggcg tactccgaat actcccgcgc ccctcgcgcg cggaacaccg     360
accgggcgtg cgtgaatgcc gcgtccgccg cctgcgtgtc accccggctc cggtgcagca     420
gcgcgaggtc gtattccgtg cgcgcccgcc acagcggtgc ctccgtggcg tcccagatcg     480
acatcgccgc gtcgagacag tcctgcgcga ggtccagccg tccctctgcc aggtgcaact     540
gtccgagcac gcgcagggtg atggcctggc ccagcggtc gtccttggcg cgcacggtgg     600
cgagcgccat ttcgagccgg ggcaacgcct ccgcgctgtg gcccgatcgc atctgcgcct     660
tggcgtgtgc ccgcacggcg taggagtgca tgaggtcgtc gccgagttcg gcgaagatcg     720
tggcggcgtc ggcgcacacg gccatggacg tctcgtagtc gccacgcgcc cggtggtaga     780
gacccaggct gcgcaacgac agtgcgatcc cacgtctgct gccggcccgc cggtacgcgg     840
ccagtgactg ctccaggtcc gtcctcgcct cgtcgtactc gcccagttcc aggcggaccg     900 aaccctgat ccgcagcacg tgcccgatgc ccacctgatc gtcgagcgcc tgggacaggg     960
tggccgcctg gctcaggaag tgcacagcct cggtcaggtg cccgggttcg cggcacgcga    1020
ggcccatccc ggcgagtgcg gcggcctggc cccgcacgtc gtgcaggtcg cggtagcggc    1080
ccagcgcctc gccgaagagc tggcgggcct cggcgaagcg gtcctgggag aaccgcaggc    1140
gcgcgagttt ggccagcacg tccgcggcga ggccggggtc gccgacgtgc tggaccgacg    1200
tcatcgccac gccgatgatc cggtcgcgga ggtcgtagga gttggtcacc tgctcgatcg    1260
cggtgtgggc cgagacgaag tcgcacacgt gccggtgcag gccggtggcg gcggcgcgtt    1320
cgaccgccac cgcgagcgcc ggttcctcac cccgcagcca ggcgtcgagg tcgtcggaca    1380
gccgttcggc catggcggtg acaccgtcgg gttcccggtg cccggcggcc ggacgccagg    1440
tggactcggc cggagggctg ttcacggccg tgcggctcag cagggcgatc cagccgtcca    1500
ggacgcgggc gatcgacgcg gtcagctcgt cgggctcgtc ggcctccgct cgttcgcggg    1560
cgtagagccg gaccaggtcg tgcagccggt agcgcaggac tccgccgcg tcggcgccgg    1620 acaacgtggc cagttgcgcg tcgacgagca cctccaggac cttctccgcg tccgcctcgg    1680
acgtctcgag cagccagctc accacccagg tggagaagtc gggcaggccg aggtgtccca    1740
```

```
tccggcccag tgccgtgcgg gcctggtcgt cgagtgcccg gcagctcaac gcgatgctgc   1800
tgcgcacggc caggtcgccc gcggagagtt cgttgagacg gcggcgttcg tcggtcaggc   1860
ggtcggcgag gacccgcagc ggcaactgcc gccgtgaggc caggcgggcg ccggcgatcc   1920
gcaacgcgag cggcaggcgt ccgcacgcgt cgacgatccg gtgcgccgag tccacgttct   1980
ccgcgagccg cgcctcgccg acgatccgcg cgagcatgtc gtacgcctcg ccgggcgtca   2040
cgaggtccag ttcggtgaac agcgcccggg ccagtcccgc gaggcggtcg cgcgacgaga   2100
tgagcacggc acaaccggcg gcgcccggca gcagggcccg cacctgttcc tcggacgcgg   2160
cgtcgtcgag cacgacgagc acccggcgac cggcgagcga cgtccggtag agctcctggc   2220
gttcctgcgc cgactcgggc aactggccgg gatccatccc gagcgcggtc aggaacctgc   2280
ccagtacctc gcccgcggtc gcgggcaggc cgctcgtgcc gcggagttcg gcgtagagct   2340
ggccgtcggg gaacgaccgg gccgcctcgt gcgcggcgcg gacggtcagc gcggacttcc   2400
cgcaccctcc cggtcccgcc acgatctgca cggcggaggt ctccccgcac agcgcggcga   2460
cgagttcccc cagttcccgc acccggccgg tgaagtcggc gagcgtcgcg ggcaactgcg   2520
cgggcaccgc cgcgaacgcc gtgcgggcga ccggtgccgc gtccgccgga accagctcca   2580
gggtgccgcg caggatggcc gagtggatcg tgccgagctc ggctccgggt tccacgccga   2640
gttcgtcgac gagcgcgtcc cggccctccc ggtagcaggc gagcgcgtcg gcctgccgtc   2700
ccagccggta cagcgtcacc atgagctgcc gccgcaaccg ttcgttcacc ggctgccggg   2760
ccaccgcggc ggtcagctcg gcgaggtggt cgaaccggcc gaggcccagc tccgccgcga   2820
agcgttcctc ctgaacggtc accagcagtt cgtcgagccg ccgcgcctca ccgctcagca   2880
gcgtgtcccg caggccggac agcgcgggac gcgcgacag cgcgaccgcc tccccgagca   2940
gccgcgccgc cggttcatga ccgtgaacct ggctctgctg ccgggctttg ccgagcagac   3000
cggcgagttc gtcggcgtcc acgcgggcgt cgtcgaggcg gaccaggtag ccctgtgtct   3060
tcgacacgat cacgtcgggg gcaccgaggt cggcgaaggc cttgcgcagc ttggaaacgt   3120
acgtctggat gagcgaccgg gcactgacgg gcggttcctc accccacagc agctccacaa   3180
ggcggttcgc cggcaccacc cggccgcgtt ccagcaccag cgcggccagc agcacctgtg   3240
gcttcaggcc gccgagcggt acggatctgc cttccaccag ggcttcgacc ggaccgagta   3300
agcggaactc cagcaagttg tgacctcccc cgtgtcaccg gtgcaagtag atcacaccgg   3360
ccgagggggg ggggttcccg aaatggtgga tacatcaggg aagaatgggt ccgtagacgg   3420
cttgggacga tcccgtcagg tacgcccagt accgatcgcc gtaggaccag tgccaccacg   3480
cgctcgggta gttgaccagt ccggcgccgc gcaacgcccg cgcgagaacg gcgcggtggc   3540
ggcgcgccgt ggcgtccacc gtcggatcct cggtgtggga ccgctccgtc gcggtgtcgt   3600
tgaccgcggt gcccagatcg agctcgatct cgtccaccgt gcacaggctc aggtccaccg   3660
cggcaccggc gacgtgcggt gccacctccg gcggggagct gcgcacgctc gccctccgtc   3720
gcagcaccga ctcggcggcc cgcggtgagc gcgcacggga ctccgcgacg gccgactcga   3780
acgacgcgat ctgcaccgcg tgcggccggt acccctcgac gatcagcaac ctcagttcgg   3840
gcggcagcaa cgtctgcgcg gtgaccagcc gatccaccac accgatccgc agctgcgcgt   3900
acagcccctc ctcgtcggca agccggctgt cgagccgcag ggcggcaaca gtgcgcaggt   3960
cgaccagggg ctcgccgcgc tcgcgcaccg ggatcgccgc cacagcggga tccgacagcc   4020
acaccatctc caacgcctcc tcctggtcca ccgttctgaa cacgcggtcg cacgacggtg   4080
caggcacgta ctggaatttt tctttaacgc cacgtacgtc cgtccggacg cagccggtgc   4140
```

```
gtccggtggc gcgcgccttg cggcacaacg tctcgtgcac gcctcctggt ctgcggttaa    4200
aggtttcgtg gaccgtcctg aaacccctcc tggcgaacgt tggatccatc accggccgga    4260
cacaccgacc ggatcccgca ccagaaccga ggagaacccg tgttccgctc aggaatcagc    4320
cgcaccggca ccgagtccaa gtccgtcggc accggcctgc gcaagaccac ccgcaccctg    4380
ctgtccgcgg cgctggccgt gatggccggc accgtcctga tggcaccgcc cgccagcgcc    4440
gccccgtcga gagaccgcat cgtcaaggcc gccgccgacg aggtcggcga gggcgcctgc    4500
tcgcccggtt acttcaacag ctgcggcatg gcgtggtgcg cggagttcgc tcgctgggtg    4560
tggaacgagg gcggcgtctc ggatctcaag ggcctcgacg gctgggcgca gtcgttcaag    4620
tcctacggca tgaagaacgg gacgtaccac tcacggtcca gtgggtacaa gccgcaaccc    4680
ggcgacgcca tcgtgttcga ctgggaccac aggtccggtg acgaccatcc gatcgaccac    4740
gtggccatcg tgatcagctc ctcctccggc acgtcaaca ccatcggtgg caaccagggc    4800
gacccgggcc gggtccggcg gtcgagctac cagcgctcga acggcgacat cgacggctac    4860
atctcccccg tgggcgtcgg cgacggcggt ggcggtggcg gtggcgagga aagccgagt    4920
gtcaaccaca cgtcaccgg cgactcgttc acggacctgg tgggccgcaa gcccgatggc    4980
accatctggg cgtacaacaa caacatcctc cgcgacaacg gcgtcccgta cagcgtcggc    5040
cgcgagatcg gccacggctg gaacgccttc gacaccgtcc tgaccgcgga cgtgaccggc    5100
gacggctaca cggacctggt ggcacgcaag cccgacggca cgttgtggct gtacgccaac    5160
gacaccaaga cgacggcct gccctacagc tccggccgcc agatcggcac gagctggaac    5220
atcttcgaca ccatcgtcgc cgccgacctg accggtgacg gcttcgccga gctcgtcgga    5280
cgcaagcccg acggcacgct ctggatgtac gccaacaaca tcctccgcga caacggcaag    5340
ccctacagcg ccagccgcga gatcgggcac ggctggaacg tgttcgacac gctgatcgcg    5400
gccgacgtga ccggtgacgg cttcgcggag atggtggcac gcaaggcaga cgggacgttg    5460
tggatgtacg ccaacaacat cctgcgcgac aacggcatgc cgtacagctc gggccgtcag    5520
atcggcaacg gctggaacat cttcgacacg atcatcggtg cgaacgtgac aggtgacggc    5580
ttcgccgacc tcgtcggacg caaggccgac ggcacgatcc tgctgtactc caacaacatc    5640
ctccgcgaca acgccagcc gtacagcacc ggccgcaga tcgggaccag ctggaacatc    5700
ttcgacatca tcatgtgacg cgatttcccc gaaggcgcgc ccggcggttg ccgggcgcgc    5760
ctcggcgtgt gctcaccagg tgacgcatcg gtgttctgcg cgacccgatc ttcactcgcc    5820
ttcgggttca ggctcgggcg cgcggcgggc aggacgtacc ggggcgcacc ctcggcgagc    5880
tcggcaccga gaccacagga ccactgccag aaggaccgcg ggaggacatc ggcgtccacc    5940
cgcggtcaac cgagcagccg ggagagcttc atcggcgcga gctttcggta gctctcggtc    6000
agcagctcgc cgatctcggc ccagtcggcg tccggctcga cgatcatgcc cacgacatcg    6060
aaccccacg ccgcgcggaa gaacgggtgg ccgctgttga ccagcgcctc gaagtcctcc    6120
tgctgagcac ggaaagtcat caccacagcc ggttcggtga gttccgccgc gcggctgaac    6180
gtccccgtcg cgcctggctg cgccgtgaac acgtgcaaga tcgtgcgttg ccggatgcgc    6240
caccgggttc ccaccaggc cggctcctcg tagctctccg gcaggccggc acagatcctg    6300
cgcagtgact ccagcacggc agacggcacg tcggcgcgat cggtcatggt tgcctccctc    6360
acggaacgct agatcgtttc cgcgagccgg accagtccca ctggctcgac gaccacgcgg    6420
acgactccgt cgaggccact ccgtcgatcc gcggtgaggc gttcgatctg gccggatcca    6480
gagcgcgacg actcgctcag cgcttccccc ctgccgccat actcgagcct acgaggcagc    6540
```

-continued

```
gccgtcgagc tgatccacgg tgcgagcagg aaggatttcg atggggatct cactcaacgc    6600
cgccagcgtt ctcccgcagg acgcggcgga cgccacactc gtcgcgaggg tcttcgaccc    6660
gtccgccggc ggcccttcgg tcgtgacggt ccgtggcgag gaggtcgtcg acctgtcggc    6720
cctggcgtcg accgtgtcgt cgttgctcga gcggccggac gcgctggaga tcgtgaggaa    6780
tcacccgggc ggcacgtcgt ggccgctcgc ggacgttctg gctgccacga cgaacgcggc    6840
cgacggtgtg ccccggttcc tggcaccggt cgacctgcag gtgctcaagg ccgccggcgt    6900
gaccttcgtg cgcagcatgc tcgaacgggt catcgaggag cgcgccgacg gggatcccac    6960
gcgggccgag gaggttcgcg agaaggtggg cgcgatcgtc cagggccaca tctcccacct    7020
gaagccgggg tccgcggagg ccgcggaggt gaagagggtt ctgcaggccg agggcctgtg    7080
gtcgcagtac ctcgaggtcg gcatcggccc ggaccccgag atcttcacca aggccccggt    7140
gctctcggcg gtgggcctgg cgccgacat cggcgttctc gcccgctcgg cctggaacaa    7200
ccccgagccc gagctcgtcc tggtggtgga ctcgcgcgga aacccggtcg gcgcgacgct    7260
cggcaacgac gtcaacctgc gcgacttcga gggccgcagc gctctcctgc tcaccgaggc    7320
gaaggacaac aacgcctcct gcgccatcgg accgtttctc cggctgttcg acgacggttt    7380
caccctcgcg gacgccaaag ccaccgagat cgccctggac atcaccggcc ccgacggttt    7440
cgagctgcac ggcgtgaacc cggtctccga gatcagccgg gagctcgagg acctcgtgtc    7500
ccacgccttc ggcgcccacc accgctatcc cgacggcttc gtgctgttca ccggcacgat    7560
gttcgctccg accgaggacc gggaccagcc cggcgaaggg ttcacccaca agatcggcga    7620
cgtcgttcgc atctcctcgc cccgactggg cacgttgacg aacgtcgtga caccgccga    7680
ggacaccgaa gactggacgt tcggcatcac cgcgctgatg gagaacctcg ccgcccgcag    7740
cctgctgggc ccgcgcacgc gctcgtgacc caaggtcgtc gtcaccgatc cagccgaggt    7800
gaccgggggc aggagacgca aggtggtacg agcgaggagt tcagacgagg ccctcgatca    7860
ggtcgacggc gtccacgacc gcgtcgcgcg ccgcgtactc gtcccgcagc gcgccgcgt    7920
ggacccggaa gcgcggctcg tcgagaacgg cgcgcacggc ccgtctgatg tcccgttcgg    7980
acagcctgcg cttcttcagg tgaacacccg cacctgacca gctcactctg gccgcgacct    8040
cgtgcttctc ctcggtggcg gcggcgacga ccagcggcac gccgtgtgcg agcgccgtgt    8100
tgacgccgcc gtatccccg ttggtcacca tggcgtccac gtgggaagc aatgcgtgat    8160
gcgggatgaa ccgttccacc cgcacgttgg ccggcatcgg ctccagttcc agaggggcac    8220
cggtggtcgc gaccacgagc acgtcttcgg ctgccagcgc tcggatggcg gggagcagca    8280
ggcgttccgc gtcgttggcg acggtgccct gggtgacgtg gacgacgggc cggccggagt    8340
cgagctcgcc ccaccacgcc ggtggggtga agtccggcgg agcagggctc acgaacgggc    8400
cgacgaacct cacctcgggt ggcatgtcgc ctcgcgggta ctcgaaggac ggcacggtgc    8460
ccagcaggta gaggtcgggc gtgcgcatga tgttctcgaa cgcccccttg cggatgcggg    8520
gcaggccgac gcggtcgcgc accacgtccg cgtgccgccg gagatctcgc atgacgacac    8580
ggtctgtcag ctgtttgagc acggtgttgc gcagcctgcc cagcctggag ctgctgggcg    8640
gcaggcccag cccgagcggt gccgtgtcgc ggctgctgaa gacgtagatc gacgtggcga    8700
tccaggcgac ggggattccc gtgcgctcac tgacgaaacc cgcgccgaag aaggtctcgt    8760
cggtcacgag cacgtcggcc gggaagtcct ccagcagtgc cagcaggtct gtcatctggt    8820
cggccgcggg ttcgatgaag atgtccctga acccgcgat catccccgtg atcccggtca    8880
gccccgcgtg ctggggaaac gcctcctccc tcggcatgcc gccgaagtcg tgggcgtcgc    8940
```

```
gcatcggctc gtggcgggct cctgttcgtt ccactgtgga gcggaacgcc tttcccgtgt   9000
accaccgcac ctcgtgtcca cggctgacca tctcctgggc gaccggcacc atcgggttga   9060
cgtgcccgtc ccccggtgtg gtcgccacca gcactcgtgc ccccatgccg tccgacggta   9120
gccaccattc ccgccgcggc acggcagtcg cgggcaaaac cccctcgacc acgcggggtc   9180
aggcgggtcg gaaaggtcgc tggaccaccg gggaagaggc tgggaaccgc tcggggcgag   9240
cctgttcgcg tgatgtgcgg gcagcggtca cgccaggagc atggacgggc gaagcgacgt   9300
cgaactgggg gcgggatgtc acgcggacac aagaagatca ctgttctggg cgccggtgtg   9360
gcaggtctgg tggccgcgca cgagctcgag gagctcgggc acgaggtcga ggtgctcgaa   9420
ggcagcgaca ggctcggcgg ccgggtgcac acgcacaggt tcggtgaggg cggctccgtg   9480
ccgttcgtcg agctgggcgc catgcgcatt ccgaccaagc accgccacac catcgactac   9540
atcggcaagc tcggcctgac tccgaagctg aaggagttca agacgctgtt ctccgatgac   9600
ggcgcctacc acaccaccag tgcgggattc gtgcgcgtgc gcgacgcggc caaggtgctc   9660
gtggacgagt tcaggctgct gatgtccggc cgtgacctgc gcgaggagac catcctgttc   9720
ggcgcctggc tcaccgccgt cggcgacgcg atcgcgcccg ccgacttccg ggccgcgctg   9780
cgcaccgact tcaccgccga cctgctcgag gtcgtcgacc gcatcgacct cgacccgttc   9840
ctggtcggtg cggccgtga ccagttcgac ctgcacgcgt tcttcgcggc gcacccggag   9900
gtgcgcacga gctgcaccgg caagctcaac aggttcgtcg acgacatcct cgacgagacc   9960
agcccgcggc tgctgcgact cgaaggcggc atggaccagc tggtcgacgc gcttgtggaa  10020
cggatcaggg gcgacatccg cacggggcac gaggtgagtg cgatcgacgt ccgggaggac  10080
cacgtcgcgg tgaccgtcca caacggacat ggggtgaaca cgctgcggtc cgatcacgtg  10140
ctctgcacga tcccgttctc cgtgctgcgc aacctccggc tcaccggtct cagcacggac  10200
aagctggaga tcatccacga cgtcaagtac tggtcggcga ccaaggtcgc gttccgctgc  10260
cgtgagccgt tctgggagcg ggacggcatc aacggcggcg cgtcgttcgg cggggggcagg  10320 atcaggcaga cctactaccc accggtggaa ggcgacccga ccaggggcgc tgtgctgctc  10380
gcgagctaca ccatgggcga cgacgccgac gtgctgggcg ggatgcccga ggcgcaacgg  10440
cacgaagtcg tgctggacga ggtcggtcgc atgcaccccg aactgacga gccgggcatg  10500 gtcgtcgagg ccgtgagcag ggcatggggc gaggaccgct ggagcaacgg tgccggcgtc  10560
acgcggtggg gcaaggacgt cgccgcgtgc gaggaggaac gcgatcgcgc cgcacggccc  10620
gagggcaggc tgtacttcgc gggtgaacac tgctcgtcga cacggcgtg gatcgacggt  10680 gccgtcgagt cggcgctggc cgccgtgcgc gcgatcgagg cgggcgacgg acgatgagcg  10740
tcttcgacct gccgcgcctg cacttcgccg ggacggcgac gacgaggctg ccgacggggc  10800
cgcgcaacgg gctggtggac ctcagcaccc actccgtcgt catggacggc gagcggttcc  10860
ccgcgtcacg gcccgccgcc gagtaccacg cctacctcga ccgcgtcgga gcaagggca  10920 cggcgttcgc cggcaacggg tacttcgcga tcgacgccgg gatcaccgcc gtcgagcggg  10980
cagcgggcga ggtggacacc ggcgacctcc tggtaggccg ggcggtggac gtgtggggcc  11040
actacaacga gtacctcgcc acgacgttca accgggcgcg gatcttcgac gtggacccgt  11100
cgtcgagctg gacctcgacg gtcatgatcg gccagttcgg attcggcagg ctcggccgct  11160
cccacgacgt cgggtacgtg ttcaccggtg gggtgcacgg gatgcaacct ccgcgctggc  11220
acgaggacgg cagggtcctg caccagttca ccgtgcccgc cggcgaggac atgacctggt  11280
tcggcagcgc ggccgattcc cctgccgccg cacgactccg cgagctcgtc gagtcgggtg  11340
```

```
aggccgacgg gctcgtggtc cagctggccc tctccgacgc gggtcccgct ccgatgcccc    11400
acgcccagca gtggcggctg cgcggcacga tcgcaccgtg gcacgccggc gagccgcgga    11460
cctgtcccgc gggaaggttg ctgacaccgc acaacctcac cgccgatctg cgcggcgacc    11520
acgtctcgct gaacctgatc tcgttccgcc cgcccaccgg gatcagcggt ctcgaactgc    11580
gcaccgcgga cacagacagg ttcatcgcgc gagtacccgc cgacgacccg cacggcgtgg    11640
tcaccgtgcc ggcggcggaa ggcggcgacg aggcgttgtg cgtcgtcggc accaccgccg    11700
ccggcgagcg gatcgtggtg tcccgcgagc gggaggtcac ggttcacgtc gacgacgcga    11760
gtgtgttcct cgaacacccc cgcggccctg gggacagcga ccaggacgcc gagatcgcgg    11820
ttcgcacgta cgtccgcgga gagcccgccg ccgcgaccat ccacatagga cagtacttca    11880
acccgcgggc gttcccgctc gacgagcatg ccaccgccgc ctcggcgacg ccggaggacc    11940
tcgacgtcgt cgcgctctgc gtcgacggca cgcggtggtc acgacactgc gtgatcagca    12000
ccgacgagaa cggcgacggc cggtttctgc tgcgcggcgc caggccgggg gcgacacgtc    12060
tgctgctctc cgcggaaggg gcgacgccgt tcgacgggct cacggctgcc gcggcctacg    12120
acaacgacga ctcgctgggc ttgtggtcag ggctcgcgtc ggttgccgtg agagtgctgc    12180
ccgaccactg gtggatggac gacataccgc gcgacaaagt caccttcgac ctgctctacc    12240
gcgaggtctt cgcgttctac gaactgctct actcgttcat gggcgaggag gtgttcagcc    12300
tcgccgacag gttccgcgtc gagacacatc cccggctcat ctggcagatg tgcgacccgc    12360
gcaaccgcgc gaagacctac tacatgccgc cgacacgcga cctgacaggt ccgcaggcga    12420
ggttgctgct cgcctacctg cgcgcgcaga acagcgacgt cgtcgtgccc gtgatcgaac    12480
cgtcgcacac gcgtccggc acgccgatca gcacccgcac cgacctcgtc cgcgccctgc    12540
ggcacggtgt ggcgatcgaa ctggccgtga tgctgcagta cctgtacgcg gcgttctcga    12600
tccccaccca cggggcaggg caggagctcg tcagccgcgg tgactggacc cccgagcagt    12660
tgcggctgat gtgcggcgac ggcggcgaga cgaccgacgg cggcgtgcgg ggcagcctgc    12720 tggggggtcgc ccgcgaggag atgatccatt tcctggtggt caacaacgtt ctcatggccg    12780
tcggtgagcc cttccacgtg cccgaccgtcg acttcggcac gatcaacgac accctgatgg    12840
tgccgctgga cttctcgctg gaggcgctcg ggctcggcag cgtgcagcgg ttcatccaga    12900
tcgaacaacc ggaggggctg accggcgccg tgcggctggg tgacctgccc gtgcccgtcc    12960
gggaagcaga ggacttccac tacgcctcgc tgagtgagct gtacggcgac atccgcgaag    13020
gactgcaacg cgttcccggg ctgttcctcg tcgaacgggg ccgtggcggt ggcgagcacc    13080
acctgttcct gcgcgagtcg gtcaacgccg ttcatcccga ctaccagctg gaggtcgacg    13140
acctgtccag tgcgctgttc gcgatcgact tcgtcaccga acagggcgag gggcacgtgc    13200
tgacggacga ggacaccggg gaggagtcgc actacgacac cttcgtccgc gtcgccgacc    13260
tgttgatgaa ggaacgcctc accgccgcgg acacgagaag ggcccagtgg agtcccgcct    13320
acccggtggc gcgcaacccg acggtgcacg ggggcgggca gtccaaggag ctggtgacga    13380
gtcctgtcgc cagggaactc atggtcctgt tcaacaagtc ctacttcatg atgctgcaac    13440
tgatggtgca gcacttcggt ggcagtcccg acgccagcct gccgctcg aagctcatga    13500 acgcggccat cgacgtgatg acgggagtca tgcgcccgct ggcggaactg ctcgtcaccg    13560
tgccgtccgg gcgcacggg cgcaccgcag gcccgtcgtt cgagctcgac gagaagccgg    13620
cgttcatccc ccgtgcggac gtggcgcgcc gcgcgatctc gctgcgcttc ggcacctgg    13680 ccgagtccgc acgcacatgc gcgctggtgc cggacaaggt cgtccgcaac ctggatttcc    13740
```

```
tcgccgacca gttcgcaacg gaaggaccgc gatgaacgcg cccatcgaaa cagacgtgct   13800
gatcctgggc ggaggtccgg tgggcatggc gctggcgctc gacctcgccc atcgccaggt   13860
cggccacctc gtcgtggagc agaccgacgg tacgatcacc cacccgcggg tcggcaccat   13920
cggcccgcgg tccatggaac tcttccggcg ctggggtgtc gcgaagcaga tccgcaccgc   13980
cgggtggccc ggcgaccatc cgctcgacgc gcgtgggtg acgagggtgg gcggccacga   14040
ggtgtacaga atcccgctcg gcaccgcgga caccagggcg acacccgagc acacaccaga   14100
acccgacgcg atctgcccgc agcactggct cgcaccctg ctgcggagg ccgtcggcga   14160 gaggctgcgc acccgctcgc ggctggactc cttcgagcag cgcgacgacc acgtccgcgc   14220
cacgatcacc gacctccgca cgggtgccac ccgtgccgtg cacgccaggt atctggtggc   14280
gtgtgacggc gcctcctccc ccacccgcaa ggccctcggc atcgacgcgc caccgaggca   14340
caggacgcag gtgttccgca acatcctgtt ccgcgccccc gaactgcgtt cgctcctcgg   14400
cgagcgcgcc gcgttgttct tcttcctgat gctgtcctcg tcgctgcgct tccccttgcg   14460
cgcgctggac ggccgcggcc tgtacaggct cacggtcggg gtcgacgacg catcgaagtc   14520
cacaatggac tcattcgagc tggtccgccg ggccgtcgcc ttcgacacgg agatcgaggt   14580
gctctccgac agcgagtggc acctcaccca ccgggtggcc gacagcttct ccgccggccg   14640
ggtcttcctg accggggacg cggcccacac gctctcgccg tccggcggct cggcatgaa   14700 cacgggcatc ggcagcgcgg cggatctcgg ctggaagctc gccgcgacgc tgcgtgggtg   14760
ggcagggccc ggcctgctcg ccacctatga ggaagaacgc cgcctgtcg cgatcacgag   14820 cctggaagag gccaacgtca acctccgccg caccatggac cgggaactgc gccgggact   14880 gcacgacgac gggccccgcg gcgaacggat ccgcgccgcc gtggccgaga gctggagcg   14940 cagcggcgcc cgccgcgagt tcgacgcgcc cggcatccac ttcggtcaca cctaccgctc   15000
gtcgatcgtc tgcggcgagc cggagaccga ggtggccacc ggcggatggc ggccgagcgc   15060
gcgaccgggt gcccgcgcgc cacacgcgtg gctcaccccc accacgtcca ccctcgacct   15120
gttcggccgc gggttcgtcc tgctctcctt cggcaccact gacggtgtcg aggcggtcac   15180
gcgtgccttc gccgaccgtc acgtcccgct cgagacggtc acgtgtcacg ccccggagat   15240
ccacgcgctg tacgaacgcg cgcacgtgct cgtccggccg gacggccacg tcgcctggcg   15300
cggcgaccac cttccggcgg agctcggcgg gctggtggac aaggtgaggg gtgccgcgtg   15360
aagccgttcg acctcaaggc gttcaccggc gcggacctcg ccgacccgta tcccgtctac   15420
cgcgagtacc tcacgggcga ccctgtgcac cacaacggtg aggcgtggta cgtgttcggc   15480
tacgacgggg tggctcacgt gctcaccagc cgcgactacg gccgccgggg tcccggcggc   15540
agggcgacgc cgatcccgcc ctcgcacgac acgttgagcc gcatcgtcga gaactggctc   15600
gtcttcctcg acccgcctcg gcacacggcg ctgagatcgt tgctggccaa ggagttctcc   15660
ccggcggtgg tcaccggcct gcgcgagcgc gtgcggaaga tcgccggcga gctgctcgcc   15720
ggcctcggcg acgcgggcga gatcgacctc gtcgaggact cgccgccccc gctgccgatc   15780
ctggtgatct cggagctgct cggcgtgccc gcgcggctgc gctcgtggtt tcgccggtgt   15840
gccgtcgatc tgcaggaagc gagcaccgct cgcgccaccc gcaacccgg cgcactcgca   15900 cgggccgacg gcgcggcatc agaactggtc gagttcttcg gtggcgagct gggcacgcgc   15960
aagcccgacg acgaggacct cgtccgcgctg ctcgtcaacg cgcagcggcg cggtgaggcg   16020
ctgaccgacg aggagatcgt gtccacgtgc gtgcacctgc tgaccgccgg gcacgagacg   16080
accacgaacc tgatctccaa gtcggtcctc gcgctgctgg cgaatcccgc cgcagccgcg   16140
```

```
gaaccgctgg ccggactgga cgtgacaccg caggtggtcg aggagctgaa caggttcgac    16200 accccccgtgc agatggtcac tcgctgggcg caccaggaca ccgcgctcgg cggcaagccg    16260
atccggcgag gcgacaaggt ggtgctggtg ctcggttcgg ccaaccgcga cccggcggcg    16320
ttcgccgaac ccgacaggct cgacctgcgg cgggactcgc gcaggcactg cgggttcggg    16380
ctcggcatcc actactgcct cggcgccgcg ctggcgagga cggaagccga gatcgggctg    16440
tccgtgctgt tcacgaactt ccccggcctg cgcctcggcg gggaaccggt ccgctacgcc    16500
gacgacctgg tcttccacgg cccggcccgt ctgccgatgc tgacacgttg accgaatcga    16560
agagtgaggg gaccgcggtg gcagcaccga cgcctgagga agtcaggcag atgtacgacg    16620
acttcaccga cccgttcgcc aggatctggg gggagaacct gcacttcggc tactgggagg    16680
acgcgggcgc cgacgtgtcc gtcgacgacg ccacggaccg gctgaccgac gagatgatcg    16740
ccctgctcga cgtccggtca ggggatcggg tgctggacgt cggctgcggg atcggcaagc    16800
ccgccgtgcg gctcgccacg gccagggacg tcagggtgac aggcatctcg atcagcaggc    16860
cgcaggtgaa ccaggccaac cgcgagcga ccgcggccgg tctggccaac cgggtgacgt    16920
tctcgtacgc cgacgcgatg gacctgccgt tcgaggacg gtccttcgac gcggtgtggg    16980
cgctcgagtc gctgcaccac atgccggacc gcggccgcgc acttcgcgag atggcacggg    17040
tgctgcggcc gggtggcacc gtcgccatcg cggacttcgt gctgctcgcg cctgtcgaag    17100
gagcgaaaaa ggaggctgtc gacgcatttc gcgcgggtgg tggtgtgctg tcgctcggcg    17160
gcatcgacga gtacgagtcc gatgttcgcc aagccgaact cgtcgtgacg tcgacggtgg    17220
acatcagcgc tcaggcccgg ccctcactgg tgaaaaccgc cgaggcgttc gagaatgccc    17280
gctcccaggt ggaaccattc atgggagcgg aaggtctcga ccgaatgatc gcgacgttcc    17340
gcggactcgc ggaggtaccg gaggccggct acgtgctcat cggcgcgcgc aagccctgaa    17400
cctgcacact cgacacggat ggtgatccca ggatcaccat ccgtgttctt ttttgcgcaa    17460
atgacgggag tccggtgtcc gttcgacgtc cgacccgcat cactcatccg cttcccggac    17520
acgcgggttc ccgcacgccc gatcacggac acgtcatctc taacccacgc attcgcgagt    17580
tttcacgccg cgaacgagaa gagcggtggc acctgcccgg attcatggct agtgtccgtc    17640
tcgaggagcg attggggatc gcgcctgtcg attgggggat cgatgtcgtt caaccgtcta    17700 cttttcgacac acatttcgag ggcgagttca tgacccgctc ccgaaaagcc gagttcctgt    17760
cggatgtcca ccaggacaat gcgaattcct ttccgcagtg gaatccgcgt gagacgaact    17820
gcgtcgcgct tcccggcaga cccgtccggg gcagggaagc cgagctcgcc cgcatcgagc    17880
aggccctcga cgacgccgcg aacgcgcgag gcggtgtcct gctcgtcgag ggcgccaggg    17940
gcagcggcag gagccgtctg ctcgccgaga ccgcgcgcag ggcggcggaa cgcggcttcg    18000
acgtggtcag cgccgaggcg aacgaactcg ctcggctcgt gccactggcg ccgatcctcg    18060
cggcgctcgg tgagccgcag cccgtaccgg gagaggctga ccactccttc gccggactcg    18120
acgacaggtg gagcaggcag ctcgcgcacg tgcgcggcag gctcgcgcgc aggatcgtca    18180
aacggccctt ggccgtgctg ctcgacgacc tgcagtgggc ggaccggtg acgctgctgg    18240 cgttgcggat cctgcccgcg cagctcgccg gtcagcccct cctgtggatg ttgtgccggc    18300
gcaccgacga gcgggagccg tacgtcgccc agctctacga ccagctgctc gccgccgag    18360 tggccacgcc actgcggctg cagccgctca cggcgcccgc cgccgacgag atggccgccg    18420
acctgctcgg tggcgccaag cccgcacccg aggtgaacgc gctggtcggc gcggccgacg    18480 gcaacccgc cgtgctcacc gagctgatcg aggggctggt cgacgagaac gtggtcgtct    18540
```

```
gttccgatgg cacggcacgc ctcgtccacg gcaatgcgtc agcactgctg ccgcaacggt      18600
ttcgcagcct catgcgagga cggatcgacg ccctgtcgcc ctcgacggcg cgcatgctcg      18660
aggtcgccgc cgtgctcggc aggtcatggc tgcccgacga cgtcgtggag atgctcggca      18720
cgtccaccgc cgagctcctg ccctgtttcc aggaggcact ggcggcccgc ctgctcatgt      18780
ccacttcgga caccatggtg ttccggcacg acctggtctg cgcgctcgatc accgagtcga     18840 ttcctcctgc cgtgtgtgcg gcgctgcaca gacaggcggc gaggatgctc ctcgatcgcg      18900
gctcacccgt cgtctccgtg gcggtgcatc tggcgcgagg cgcacgaccg cacgacgtcg      18960
aggccgtagc cgtcctcaag aacgccgcca ccgaggtgat gacgtcatct ccgcgcaccg      19020
ccgtcgagtt cgcctcgcgt gccctcgaac tcaccgacag ggacggctcg acccggcccg      19080
cgctcaccgc cgttctcgtc gaggcgcaca cccgtgcagg ggctctcggg cgcgctgtcg      19140
cggtggccgc gaacgcggga ccggagactc ctgcccccgc cctgcaccgg tcgctgtcca      19200
ccgcgctgct gttgagggg gaggcgaggg aagcgctggc cgtgtcggag aaggcactgg       19260
ccgccgcctc tgtcacgccc gagacgcggg aagcactgga gatcaacagg ctggccgcgc      19320
tcgctgccct cgacgacgac gcgctcggtt ccgaggtgcg gcgatgcacg ggcgacagcc      19380
ccggcgtcct gaccgtgctc gccaccgcac gatggcaacg aggtgagttc gccgagggtc      19440
tccggctcgc ccgtgccgcg gccgggcag ccgaggaggg agcgccgttc ccgtggcacc       19500
tcgacccgcg catcgcgctc gccgcgtttc tcgtgcagtc acgccgtgag gacgaggcca      19560
ggcaggtcat caccgtgctg gacggtgaca tcggcaggtc gggactcgac gtgctggcct      19620
cggtccccca cctgctgatg gcgcagctcc acctcgcggc gggccgcgtg gaggaggcgg      19680
cgtcacgggc gcacgccgcg ctcgcggagc cggtgaccac gcacacgccg atcgcgcacg      19740
ccgtactcgc ggcagtcgcg ttgcgacgag gcgatctggt ggcggccgcg gagcacgcac      19800
accacctcga cggcgtgcgg cccgtgcact ggcgcgccca gacgcgctgg gtgcggaccc      19860
agctcacggc caccgcggat gccgacgccg gcttcagcct cgcgctgctc gccgaggaac      19920
ccgccgcggc ggcctggcac gtcagaacgg cactggtggc gggcgaggcc gaccgggcgg      19980
ccgctgtgct gcgcaggatc gcggccgccg accactgtcc ggcggccgac cacgcgcgcg      20040
gggtgcgcga cggcgacagg agcgcgctcg aacgggcggt ccgcgaccac gtcgacgagt      20100
gggcgcgtgc ctcggctgcc gaggatctgg gcgtgctcct gacgccggac gacaggaatg      20160
ccgccgtcga acgcctcgac caggcgctga cggcctacac cgcggccggc gccgaacgcg      20220
acgcggcgcg ggtgcggcgg cggttgcgcg gtctgggcgt gcggcgcagg cactggcgca      20280
cggccgaccg ccccgaatcg gggtgggaca gcctcaccaa cacggagctc agcgtcgcgt      20340
cgctcgtcac ccagggcctg accaacaagc aggtcgcgac ccagatgttc ctgtcgccgc      20400
acacggtcgg gttccacctc aggcagatct tccgcaagct cggcgtccac tcgcgcaccg      20460
agctgatcag gttcggcccc aacgccggga ggacgcgatg acgatcgagt tcgacagacc      20520
cggcgcccac gtcaccgcgg ccgatcaccg ggcgctgatg agcctgtttc ccaccggcgt      20580
cgccgtgatc accgcgatcg acgaggcagg caccccgcac ggcatgacgt gcacgtccct      20640
gaccagtgtc acgctcgatc caccgacgct gctcgtctgc ctgaaccggg cgagcggaac      20700
gttgcacgcg gtgcggggag gcaggttcgg ggtcaacctg ctgcacgccc gcggccgccg      20760
tgccgccgag gtcttctcca ccgccgtcca ggacaggttc ggcgaggtcc ggtgggagca      20820 ctcgacgtg acgggcatgc cgtggctcgc cgaggacgca cacgccttcg cgggctgcgt      20880
cgtgcggaag tccactgtgg tcggtgacca cgagatcgtg ctccggcgagg tgcacgaggt     20940
```

```
ggtgcgggaa cacgatctcc ccctgctgta cggaatgcgc gagttcgccg tgtggacacc   21000
ggagggatga gcgtgcacat cgagcccatc ggcaggttcc tgctcgcggt cggggtgatc   21060
gtcgccgtgt gccacctggg cgggctgctc tgccacagga tccggcagcc gccggtgatc   21120
ggcgagatcg cggcgggact gctgctcggc ccgacgctgc tcggcgccgt cgcaccgtcc   21180
ctgcaacgcg cgttgttccc ggaggaggtg ctgcaggcgg tggggatggc agcccagctc   21240
gggctcgtca ccttcatgtt cctgctgggc agcgaactcc gcgtggacca cgtgcgggc    21300 aacggcaaag tcgtctgggc cctggtggcg gggtcgatcc tgctgccctt cctggcaggc   21360
acgggtttcg cgctgctcac ccggcccgcc ttcggcacgc acaggtgag cacgaccgcg    21420 tacgcgctgt tcgtcgggct ggccatgtcg atcaccgcgc tgcccgtgct cgccaggatc   21480
ctcgccgact tccgcgccga ccagtcgttc ctgggcaccc tggccctgat ggcggcggcc   21540
gtcggcgacg cgctggcgtg ggcggcgctg acggtcatcc tcgccgtgac aggctcgggt   21600
tccacgggtg aactcgtgct gcgttcgcg ctggcgctca ccctcgtgct gctcaccgtt    21660
ttcgtcgtca agccggcact gaggacgctg ctgcaccggt tgccggtgaa cagccgggtg   21720
acggtgcccg cgctcgtcgt cggcacgacg gcgttcgccg ccacgaccga ggtgatcggt   21780
ctgcaccccg tgatcggcgc attcctgttc gggtgcgcga tgccgcgggg ttcggccgtg   21840
ctccagcggg cgagcgccca gctgcgcggg ttcacggtca gcgtgctgct gccgctgttc   21900
ttcgccggcg tggcgatgaa gacggccttc gacgccttcg gcaccgcggg caactggttg   21960
ctgttcgccg ccgcgctcgc cgtcgcgacg gtgacgaagt tcgtgggcgc gtcgagcggg   22020
gcgttgctcg caggcctgga ccgtgccagg gcgttccagc tcggtgcgtt gatgaactgc   22080
cgcggtgtca cggagctcgt cgtcgcgacg gtcgggctgc agaacggctt cgtcaacgag   22140
ttcggctaca cggtgctcgt gctcatcgca ctcgtcacga cggcactcac cggcccgctc   22200
gcacgcctcc gcgcggagga agcaccacag gagaaccacc gaattccgat gaaacacggg   22260
ggtacgtttc atgtccggca agattgacaa gatcctcatc gtcggcggcg gcaccgccgg   22320
atggatggcc gcgtcctatc tcggcaaggc cctgcagggc accgcggaca tcacactgct   22380
gcaggcaccc gacatcccga cgctcggggt cggcgaggcc acgatcccca atctgcagac   22440
ggcgttcttc gacttcctcg gaatccccga ggacgagtgg atgcgggagt gcaacgcgag   22500
ctacaaggtc gccatcaagt tcatcaactg gcgcaccgcg ggcgagggga cgtccgaggc   22560
ccgcgagctc gacggagggc ccgaccactt ctaccactcc ttcggtctgc tcaagtacca   22620
cgagcagatt ccgctgtcgc actactggtt cgaccgttcg taccggggga agaccgtcga   22680
gccgttcgac tacgcctgct acaaggaacc cgtcatcctc gacgccaaca ggtcaccgcg   22740
caggctcgac ggttccaagg tgacgaacta cgcgtggcac ttcgacgcgc acctcgtcgc   22800
cgacttcctg cgccggttcg ccaccgagaa gctcggcgtg cgccacgtcg aggaccgcgt   22860
cgagcacgtc cagcgcgacg ccaacggcaa catcgagtcg gttcgcacgg caacggggcg   22920
tgtcttcgat gccgacctct tcgtcgactc ctcgggcttc cgcgggctgc tgatcaacaa   22980
ggcgatggag gagcccttcc tcgacatgag cgatcacctg ctcaacgaca cgccgtcgc    23040 cacccaggtg ccgcacgacg acgacgcgaa cggtgtggaa ccgttcacct cggcgatcgc   23100
catgaagtcg ggctggacgt ggaagatccc gatgctcggc aggttcggca ccgggtacgt   23160
ctactcgagc cggttcgcca ccgaggacga ggcggtgcgc gagttctgcg agatgtggca   23220
cctcgacccg gagacccagc ccctcaacag gatccggttc cgggtcggcc gcaaccggca   23280
cgcgtgggtc ggcaactgcg tcagcatcgg cacgtcgtcg tgcttcgtgg aaccactgga   23340
```

```
gtcgacgggc atctacttcg tctacgccgc gctgtaccag ctggtgaagc acttccccga    23400
caagagcctc aaccccgtgc tgaccgccag gttcaaccgc gagatcgaga cgatgttcga    23460
cgacacgcgc gacttcatcc aggcgcactt ctacttctcg ccgcgcacgg acaccccgtt    23520
ctggagggcc aacaaggagc tgcgcctggc ggacggcatg caggagaaga tcgacatgta    23580
ccgcgcgggc atggcgatca acgcgcccgc gtccgacgac gcccagctct actacggcaa    23640
cttcgaggag gagttccgca acttctggaa caacagcaac tactactgcg tgctggccgg    23700
cctcggtctg gtgcccgacg caccctcacc acgcctggcg cacatgccac aggcgacgga    23760
gtcggtggac gaggtcttcg gcgccgtcaa ggaccggcag cggaacctgc tcgagaccct    23820
gccgagcctc cacgagttcc tgaggcaaca gcacggccgc tgacagacgg ctgacgacgt    23880
cccctgcgca ctcccacgac ctgaggagcg cgcagggac gttgccgcgt gatcactcgt    23940
gtggtgtcgt cgccggcact gactcgcgcc ggggcaacgc cagcgcgatc agggcgccgg    24000
ccacggcgaa aacggcggca cccaggaacg ccacctggta tccgctggac agcgcggcca    24060
cctcggagac cggcggctcc ttcgcgagct cggccgccga gtacgcaccg acagcgccg    24120 ccagcgcacc gagcccagc gcgccaccca gctgctgtgc ggtgttgatc aggcccgacg    24180
ccaggcccga ctcgttctcc gcgagtcccg cgacggcggc cgtcgtcacg gcgacgaagg    24240
tcgtgcccag gccgagaccg cgcaccagct gcccggcgac ggtggcgccg aagccgtcct    24300
cctcggtgag gcgggacagc aggacgagac cgacggccag cacgccgagg ctcaggagca    24360
acgtgaaccg catgccgatc ctggccatcg ccagcgcgc cagcgcggcg cgcccacca    24420 tcgagatcaa cgacacgggc aggaacccga gccctgtctg cagcggggtg agacccacga    24480
cgttctgcag gtgcagcgag agcaggaaga acatcgcgta cggcgcggca cccgcgaaga    24540
ggccgacgac actggcgacg gagaggttgc ggttgcggaa cgacgacagc gggacgagag    24600
gttcacgcac cttgcgctgc acgaggaaga agctcaccag cagcacgacg gcgagaccca    24660
gtgcgagcag gatcgtgacg gggtcgcccg actggccgct cacgatggcg tagaccaaca    24720
acgtcaagcc accggtgagc gtgacggcac cggcgacgtc gagcctgccc cgcgtgtcgc    24780
cgcgagcgcc ggacacgctg cggaacaccc cgagcacgac cacgacgacg ataggacgt    24840 tgatgtagaa gatccacggc cagccgggcc ccgaggtcag cacgccgccg agcaacacgc    24900
cgacggcacc accgacgccg ctgacggccc cccacatcgc gagcgcctgg ttgcgcccct    24960
taccctccgg aaacgtcgcg acgatgatcg acaacgcggc ggcggaggcg acggccgccg    25020
agagaccctg cacggcgcgg gccgcgacca gcacaccggc caccggtgcg agcgcggcgg    25080
ccagggaggc ggcaccgaac aggcagatgc ccgagacgaa cacgaggcgg cggccgatca    25140
ggtcggccat gcgcccgccg agcatgagga agccgccgaa ggtgagcgtg taggcgttga    25200
ccacccactg caggcctgtc tggtccatgc cgagctcacg gcccatcgag ggtagagcga    25260
tgttcacgat cgaggcatcc agcacgatca tcagctgggt gatcacgagg aatggcaacg    25320
ccgaccgggc gcggtcgcgc tcgtctgccg tcatgctctt gctccttggt cctggcacga    25380
agtcgcgcgg ccacgttagt atgaaagcct gacatacaca aatggaggac ccggaaccgt    25440
ggcagctgaa cctgacgcac ggccactgga cggaccggcg ggcggagacg ccggtctgcc    25500
ctacctgatc gcacgtgtcg aacacgcgat agccggacgc gccaacctcg cgctcgggc    25560 gctgggctc accatccggc agatgggggc gttggacatc gtgtcccgca accccggcat    25620
cagcagcgtc gagctcgccc ggcaggtgct cgtgacccgc cagacgatga actccatgat    25680
c                                                                    25681
```

```
<210> SEQ ID NO 2
<211> LENGTH: 44
<212> TYPE: PRT
<213> ORGANISM: Artificial
<220> FEATURE:
<223> OTHER INFORMATION: OrfD13, incomplete

<400> SEQUENCE: 2
```

Ile Phe Thr Tyr Ala Asp His Asn Gly Arg His Ile Arg Phe Gly Val
1               5                   10                  15

Asp Phe Tyr Cys Gly Gly Thr Ala Ser Leu Ala Glu Pro Glu Val Ser
            20                  25                  30

Thr Arg His Asp Gly Arg Thr Pro Ile Ser Arg Gly
        35                  40

```
<210> SEQ ID NO 3
<211> LENGTH: 1003
<212> TYPE: PRT
<213> ORGANISM: Artificial
<220> FEATURE:
<223> OTHER INFORMATION: OrfR5

<400> SEQUENCE: 3
```

Met Glu Phe Arg Leu Leu Gly Pro Val Glu Ala Leu Val Glu Gly Arg
1               5                   10                  15

Ser Val Pro Leu Gly Gly Leu Lys Pro Gln Val Leu Leu Ala Ala Leu
            20                  25                  30

Val Leu Glu Arg Gly Arg Val Val Pro Ala Asn Arg Leu Val Glu Leu
            35                  40                  45

Leu Trp Gly Glu Glu Pro Pro Val Ser Ala Arg Ser Leu Ile Gln Thr
50                  55                  60

Tyr Val Ser Lys Leu Arg Lys Ala Phe Ala Asp Leu Gly Ala Pro Asp
65                  70                  75                  80

Val Ile Val Ser Lys Thr Gln Gly Tyr Leu Val Arg Leu Asp Asp Ala
                85                  90                  95

Arg Val Asp Ala Asp Glu Leu Ala Gly Leu Leu Gly Lys Ala Arg Gln
            100                 105                 110

Gln Ser Gln Val His Gly His Glu Pro Ala Ala Arg Leu Leu Gly Glu
        115                 120                 125

Ala Val Ala Leu Ser Arg Gly Pro Ala Leu Ser Gly Leu Arg Asp Thr
130                 135                 140

Leu Leu Ser Gly Glu Ala Arg Arg Leu Asp Glu Leu Leu Val Thr Val
145                 150                 155                 160

Gln Glu Glu Arg Phe Ala Ala Glu Leu Gly Leu Gly Arg Phe Asp His
                165                 170                 175

Leu Ala Glu Leu Thr Ala Ala Val Ala Arg Gln Pro Val Asn Glu Arg
            180                 185                 190

Leu Arg Gly Gln Leu Met Val Thr Leu Tyr Arg Leu Gly Arg Gln Ala
        195                 200                 205

Asp Ala Leu Ala Cys Tyr Arg Glu Gly Arg Asp Ala Leu Val Asp Glu
210                 215                 220

Leu Gly Val Glu Pro Gly Ala Glu Leu Gly Thr Ile His Ser Ala Ile
225                 230                 235                 240

Leu Arg Gly Thr Leu Glu Leu Val Pro Ala Asp Ala Ala Pro Val Ala
                245                 250                 255

Arg Thr Ala Phe Ala Ala Val Pro Ala Gln Leu Pro Ala Thr Leu Ala
            260                 265                 270

```
Asp Phe Thr Gly Arg Val Arg Glu Leu Gly Glu Leu Val Ala Ala Leu
        275                 280                 285

Cys Gly Glu Thr Ser Ala Val Gln Ile Val Ala Gly Pro Gly Gly Cys
        290                 295                 300

Gly Lys Ser Ala Leu Thr Val Arg Ala Ala His Glu Ala Ala Arg Ser
305                 310                 315                 320

Phe Pro Asp Gly Gln Leu Tyr Ala Glu Leu Arg Gly Thr Ser Gly Leu
                325                 330                 335

Pro Ala Thr Ala Gly Glu Val Leu Gly Arg Phe Leu Thr Ala Leu Gly
                340                 345                 350

Met Asp Pro Gly Gln Leu Pro Glu Ser Ala Gln Glu Arg Gln Glu Leu
            355                 360                 365

Tyr Arg Thr Ser Leu Ala Gly Arg Val Leu Val Leu Asp Asp
        370                 375                 380

Ala Ala Ser Glu Glu Gln Val Arg Pro Leu Leu Pro Gly Ala Ala Gly
385                 390                 395                 400

Cys Ala Val Leu Ile Ser Ser Arg Asp Arg Leu Ala Gly Leu Ala Gly
                405                 410                 415

Ala Leu Phe Thr Glu Leu Asp Leu Val Thr Pro Gly Glu Ala Tyr Asp
            420                 425                 430

Met Leu Ala Arg Ile Val Gly Glu Ala Arg Leu Ala Glu Asn Val Asp
            435                 440                 445

Ser Ala His Arg Ile Val Asp Ala Cys Gly Arg Leu Pro Leu Ala Leu
        450                 455                 460

Arg Ile Ala Gly Ala Arg Leu Ala Ser Arg Arg Gln Leu Pro Leu Arg
465                 470                 475                 480

Val Leu Ala Asp Arg Leu Thr Asp Glu Arg Arg Leu Asn Glu Leu
                485                 490                 495

Ser Ala Gly Asp Leu Ala Val Arg Ser Ser Ile Ala Leu Ser Cys Arg
            500                 505                 510

Ala Leu Asp Asp Gln Ala Arg Thr Ala Leu Gly Arg Met Gly His Leu
            515                 520                 525

Gly Leu Pro Asp Phe Ser Thr Trp Val Val Ser Trp Leu Leu Glu Thr
        530                 535                 540

Ser Glu Ala Asp Ala Glu Lys Val Leu Glu Val Leu Val Asp Ala Gln
545                 550                 555                 560

Leu Ala Thr Leu Ser Gly Ala Asp Ala Gly Val Leu Arg Tyr Arg
                565                 570                 575

Leu His Asp Leu Val Arg Leu Tyr Ala Arg Glu Arg Ala Glu Ala Asp
            580                 585                 590

Glu Pro Asp Glu Leu Thr Ala Ser Ile Ala Arg Val Leu Asp Gly Trp
        595                 600                 605

Ile Ala Leu Leu Ser Arg Thr Ala Val Asn Ser Pro Pro Ala Glu Ser
        610                 615                 620

Thr Trp Arg Pro Ala Ala Gly His Arg Glu Pro Asp Gly Val Thr Ala
625                 630                 635                 640

Met Ala Glu Arg Leu Ser Asp Asp Leu Asp Ala Trp Leu Arg Gly Glu
                645                 650                 655

Glu Pro Ala Leu Ala Val Ala Val Glu Arg Ala Ala Thr Gly Leu
                660                 665                 670

His Arg His Val Cys Asp Phe Val Ser Ala His Thr Ala Ile Glu Gln
        675                 680                 685

Val Thr Asn Ser Tyr Asp Leu Arg Asp Arg Ile Ile Gly Val Ala Met
```

```
                690             695             700
Thr Ser Val Gln His Val Gly Asp Pro Gly Leu Ala Ala Asp Val Leu
705                 710                 715                 720

Ala Lys Leu Ala Arg Leu Arg Phe Ser Gln Asp Arg Phe Ala Glu Ala
                725                 730                 735

Arg Gln Leu Phe Gly Glu Ala Leu Gly Arg Tyr Arg Asp Leu His Asp
            740                 745                 750

Val Arg Gly Gln Ala Ala Ala Leu Ala Gly Met Gly Leu Ala Cys Arg
        755                 760                 765

Glu Pro Gly His Leu Thr Glu Ala Val His Phe Leu Ser Gln Ala Ala
770                 775                 780

Thr Leu Ser Gln Ala Leu Asp Asp Gln Val Gly Ile Gly His Val Leu
785                 790                 795                 800

Arg Ile Arg Gly Ser Val Arg Leu Glu Leu Gly Glu Tyr Asp Glu Ala
                805                 810                 815

Arg Thr Asp Leu Glu Gln Ser Leu Ala Ala Tyr Arg Arg Ala Gly Ser
            820                 825                 830

Arg Arg Gly Ile Ala Leu Ser Leu Arg Ser Leu Gly Leu Tyr His Arg
        835                 840                 845

Ala Arg Gly Asp Tyr Glu Thr Ser Met Ala Val Cys Ala Asp Ala Ala
850                 855                 860

Thr Ile Phe Ala Glu Leu Gly Asp Asp Leu Met His Ser Tyr Ala Val
865                 870                 875                 880

Arg Ala His Ala Lys Ala Gln Met Arg Ser Gly His Ser Ala Glu Ala
                885                 890                 895

Leu Pro Arg Leu Glu Met Ala Leu Ala Thr Val Arg Ala Lys Asp Asp
            900                 905                 910

Arg Trp Gly Gln Ala Ile Thr Leu Arg Val Leu Gly Gln Leu His Leu
        915                 920                 925

Ala Glu Gly Arg Leu Asp Leu Ala Gln Asp Cys Leu Asp Ala Ala Met
930                 935                 940

Ser Ile Trp Asp Ala Thr Glu Ala Pro Leu Trp Arg Ala Arg Thr Glu
945                 950                 955                 960

Tyr Asp Leu Ala Leu Leu His Arg Ser Arg Gly Asp Thr Gln Ala Ala
                965                 970                 975

Asp Ala Ala Phe Thr His Ala Arg Ser Val Phe Arg Ala Arg Gly Ala
            980                 985                 990

Arg Glu Tyr Ser Glu Tyr Ala Glu   Leu Pro Val
        995                 1000

<210> SEQ ID NO 4
<211> LENGTH: 210
<212> TYPE: PRT
<213> ORGANISM: ARTIFICIAL
<220> FEATURE:
<223> OTHER INFORMATION: OrfR4

<400> SEQUENCE: 4

Met Val Trp Leu Ser Asp Pro Ala Val Ala Ala Ile Pro Val Arg Glu
1               5                   10                  15

Arg Gly Glu Pro Leu Val Asp Leu Arg Thr Val Ala Ala Leu Arg Leu
            20                  25                  30

Asp Ser Arg Leu Ala Asp Glu Glu Gly Leu Tyr Ala Gln Leu Arg Ile
        35                  40                  45

Gly Val Val Asp Arg Leu Val Thr Ala Gln Thr Leu Leu Pro Pro Glu
    50                  55                  60
```

```
Leu Arg Leu Leu Ile Val Glu Gly Tyr Arg Pro His Ala Val Gln Ile
 65                  70                  75                  80

Ala Ser Phe Glu Ser Ala Val Ala Glu Ser Arg Ala Arg Ser Pro Arg
                 85                  90                  95

Ala Ala Glu Ser Val Leu Arg Arg Ala Ser Val Arg Ser Ser Pro
            100                 105                 110

Pro Glu Val Ala Pro His Val Ala Gly Ala Ala Val Asp Leu Ser Leu
            115                 120                 125

Cys Thr Val Asp Glu Ile Glu Leu Asp Leu Gly Thr Ala Val Asn Asp
    130                 135                 140

Thr Ala Thr Glu Arg Ser His Thr Glu Asp Pro Thr Val Asp Ala Thr
145                 150                 155                 160

Ala Arg Arg His Arg Ala Val Leu Ala Arg Ala Leu Arg Gly Ala Gly
                165                 170                 175

Leu Val Asn Tyr Pro Ser Ala Trp Trp His Trp Ser Tyr Gly Asp Arg
            180                 185                 190

Tyr Trp Ala Tyr Leu Thr Gly Ser Ser Gln Ala Val Tyr Gly Pro Ile
            195                 200                 205

Leu Pro
    210

<210> SEQ ID NO 5
<211> LENGTH: 438
<212> TYPE: PRT
<213> ORGANISM: ARTIFICIAL
<220> FEATURE:
<223> OTHER INFORMATION: OrfD1

<400> SEQUENCE: 5

Met Ala Gly Thr Val Leu Met Ala Pro Pro Ala Ser Ala Ala Pro Ser
  1               5                  10                  15

Arg Asp Arg Ile Val Lys Ala Ala Asp Glu Val Gly Glu Gly Ala
             20                  25                  30

Cys Ser Pro Gly Tyr Phe Asn Ser Cys Gly Met Ala Trp Cys Ala Glu
             35                  40                  45

Phe Ala Arg Trp Val Trp Asn Glu Gly Gly Val Ser Asp Leu Lys Gly
 50                  55                  60

Leu Asp Gly Trp Ala Gln Ser Phe Lys Ser Tyr Gly Met Lys Asn Gly
 65                  70                  75                  80

Thr Tyr His Ser Arg Ser Ser Gly Tyr Lys Pro Gln Pro Gly Asp Ala
                 85                  90                  95

Ile Val Phe Asp Trp Asp His Arg Ser Gly Asp Asp His Pro Ile Asp
            100                 105                 110

His Val Ala Ile Val Ile Ser Ser Ser Gly Thr Val Asn Thr Ile
            115                 120                 125

Gly Gly Asn Gln Gly Asp Pro Gly Arg Val Arg Arg Ser Ser Tyr Gln
            130                 135                 140

Arg Ser Asn Gly Asp Ile Asp Gly Tyr Ile Ser Pro Val Gly Val Gly
145                 150                 155                 160

Asp Gly Gly Gly Gly Gly Gly Glu Glu Lys Pro Ser Val Asn His
                165                 170                 175

Ser Val Thr Gly Asp Ser Phe Thr Asp Leu Val Gly Arg Lys Pro Asp
            180                 185                 190

Gly Thr Ile Trp Ala Tyr Asn Asn Asn Ile Leu Arg Asp Asn Gly Val
            195                 200                 205
```

Pro Tyr Ser Val Gly Arg Glu Ile Gly His Gly Trp Asn Ala Phe Asp
                210                 215                 220

Thr Val Leu Thr Ala Asp Val Thr Gly Asp Gly Tyr Thr Asp Leu Val
225                 230                 235                 240

Ala Arg Lys Pro Asp Gly Thr Leu Trp Leu Tyr Ala Asn Asp Thr Lys
                245                 250                 255

Asn Asp Gly Leu Pro Tyr Ser Ser Gly Arg Gln Ile Gly Thr Ser Trp
                260                 265                 270

Asn Ile Phe Asp Thr Ile Val Ala Ala Asp Leu Thr Gly Asp Gly Phe
                275                 280                 285

Ala Glu Leu Val Gly Arg Lys Pro Asp Gly Thr Leu Trp Met Tyr Ala
                290                 295                 300

Asn Asn Ile Leu Arg Asp Asn Gly Lys Pro Tyr Ser Ala Ser Arg Glu
305                 310                 315                 320

Ile Gly His Gly Trp Asn Val Phe Asp Thr Leu Ile Ala Ala Asp Val
                325                 330                 335

Thr Gly Asp Gly Phe Ala Glu Met Val Ala Arg Lys Ala Asp Gly Thr
                340                 345                 350

Leu Trp Met Tyr Ala Asn Asn Ile Leu Arg Asp Asn Gly Met Pro Tyr
                355                 360                 365

Ser Ser Gly Arg Gln Ile Gly Asn Gly Trp Asn Ile Phe Asp Thr Ile
370                 375                 380

Ile Gly Ala Asn Val Thr Gly Asp Gly Phe Ala Asp Leu Val Gly Arg
385                 390                 395                 400

Lys Ala Asp Gly Thr Ile Leu Leu Tyr Ser Asn Asn Ile Leu Arg Asp
                405                 410                 415

Asn Gly Gln Pro Tyr Ser Thr Gly Arg Gln Ile Gly Thr Ser Trp Asn
                420                 425                 430

Ile Phe Asp Ile Ile Met
                435

<210> SEQ ID NO 6
<211> LENGTH: 133
<212> TYPE: PRT
<213> ORGANISM: ARTIFICIAL
<220> FEATURE:
<223> OTHER INFORMATION: OrfR3

<400> SEQUENCE: 6

Met Thr Asp Arg Ala Asp Val Pro Ser Ala Val Leu Glu Ser Leu Arg
1               5                   10                  15

Arg Ile Cys Ala Gly Leu Pro Glu Ser Tyr Glu Glu Pro Ala Trp Val
                20                  25                  30

Gly Thr Arg Trp Arg Ile Arg Gln Arg Thr Ile Leu His Val Phe Thr
                35                  40                  45

Ala Gln Pro Gly Ala Thr Gly Thr Phe Ser Arg Ala Ala Glu Leu Thr
50                  55                  60

Glu Pro Ala Val Val Met Thr Phe Arg Ala Gln Gln Glu Asp Phe Glu
65                  70                  75                  80

Ala Leu Val Asn Ser Gly His Pro Phe Phe Arg Ala Ala Trp Gly Phe
                85                  90                  95

Asp Val Val Gly Met Ile Val Glu Pro Asp Ala Asp Trp Ala Glu Ile
                100                 105                 110

Gly Glu Leu Leu Thr Glu Ser Tyr Arg Lys Leu Ala Pro Met Lys Leu
                115                 120                 125

Ser Arg Leu Leu Gly

130

<210> SEQ ID NO 7
<211> LENGTH: 395
<212> TYPE: PRT
<213> ORGANISM: ARITFICIAL

<400> SEQUENCE: 7

Met Gly Ile Ser Leu Asn Ala Ala Ser Val Leu Pro Gln Asp Ala Ala
1               5                   10                  15

Asp Ala Thr Leu Val Ala Arg Val Phe Asp Pro Ser Ala Gly Gly Pro
            20                  25                  30

Ser Val Val Thr Val Arg Gly Glu Glu Val Val Asp Leu Ser Ala Leu
        35                  40                  45

Ala Ser Thr Val Ser Ser Leu Leu Glu Arg Pro Asp Ala Leu Glu Ile
    50                  55                  60

Val Arg Asn His Pro Gly Gly Thr Ser Trp Pro Leu Ala Asp Val Leu
65                  70                  75                  80

Ala Ala Thr Thr Asn Ala Ala Asp Gly Val Pro Arg Phe Leu Ala Pro
                85                  90                  95

Val Asp Leu Gln Val Leu Lys Ala Ala Gly Val Thr Phe Val Arg Ser
            100                 105                 110

Met Leu Glu Arg Val Ile Glu Glu Arg Ala Asp Gly Asp Pro Thr Arg
        115                 120                 125

Ala Glu Glu Val Arg Glu Lys Val Gly Ala Ile Val Gln Gly His Ile
    130                 135                 140

Ser His Leu Lys Pro Gly Ser Ala Glu Ala Ala Glu Val Lys Arg Val
145                 150                 155                 160

Leu Gln Ala Glu Gly Leu Trp Ser Gln Tyr Leu Glu Val Gly Ile Gly
                165                 170                 175

Pro Asp Pro Glu Ile Phe Thr Lys Ala Pro Val Leu Ser Ala Val Gly
            180                 185                 190

Leu Gly Ala Asp Ile Gly Val Leu Ala Arg Ser Ala Trp Asn Asn Pro
        195                 200                 205

Glu Pro Glu Leu Val Leu Val Asp Ser Arg Gly Asn Pro Val Gly
    210                 215                 220

Ala Thr Leu Gly Asn Asp Val Asn Leu Arg Asp Phe Glu Gly Arg Ser
225                 230                 235                 240

Ala Leu Leu Leu Thr Glu Ala Lys Asp Asn Asn Ala Ser Cys Ala Ile
                245                 250                 255

Gly Pro Phe Leu Arg Leu Phe Asp Asp Gly Phe Thr Leu Ala Asp Ala
            260                 265                 270

Lys Ala Thr Glu Ile Ala Leu Asp Ile Thr Gly Pro Asp Gly Phe Glu
        275                 280                 285

Leu His Gly Val Asn Pro Val Ser Glu Ile Ser Arg Glu Leu Glu Asp
    290                 295                 300

Leu Val Ser His Ala Phe Gly Ala His His Arg Tyr Pro Asp Gly Phe
305                 310                 315                 320

Val Leu Phe Thr Gly Thr Met Phe Ala Pro Thr Glu Asp Arg Asp Gln
                325                 330                 335

Pro Gly Glu Gly Phe Thr His Lys Ile Gly Asp Val Val Arg Ile Ser
            340                 345                 350

Ser Pro Arg Leu Gly Thr Leu Thr Asn Val Val Asn Thr Ala Glu Asp
        355                 360                 365

Thr Glu Asp Trp Thr Phe Gly Ile Thr Ala Leu Met Glu Asn Leu Ala

```
                370             375             380
Ala Arg Ser Leu Leu Gly Pro Arg Thr Arg Ser
385                 390                 395

<210> SEQ ID NO 8
<211> LENGTH: 421
<212> TYPE: PRT
<213> ORGANISM: ARTIFICIAL
<220> FEATURE:
<223> OTHER INFORMATION: OrfR2

<400> SEQUENCE: 8

Met Gly Ala Arg Val Leu Val Ala Thr Thr Pro Gly Asp Gly His Val
1               5                   10                  15

Asn Pro Met Val Pro Val Ala Gln Glu Met Val Ser Arg Gly His Glu
            20                  25                  30

Val Arg Trp Tyr Thr Gly Lys Ala Phe Arg Ser Thr Val Glu Arg Thr
        35                  40                  45

Gly Ala Arg His Glu Pro Met Arg Asp Ala His Asp Phe Gly Gly Met
    50                  55                  60

Pro Arg Glu Glu Ala Phe Pro Gln His Ala Gly Leu Thr Gly Ile Thr
65                  70                  75                  80

Gly Met Ile Ala Gly Phe Arg Asp Ile Phe Ile Glu Pro Ala Ala Asp
                85                  90                  95

Gln Met Thr Asp Leu Leu Ala Leu Leu Glu Asp Phe Pro Ala Asp Val
            100                 105                 110

Leu Val Thr Asp Glu Thr Phe Phe Gly Ala Gly Phe Val Ser Glu Arg
        115                 120                 125

Thr Gly Ile Pro Val Ala Trp Ile Ala Thr Ser Ile Tyr Val Phe Ser
    130                 135                 140

Ser Arg Asp Thr Ala Pro Leu Gly Leu Gly Leu Pro Pro Ser Ser Ser
145                 150                 155                 160

Arg Leu Gly Arg Leu Arg Asn Thr Val Leu Lys Gln Leu Thr Asp Arg
                165                 170                 175

Val Val Met Arg Asp Leu Arg Arg His Ala Asp Val Val Arg Asp Arg
            180                 185                 190

Val Gly Leu Pro Arg Ile Arg Lys Gly Ala Phe Glu Asn Ile Met Arg
        195                 200                 205

Thr Pro Asp Leu Tyr Leu Leu Gly Thr Val Pro Ser Phe Glu Tyr Pro
    210                 215                 220

Arg Gly Asp Met Pro Pro Glu Val Arg Phe Val Gly Pro Phe Val Ser
225                 230                 235                 240

Pro Ala Pro Pro Asp Phe Thr Pro Pro Ala Trp Trp Gly Glu Leu Asp
                245                 250                 255

Ser Gly Arg Pro Val Val His Val Thr Gln Gly Thr Val Ala Asn Asp
            260                 265                 270

Ala Glu Arg Leu Leu Leu Pro Ala Ile Arg Ala Leu Ala Ala Glu Asp
        275                 280                 285

Val Leu Val Val Ala Thr Thr Gly Ala Pro Leu Glu Leu Glu Pro Met
    290                 295                 300

Pro Ala Asn Val Arg Val Glu Arg Phe Ile Pro His His Ala Leu Leu
305                 310                 315                 320

Pro His Val Asp Ala Met Val Thr Asn Gly Gly Tyr Gly Gly Val Asn
                325                 330                 335

Thr Ala Leu Ala His Gly Val Pro Leu Val Val Ala Ala Ala Thr Glu
            340                 345                 350
```

```
Glu Lys His Glu Val Ala Ala Arg Val Ser Trp Ser Gly Ala Gly Val
            355                 360                 365

His Leu Lys Lys Arg Arg Leu Ser Glu Arg Asp Ile Arg Arg Ala Val
        370                 375                 380

Arg Ala Val Leu Asp Glu Pro Arg Phe Arg Val His Ala Ala Arg Leu
385                 390                 395                 400

Arg Asp Glu Tyr Ala Ala Arg Asp Ala Val Asp Ala Val Asp Leu
                405                 410                 415

Ile Glu Gly Leu Val
            420

<210> SEQ ID NO 9
<211> LENGTH: 473
<212> TYPE: PRT
<213> ORGANISM: ARTIFICIAL
<220> FEATURE:
<223> OTHER INFORMATION: OrfD3

<400> SEQUENCE: 9

Met Ser Arg Gly His Lys Lys Ile Thr Val Leu Gly Ala Gly Val Ala
1               5                   10                  15

Gly Leu Val Ala Ala His Glu Leu Glu Glu Leu Gly His Glu Val Glu
            20                  25                  30

Val Leu Glu Gly Ser Asp Arg Leu Gly Gly Arg Val His Thr His Arg
        35                  40                  45

Phe Gly Glu Gly Gly Ser Val Pro Phe Val Glu Leu Gly Ala Met Arg
    50                  55                  60

Ile Pro Thr Lys His Arg His Thr Ile Asp Tyr Ile Gly Lys Leu Gly
65                  70                  75                  80

Leu Thr Pro Lys Leu Lys Glu Phe Lys Thr Leu Phe Ser Asp Asp Gly
                85                  90                  95

Ala Tyr His Thr Thr Ser Ala Gly Phe Val Arg Val Arg Asp Ala Ala
            100                 105                 110

Lys Val Leu Val Asp Glu Phe Arg Leu Leu Met Ser Gly Arg Asp Leu
        115                 120                 125

Arg Glu Glu Thr Ile Leu Phe Gly Ala Trp Leu Thr Ala Val Gly Asp
    130                 135                 140

Ala Ile Ala Pro Ala Asp Phe Arg Ala Ala Leu Arg Thr Asp Phe Thr
145                 150                 155                 160

Ala Asp Leu Leu Glu Val Val Asp Arg Ile Asp Leu Asp Pro Phe Leu
                165                 170                 175

Val Gly Ala Ala Arg Asp Gln Phe Asp Leu His Ala Phe Phe Ala Ala
            180                 185                 190

His Pro Glu Val Arg Thr Ser Cys Thr Gly Lys Leu Asn Arg Phe Val
        195                 200                 205

Asp Asp Ile Leu Asp Glu Thr Ser Pro Arg Leu Arg Leu Glu Gly
    210                 215                 220

Gly Met Asp Gln Leu Val Asp Ala Leu Val Glu Arg Ile Arg Gly Asp
225                 230                 235                 240

Ile Arg Thr Gly His Glu Val Ser Ala Ile Asp Val Arg Glu Asp His
                245                 250                 255

Val Ala Val Thr Val His Asn Gly His Gly Val Asn Thr Leu Arg Ser
            260                 265                 270

Asp His Val Leu Cys Thr Ile Pro Phe Ser Val Leu Arg Asn Leu Arg
        275                 280                 285
```

```
Leu Thr Gly Leu Ser Thr Asp Lys Leu Glu Ile Ile His Asp Val Lys
            290                 295                 300

Tyr Trp Ser Ala Thr Lys Val Ala Phe Arg Cys Arg Glu Pro Phe Trp
305                 310                 315                 320

Glu Arg Asp Gly Ile Asn Gly Gly Ala Ser Phe Gly Gly Gly Arg Ile
                325                 330                 335

Arg Gln Thr Tyr Tyr Pro Pro Val Glu Gly Asp Pro Thr Arg Gly Ala
            340                 345                 350

Val Leu Leu Ala Ser Tyr Thr Met Gly Asp Asp Ala Asp Val Leu Gly
            355                 360                 365

Gly Met Pro Glu Ala Gln Arg His Glu Val Val Leu Asp Glu Val Gly
    370                 375                 380

Arg Met His Pro Glu Leu His Glu Pro Gly Met Val Val Glu Ala Val
385                 390                 395                 400

Ser Arg Ala Trp Gly Glu Asp Arg Trp Ser Asn Gly Ala Gly Val Thr
                405                 410                 415

Arg Trp Gly Lys Asp Val Ala Ala Cys Glu Glu Arg Asp Arg Ala
                420                 425                 430

Ala Arg Pro Glu Gly Arg Leu Tyr Phe Ala Gly Glu His Cys Ser Ser
            435                 440                 445

Thr Thr Ala Trp Ile Asp Gly Ala Val Glu Ser Ala Leu Ala Ala Val
    450                 455                 460

Arg Ala Ile Glu Ala Gly Asp Gly Arg
465                 470

<210> SEQ ID NO 10
<211> LENGTH: 1013
<212> TYPE: PRT
<213> ORGANISM: ARTIFICIAL
<220> FEATURE:
<223> OTHER INFORMATION: OrfD4

<400> SEQUENCE: 10

Met Ser Val Phe Asp Leu Pro Arg Leu His Phe Ala Gly Thr Ala Thr
1               5                   10                  15

Thr Arg Leu Pro Thr Gly Pro Arg Asn Gly Leu Val Asp Leu Ser Thr
            20                  25                  30

His Ser Val Val Met Asp Gly Glu Arg Phe Pro Ala Ser Arg Pro Ala
        35                  40                  45

Ala Glu Tyr His Ala Tyr Leu Asp Arg Val Gly Gly Lys Gly Thr Ala
    50                  55                  60

Phe Ala Gly Asn Gly Tyr Phe Ala Ile Asp Ala Gly Ile Thr Ala Val
65                  70                  75                  80

Glu Arg Ala Ala Gly Glu Val Asp Thr Gly Asp Leu Leu Val Gly Arg
                85                  90                  95

Ala Val Asp Val Trp Gly His Tyr Asn Glu Tyr Leu Ala Thr Thr Phe
            100                 105                 110

Asn Arg Ala Arg Ile Phe Asp Val Asp Pro Ser Ser Ser Trp Thr Ser
        115                 120                 125

Thr Val Met Ile Gly Gln Phe Gly Phe Gly Arg Leu Gly Arg Ser His
    130                 135                 140

Asp Val Gly Tyr Val Phe Thr Gly Gly Val His Gly Met Gln Pro Pro
145                 150                 155                 160

Arg Trp His Glu Asp Gly Arg Val Leu His Gln Phe Thr Val Pro Ala
                165                 170                 175

Gly Glu Asp Met Thr Trp Phe Gly Ser Ala Ala Asp Ser Pro Ala Ala
```

```
                180             185             190
Ala Arg Leu Arg Glu Leu Val Glu Ser Gly Glu Ala Asp Gly Leu Val
            195                 200                 205
Val Gln Leu Ala Leu Ser Asp Ala Gly Pro Ala Pro Met Pro His Ala
            210                 215                 220
Gln Gln Trp Arg Leu Arg Gly Thr Ile Ala Pro Trp His Ala Gly Glu
225                 230                 235                 240
Pro Arg Thr Cys Pro Ala Gly Arg Leu Leu Thr Pro His Asn Leu Thr
            245                 250                 255
Ala Asp Leu Arg Gly Asp His Val Ser Leu Asn Leu Ile Ser Phe Arg
            260                 265                 270
Pro Pro Thr Gly Ile Ser Gly Leu Glu Leu Arg Thr Ala Asp Thr Asp
            275                 280                 285
Arg Phe Ile Ala Arg Val Pro Ala Asp Asp Pro His Gly Val Val Thr
            290                 295                 300
Val Pro Ala Ala Glu Gly Gly Asp Glu Ala Leu Cys Val Val Gly Thr
305                 310                 315                 320
Thr Ala Ala Gly Glu Arg Ile Val Val Ser Arg Glu Arg Glu Val Thr
            325                 330                 335
Val His Val Asp Asp Ala Ser Val Phe Leu Glu His Pro Arg Gly Pro
            340                 345                 350
Gly Asp Ser Asp Gln Asp Ala Glu Ile Ala Val Arg Thr Tyr Val Arg
            355                 360                 365
Gly Glu Pro Ala Ala Thr Ile His Ile Gly Gln Tyr Phe Asn Pro
            370                 375                 380
Arg Ala Phe Pro Leu Asp Glu His Ala Thr Ala Ser Ala Thr Pro
385                 390                 395                 400
Glu Asp Leu Asp Val Val Ala Leu Cys Val Asp Gly Thr Arg Trp Ser
            405                 410                 415
Arg His Cys Val Ile Ser Thr Asp Glu Asn Gly Asp Gly Arg Phe Leu
            420                 425                 430
Leu Arg Gly Ala Arg Pro Gly Ala Thr Arg Leu Leu Leu Ser Ala Glu
            435                 440                 445
Gly Ala Thr Pro Phe Asp Gly Leu Thr Ala Ala Ala Tyr Asp Asn
            450                 455                 460
Asp Asp Ser Leu Gly Leu Trp Ser Gly Leu Ala Ser Val Ala Val Arg
465                 470                 475                 480
Val Leu Pro Asp His Trp Trp Met Asp Ile Pro Arg Asp Lys Val
            485                 490                 495
Thr Phe Asp Leu Leu Tyr Arg Glu Val Phe Ala Phe Tyr Glu Leu Leu
            500                 505                 510
Tyr Ser Phe Met Gly Glu Glu Val Phe Ser Leu Ala Asp Arg Phe Arg
            515                 520                 525
Val Glu Thr His Pro Arg Leu Ile Trp Gln Met Cys Asp Pro Arg Asn
            530                 535                 540
Arg Ala Lys Thr Tyr Tyr Met Pro Pro Thr Arg Asp Leu Thr Gly Pro
545                 550                 555                 560
Gln Ala Arg Leu Leu Leu Ala Tyr Leu Arg Ala Gln Asn Ser Asp Val
            565                 570                 575
Val Val Pro Val Ile Glu Pro Ser His Thr Arg Ser Gly Thr Pro Ile
            580                 585                 590
Ser Thr Arg Thr Asp Leu Val Arg Ala Leu Arg His Gly Val Ala Ile
            595                 600                 605
```

Glu Leu Ala Val Met Leu Gln Tyr Leu Tyr Ala Ala Phe Ser Ile Pro
610                 615                 620

Thr His Gly Ala Gly Gln Glu Leu Val Ser Arg Gly Asp Trp Thr Pro
625                 630                 635                 640

Glu Gln Leu Arg Leu Met Cys Gly Asp Gly Glu Thr Thr Asp Gly
                645                 650                 655

Gly Val Arg Gly Ser Leu Leu Gly Val Ala Arg Glu Glu Met Ile His
            660                 665                 670

Phe Leu Val Val Asn Asn Val Leu Met Ala Val Gly Glu Pro Phe His
            675                 680                 685

Val Pro Asp Leu Asp Phe Gly Thr Ile Asn Asp Thr Leu Met Val Pro
690                 695                 700

Leu Asp Phe Ser Leu Glu Ala Leu Gly Leu Gly Ser Val Gln Arg Phe
705                 710                 715                 720

Ile Gln Ile Glu Gln Pro Glu Gly Leu Thr Gly Ala Val Arg Leu Gly
                725                 730                 735

Asp Leu Pro Val Pro Val Arg Glu Ala Glu Asp Phe His Tyr Ala Ser
            740                 745                 750

Leu Ser Glu Leu Tyr Gly Asp Ile Arg Glu Gly Leu Gln Arg Val Pro
            755                 760                 765

Gly Leu Phe Leu Val Glu Arg Gly Arg Gly Gly Glu His His Leu
770                 775                 780

Phe Leu Arg Glu Ser Val Asn Ala Val His Pro Asp Tyr Gln Leu Glu
785                 790                 795                 800

Val Asp Asp Leu Ser Ser Ala Leu Phe Ala Ile Asp Phe Val Thr Glu
                805                 810                 815

Gln Gly Glu Gly His Val Leu Thr Asp Glu Asp Thr Gly Glu Glu Ser
            820                 825                 830

His Tyr Asp Thr Phe Val Arg Val Ala Asp Leu Leu Met Lys Glu Arg
            835                 840                 845

Leu Thr Ala Ala Asp Thr Arg Arg Ala Gln Trp Ser Pro Ala Tyr Pro
850                 855                 860

Val Ala Arg Asn Pro Thr Val His Gly Gly Gln Ser Lys Glu Leu
865                 870                 875                 880

Val Thr Ser Pro Val Ala Arg Glu Leu Met Val Leu Phe Asn Lys Ser
                885                 890                 895

Tyr Phe Met Met Leu Gln Leu Met Val Gln His Phe Gly Gly Ser Pro
            900                 905                 910

Asp Ala Ser Leu Arg Arg Ser Lys Leu Met Asn Ala Ala Ile Asp Val
            915                 920                 925

Met Thr Gly Val Met Arg Pro Leu Ala Glu Leu Leu Val Thr Val Pro
930                 935                 940

Ser Gly Arg His Gly Arg Thr Ala Gly Pro Ser Phe Glu Leu Asp Glu
945                 950                 955                 960

Lys Pro Ala Phe Ile Pro Arg Ala Asp Val Ala Arg Ala Ile Ser
                965                 970                 975

Leu Arg Phe Arg His Leu Ala Glu Ser Ala Arg Thr Cys Ala Leu Val
            980                 985                 990

Pro Asp Lys Val Val Arg Asn Leu Asp Phe Leu Ala Asp Gln Phe Ala
            995                 1000                1005

Thr Glu Gly Pro Arg
1010

<210> SEQ ID NO 11

<211> LENGTH: 528
<212> TYPE: PRT
<213> ORGANISM: ARTIFICIAL
<220> FEATURE:
<223> OTHER INFORMATION: OrfD5

<400> SEQUENCE: 11

```
Met Asn Ala Pro Ile Glu Thr Asp Val Leu Ile Leu Gly Gly Gly Pro
1               5                   10                  15

Val Gly Met Ala Leu Ala Leu Asp Leu Ala His Arg Gln Val Gly His
            20                  25                  30

Leu Val Val Glu Gln Thr Asp Gly Thr Ile Thr His Pro Arg Val Gly
        35                  40                  45

Thr Ile Gly Pro Arg Ser Met Glu Leu Phe Arg Arg Trp Gly Val Ala
    50                  55                  60

Lys Gln Ile Arg Thr Ala Gly Trp Pro Gly Asp His Pro Leu Asp Ala
65                  70                  75                  80

Ala Trp Val Thr Arg Val Gly Gly His Glu Val Tyr Arg Ile Pro Leu
                85                  90                  95

Gly Thr Ala Asp Thr Arg Ala Thr Pro Glu His Thr Pro Glu Pro Asp
            100                 105                 110

Ala Ile Cys Pro Gln His Trp Leu Ala Pro Leu Leu Ala Glu Ala Val
        115                 120                 125

Gly Glu Arg Leu Arg Thr Arg Ser Arg Leu Asp Ser Phe Glu Gln Arg
    130                 135                 140

Asp Asp His Val Arg Ala Thr Ile Thr Asp Leu Arg Thr Gly Ala Thr
145                 150                 155                 160

Arg Ala Val His Ala Arg Tyr Leu Val Ala Cys Asp Gly Ala Ser Ser
                165                 170                 175

Pro Thr Arg Lys Ala Leu Gly Ile Asp Ala Pro Pro Arg His Arg Thr
            180                 185                 190

Gln Val Phe Arg Asn Ile Leu Phe Arg Ala Pro Glu Leu Arg Ser Leu
        195                 200                 205

Leu Gly Glu Arg Ala Ala Leu Phe Phe Phe Leu Met Leu Ser Ser Ser
    210                 215                 220

Leu Arg Phe Pro Leu Arg Ala Leu Asp Gly Arg Gly Leu Tyr Arg Leu
225                 230                 235                 240

Thr Val Gly Val Asp Asp Ala Ser Lys Ser Thr Met Asp Ser Phe Glu
                245                 250                 255

Leu Val Arg Arg Ala Val Ala Phe Asp Thr Glu Ile Glu Val Leu Ser
            260                 265                 270

Asp Ser Glu Trp His Leu Thr His Arg Val Ala Asp Ser Phe Ser Ala
        275                 280                 285

Gly Arg Val Phe Leu Thr Gly Asp Ala Ala His Thr Leu Ser Pro Ser
    290                 295                 300

Gly Gly Phe Gly Met Asn Thr Gly Ile Gly Ser Ala Ala Asp Leu Gly
305                 310                 315                 320

Trp Lys Leu Ala Ala Thr Leu Arg Gly Trp Ala Gly Pro Gly Leu Leu
                325                 330                 335

Ala Thr Tyr Glu Glu Glu Arg Arg Pro Val Ala Ile Thr Ser Leu Glu
            340                 345                 350

Glu Ala Asn Val Asn Leu Arg Arg Thr Met Asp Arg Glu Leu Pro Pro
        355                 360                 365

Gly Leu His Asp Asp Gly Pro Arg Gly Glu Arg Ile Arg Ala Ala Val
    370                 375                 380
```

```
Ala Glu Lys Leu Glu Arg Ser Gly Ala Arg Arg Glu Phe Asp Ala Pro
385                 390                 395                 400

Gly Ile His Phe Gly His Thr Tyr Arg Ser Ile Val Cys Gly Glu
            405                 410                 415

Pro Glu Thr Glu Val Ala Thr Gly Gly Trp Arg Pro Ser Ala Arg Pro
        420                 425                 430

Gly Ala Arg Ala Pro His Ala Trp Leu Thr Pro Thr Thr Ser Thr Leu
        435                 440                 445

Asp Leu Phe Gly Arg Gly Phe Val Leu Leu Ser Phe Gly Thr Thr Asp
        450                 455                 460

Gly Val Glu Ala Val Thr Arg Ala Phe Ala Asp Arg His Val Pro Leu
465                 470                 475                 480

Glu Thr Val Thr Cys His Ala Pro Glu Ile His Ala Leu Tyr Glu Arg
                485                 490                 495

Ala His Val Leu Val Arg Pro Asp Gly His Val Ala Trp Arg Gly Asp
                500                 505                 510

His Leu Pro Ala Glu Leu Gly Gly Leu Val Asp Lys Val Arg Gly Ala
            515                 520                 525

<210> SEQ ID NO 12
<211> LENGTH: 397
<212> TYPE: PRT
<213> ORGANISM: ARTIFICIAL
<220> FEATURE:
<223> OTHER INFORMATION: OrfD6

<400> SEQUENCE: 12

Met Lys Pro Phe Asp Leu Lys Ala Phe Thr Gly Ala Asp Leu Ala Asp
1               5                   10                  15

Pro Tyr Pro Val Tyr Arg Glu Tyr Leu Thr Gly Asp Pro Val His His
            20                  25                  30

Asn Gly Glu Ala Trp Tyr Val Phe Gly Tyr Asp Gly Val Ala His Val
        35                  40                  45

Leu Thr Ser Arg Asp Tyr Gly Arg Arg Gly Pro Gly Gly Arg Ala Thr
    50                  55                  60

Pro Ile Pro Pro Ser His Asp Thr Leu Ser Arg Ile Val Glu Asn Trp
65                  70                  75                  80

Leu Val Phe Leu Asp Pro Pro Arg His Thr Ala Leu Arg Ser Leu Leu
                85                  90                  95

Ala Lys Glu Phe Ser Pro Ala Val Val Thr Gly Leu Arg Glu Arg Val
            100                 105                 110

Arg Lys Ile Ala Gly Glu Leu Leu Ala Gly Leu Gly Asp Ala Gly Glu
        115                 120                 125

Ile Asp Leu Val Glu Asp Phe Ala Ala Pro Leu Pro Ile Leu Val Ile
    130                 135                 140

Ser Glu Leu Leu Gly Val Pro Ala Arg Leu Arg Ser Trp Phe Arg Arg
145                 150                 155                 160

Cys Ala Val Asp Leu Gln Glu Ala Ser Thr Ala Arg Ala Thr Arg Asn
                165                 170                 175

Pro Gly Ala Leu Ala Arg Ala Asp Gly Ala Ser Glu Leu Val Glu
            180                 185                 190

Phe Phe Gly Gly Glu Leu Gly Thr Arg Lys Pro Asp Asp Glu Asp Leu
        195                 200                 205

Val Ala Leu Leu Val Asn Ala Gln Arg Arg Gly Glu Ala Leu Thr Asp
    210                 215                 220

Glu Glu Ile Val Ser Thr Cys Val His Leu Leu Thr Ala Gly His Glu
```

```
                  225                 230                 235                 240

Thr Thr Thr Asn Leu Ile Ser Lys Ser Val Leu Ala Leu Leu Ala Asn
                245                 250                 255

Pro Ala Ala Ala Glu Pro Leu Ala Gly Leu Asp Val Thr Pro Gln
            260                 265                 270

Val Val Glu Glu Leu Asn Arg Phe Asp Thr Pro Val Gln Met Val Thr
        275                 280                 285

Arg Trp Ala His Gln Asp Thr Ala Leu Gly Gly Lys Pro Ile Arg Arg
    290                 295                 300

Gly Asp Lys Val Val Leu Val Leu Gly Ser Ala Asn Arg Asp Pro Ala
305                 310                 315                 320

Ala Phe Ala Glu Pro Asp Arg Leu Asp Leu Arg Arg Asp Ser Arg Arg
                325                 330                 335

His Cys Gly Phe Gly Leu Gly Ile His Tyr Cys Leu Gly Ala Ala Leu
            340                 345                 350

Ala Arg Thr Glu Ala Glu Ile Gly Leu Ser Val Leu Phe Thr Asn Phe
        355                 360                 365

Pro Gly Leu Arg Leu Gly Gly Glu Pro Val Arg Tyr Ala Asp Asp Leu
    370                 375                 380

Val Phe His Gly Pro Ala Arg Leu Pro Met Leu Thr Arg
385                 390                 395

<210> SEQ ID NO 13
<211> LENGTH: 766
<212> TYPE: PRT
<213> ORGANISM: ARTIFICIAL
<220> FEATURE:
<223> OTHER INFORMATION: OrfD7

<400> SEQUENCE: 13

Met Glu Thr Ala Leu Ala Ala Leu Ala Pro Arg Thr His Arg Pro Arg
1               5                   10                  15

Gly Leu Gly Leu Val Ala Leu Ala Arg Gly Gly Leu Asn Met Glu Thr
            20                  25                  30

Thr Tyr Arg Ala Ser Pro Ala Ser Pro Pro His Glu Thr His Arg Ala
        35                  40                  45

Ser Pro Pro Arg Pro His Glu Ala Leu Ala Ala Arg Gly Ile Leu Glu
    50                  55                  60

Thr Arg Pro Gly Leu Tyr Gly Leu Ala Ser Asn Leu Glu His Ile Ser
65                  70                  75                  80

Pro His Glu Gly Leu Tyr Thr Tyr Arg Thr Arg Pro Gly Leu Ala Ser
                85                  90                  95

Pro Ala Leu Ala Gly Leu Tyr Ala Leu Ala Ala Ser Pro Val Ala Leu
            100                 105                 110

Ser Glu Arg Val Ala Leu Ala Ser Pro Ala Ser Pro Ala Leu Ala Thr
        115                 120                 125

His Arg Ala Ser Pro Ala Arg Gly Leu Glu Thr His Arg Ala Ser Pro
    130                 135                 140

Gly Leu Met Glu Thr Ile Leu Glu Ala Leu Ala Leu Glu Leu Glu Ala
145                 150                 155                 160

Ser Pro Val Ala Leu Ala Arg Gly Ser Glu Arg Gly Leu Tyr Ala Ser
                165                 170                 175

Pro Ala Arg Gly Val Ala Leu Leu Glu Ala Ser Pro Val Ala Leu Gly
            180                 185                 190

Leu Tyr Cys Tyr Ser Gly Leu Tyr Ile Leu Glu Gly Leu Tyr Leu Tyr
        195                 200                 205
```

-continued

```
Ser Pro Arg Ala Leu Ala Val Ala Leu Ala Arg Gly Leu Glu Ala Leu
    210                 215                 220
Ala Thr His Arg Ala Leu Ala Ala Arg Gly Ala Ser Pro Val Ala Leu
225                 230                 235                 240
Ala Arg Gly Val Ala Leu Thr His Arg Gly Leu Tyr Ile Leu Glu Ser
            245                 250                 255
Glu Arg Ile Leu Glu Ser Glu Arg Ala Arg Gly Pro Arg Gly Leu Asn
        260                 265                 270
Val Ala Leu Ala Ser Asn Gly Leu Asn Ala Leu Ala Ala Ser Asn Ala
    275                 280                 285
Leu Ala Ala Arg Gly Ala Leu Ala Thr His Arg Ala Leu Ala Ala Leu
    290                 295                 300
Ala Gly Leu Tyr Leu Glu Ala Leu Ala Ala Ser Asn Ala Arg Gly Val
305                 310                 315                 320
Ala Leu Thr His Arg Pro His Glu Ser Glu Arg Thr Tyr Arg Ala Leu
            325                 330                 335
Ala Ala Ser Pro Ala Leu Ala Met Glu Thr Ala Ser Pro Leu Glu Pro
        340                 345                 350
Arg Pro His Glu Gly Leu Ala Ser Pro Ala Leu Ala Ser Glu Arg Pro
    355                 360                 365
His Glu Ala Ser Pro Ala Leu Ala Val Ala Leu Thr Arg Pro Ala Leu
    370                 375                 380
Ala Leu Glu Gly Leu Ser Glu Arg Leu Glu His Ile Ser His Ile Ser
385                 390                 395                 400
Met Glu Thr Pro Arg Ala Ser Pro Ala Arg Gly Gly Leu Tyr Ala Arg
            405                 410                 415
Gly Ala Leu Ala Leu Glu Ala Arg Gly Gly Leu Met Glu Thr Ala Leu
        420                 425                 430
Ala Ala Arg Gly Val Ala Leu Leu Glu Ala Arg Gly Pro Arg Gly Leu
    435                 440                 445
Tyr Gly Leu Tyr Thr His Arg Val Ala Leu Ala Leu Ala Ile Leu Glu
    450                 455                 460
Ala Leu Ala Ala Ser Pro Pro His Glu Val Ala Leu Leu Glu Leu Glu
465                 470                 475                 480
Ala Leu Ala Pro Arg Val Ala Leu Gly Leu Gly Leu Tyr Ala Leu Ala
            485                 490                 495
Leu Tyr Ser Leu Tyr Ser Gly Leu Ala Leu Ala Val Ala Leu Ala Ser
        500                 505                 510
Pro Ala Leu Ala Pro His Glu Ala Arg Gly Ala Leu Ala Gly Leu Tyr
    515                 520                 525
Gly Leu Tyr Gly Leu Tyr Val Ala Leu Leu Glu Ser Glu Arg Leu Glu
    530                 535                 540
Gly Leu Tyr Gly Leu Tyr Ile Leu Glu Ala Ser Pro Gly Leu Thr Tyr
545                 550                 555                 560
Arg Gly Leu Ser Glu Arg Ala Ser Pro Val Ala Leu Ala Arg Gly Gly
            565                 570                 575
Leu Asn Ala Leu Ala Gly Leu Leu Glu Val Ala Leu Val Ala Leu Thr
        580                 585                 590
His Arg Ser Glu Arg Thr His Arg Val Ala Leu Ala Ser Pro Ile Leu
    595                 600                 605
Glu Ser Glu Arg Ala Leu Ala Gly Leu Asn Ala Leu Ala Ala Arg Gly
    610                 615                 620
Pro Arg Ser Glu Arg Leu Glu Val Ala Leu Leu Tyr Ser Thr His Arg
```

```
                    625                 630                 635                 640

Ala Leu Ala Gly Leu Ala Leu Ala Pro His Glu Gly Leu Ala Ser Asn
                    645                 650                 655

Ala Leu Ala Ala Arg Gly Ser Glu Arg Gly Leu Asn Val Ala Leu Gly
                    660                 665                 670

Leu Pro Arg Pro His Glu Met Glu Thr Gly Leu Tyr Ala Leu Ala Gly
                    675                 680                 685

Leu Gly Leu Tyr Leu Glu Ala Ser Pro Ala Arg Gly Met Glu Thr Ile
                    690                 695                 700

Leu Glu Ala Leu Ala Thr His Arg Pro His Glu Ala Arg Gly Gly Leu
705                 710                 715                 720

Tyr Leu Glu Ala Leu Ala Gly Leu Val Ala Leu Pro Arg Gly Leu Ala
                    725                 730                 735

Leu Ala Gly Leu Tyr Thr Tyr Arg Val Ala Leu Leu Glu Ile Leu Glu
                    740                 745                 750

Gly Leu Tyr Ala Leu Ala Ala Arg Gly Leu Tyr Ser Pro Arg
                    755                 760                 765

<210> SEQ ID NO 14
<211> LENGTH: 923
<212> TYPE: PRT
<213> ORGANISM: ARTIFICIAL
<220> FEATURE:
<223> OTHER INFORMATION: OrfD8

<400> SEQUENCE: 14

Met Thr Arg Ser Arg Lys Ala Glu Phe Leu Ser Asp Val His Gln Asp
1               5                   10                  15

Asn Ala Asn Ser Phe Pro Gln Trp Asn Pro Arg Glu Thr Asn Cys Val
                20                  25                  30

Ala Leu Pro Gly Arg Pro Val Arg Gly Arg Glu Ala Glu Leu Ala Arg
                35                  40                  45

Ile Glu Gln Ala Leu Asp Asp Ala Ala Asn Ala Arg Gly Gly Val Leu
            50                  55                  60

Leu Val Glu Gly Ala Arg Gly Ser Gly Arg Ser Arg Leu Leu Ala Glu
65                  70                  75                  80

Thr Ala Arg Arg Ala Ala Glu Arg Gly Phe Asp Val Val Ser Ala Glu
                85                  90                  95

Ala Asn Glu Leu Ala Arg Leu Val Pro Leu Ala Pro Ile Leu Ala Ala
                100                 105                 110

Leu Gly Glu Pro Gln Pro Val Pro Gly Glu Ala Asp His Ser Phe Ala
                115                 120                 125

Gly Leu Asp Asp Arg Trp Ser Arg Gln Leu Ala His Val Arg Gly Arg
            130                 135                 140

Leu Ala Arg Arg Ile Val Lys Arg Pro Leu Ala Val Leu Leu Asp Asp
145                 150                 155                 160

Leu Gln Trp Ala Asp Pro Val Thr Leu Leu Ala Leu Arg Ile Leu Pro
                165                 170                 175

Ala Gln Leu Ala Gly Gln Pro Leu Leu Trp Met Leu Cys Arg Arg Thr
                180                 185                 190

Asp Glu Arg Glu Pro Tyr Val Ala Gln Leu Tyr Asp Gln Leu Leu Ala
                195                 200                 205

Ala Gly Val Ala Thr Pro Leu Arg Leu Gln Pro Leu Thr Ala Pro Ala
            210                 215                 220

Ala Asp Glu Met Ala Ala Asp Leu Leu Gly Gly Ala Lys Pro Ala Pro
225                 230                 235                 240
```

```
Glu Val Asn Ala Leu Val Gly Ala Ala Asp Gly Asn Pro Ala Val Leu
            245                 250                 255

Thr Glu Leu Ile Glu Gly Leu Val Asp Glu Asn Val Val Cys Ser
        260                 265                 270

Asp Gly Thr Ala Arg Leu Val His Gly Asn Ala Ser Ala Leu Leu Pro
            275                 280                 285

Gln Arg Phe Arg Ser Leu Met Arg Gly Arg Ile Asp Ala Leu Ser Pro
        290                 295                 300

Ser Thr Ala Arg Met Leu Glu Val Ala Ala Val Leu Gly Arg Ser Trp
305                 310                 315                 320

Leu Pro Asp Asp Val Val Glu Met Leu Gly Thr Ser Thr Ala Glu Leu
            325                 330                 335

Leu Pro Cys Phe Gln Glu Ala Leu Ala Ala Arg Leu Leu Met Ser Thr
            340                 345                 350

Ser Asp Thr Met Val Phe Arg His Asp Leu Val Trp Arg Ser Ile Thr
            355                 360                 365

Glu Ser Ile Pro Pro Ala Val Cys Ala Ala Leu His Arg Gln Ala Ala
        370                 375                 380

Arg Met Leu Leu Asp Arg Gly Ser Pro Val Val Ser Val Ala Val His
385                 390                 395                 400

Leu Ala Arg Gly Ala Arg Pro His Asp Val Glu Ala Val Ala Val Leu
            405                 410                 415

Lys Asn Ala Ala Thr Glu Val Met Thr Ser Ser Pro Arg Thr Ala Val
            420                 425                 430

Glu Phe Ala Ser Arg Ala Leu Glu Leu Thr Asp Arg Asp Gly Ser Thr
        435                 440                 445

Arg Pro Ala Leu Thr Ala Val Leu Val Glu Ala His Thr Arg Ala Gly
        450                 455                 460

Ala Leu Gly Arg Ala Val Ala Val Ala Asn Ala Gly Pro Glu Thr
465                 470                 475                 480

Pro Ala Pro Ala Leu His Arg Ser Leu Ser Thr Ala Leu Leu Leu Arg
            485                 490                 495

Gly Glu Ala Arg Glu Ala Leu Ala Val Ser Glu Lys Ala Leu Ala Ala
        500                 505                 510

Ala Ser Val Thr Pro Glu Thr Arg Glu Ala Leu Glu Ile Asn Arg Leu
        515                 520                 525

Ala Ala Leu Ala Ala Leu Asp Asp Asp Ala Leu Gly Ser Glu Val Arg
530                 535                 540

Arg Cys Thr Gly Asp Ser Pro Gly Val Leu Thr Val Leu Ala Thr Ala
545                 550                 555                 560

Arg Trp Gln Arg Gly Glu Phe Ala Glu Gly Leu Arg Leu Ala Arg Ala
            565                 570                 575

Ala Ala Arg Ala Ala Glu Glu Gly Ala Pro Phe Pro Trp His Leu Asp
            580                 585                 590

Pro Arg Ile Ala Leu Ala Ala Phe Leu Val Gln Ser Arg Arg Glu Asp
        595                 600                 605

Glu Ala Arg Gln Val Ile Thr Val Leu Asp Gly Asp Ile Gly Arg Ser
        610                 615                 620

Gly Leu Asp Val Leu Ala Ser Val Pro His Leu Leu Met Ala Gln Leu
625                 630                 635                 640

His Leu Ala Ala Gly Arg Val Glu Glu Ala Ala Ser Arg Ala His Ala
            645                 650                 655

Ala Leu Ala Glu Pro Val Thr Thr His Thr Pro Ile Ala His Ala Val
```

```
                    660                 665                 670
Leu Ala Ala Val Ala Leu Arg Arg Gly Asp Leu Val Ala Ala Glu
                675                 680                 685
His Ala His His Leu Asp Gly Val Arg Pro Val His Trp Arg Ala Gln
    690                 695                 700
Thr Arg Trp Val Arg Thr Gln Leu Thr Ala Thr Ala Asp Ala Asp Ala
705                 710                 715                 720
Gly Phe Ser Leu Ala Leu Leu Ala Glu Glu Pro Ala Ala Ala Ala Trp
                725                 730                 735
His Val Arg Thr Ala Leu Val Ala Gly Glu Ala Asp Arg Ala Ala
            740                 745                 750
Val Leu Arg Arg Ile Ala Ala Asp His Cys Pro Ala Ala Asp His
        755                 760                 765
Ala Arg Gly Val Arg Asp Gly Asp Arg Ser Ala Leu Glu Arg Ala Val
    770                 775                 780
Arg Asp His Val Asp Glu Trp Ala Arg Ala Ser Ala Ala Glu Asp Leu
785                 790                 795                 800
Gly Val Leu Leu Thr Pro Asp Asp Arg Asn Ala Ala Val Glu Arg Leu
                805                 810                 815
Asp Gln Ala Leu Thr Ala Tyr Thr Ala Ala Gly Ala Glu Arg Asp Ala
            820                 825                 830
Ala Arg Val Arg Arg Arg Leu Arg Gly Leu Gly Val Arg Arg His
        835                 840                 845
Trp Arg Thr Ala Asp Arg Pro Glu Ser Gly Trp Asp Ser Leu Thr Asn
    850                 855                 860
Thr Glu Leu Ser Val Ala Ser Leu Val Thr Gln Gly Leu Thr Asn Lys
865                 870                 875                 880
Gln Val Ala Thr Gln Met Phe Leu Ser Pro His Thr Val Gly Phe His
                885                 890                 895
Leu Arg Gln Ile Phe Arg Lys Leu Gly Val His Ser Arg Thr Glu Leu
            900                 905                 910
Ile Arg Phe Gly Pro Asn Ala Gly Arg Thr Arg
        915                 920

<210> SEQ ID NO 15
<211> LENGTH: 170
<212> TYPE: PRT
<213> ORGANISM: ARTIFICIAL
<220> FEATURE:
<223> OTHER INFORMATION: OrfD9

<400> SEQUENCE: 15

Met Thr Ile Glu Phe Asp Arg Pro Gly Ala His Val Thr Ala Ala Asp
1               5                   10                  15
His Arg Ala Leu Met Ser Leu Phe Pro Thr Gly Val Ala Val Ile Thr
            20                  25                  30
Ala Ile Asp Glu Ala Gly Thr Pro His Gly Met Thr Cys Thr Ser Leu
        35                  40                  45
Thr Ser Val Thr Leu Asp Pro Pro Thr Leu Leu Val Cys Leu Asn Arg
    50                  55                  60
Ala Ser Gly Thr Leu His Ala Val Arg Gly Gly Arg Phe Gly Val Asn
65                  70                  75                  80
Leu Leu His Ala Arg Gly Arg Arg Ala Ala Glu Val Phe Ser Thr Ala
                85                  90                  95
Val Gln Asp Arg Phe Gly Glu Val Arg Trp Glu His Ser Asp Val Thr
            100                 105                 110
```

```
Gly Met Pro Trp Leu Ala Glu Asp Ala His Ala Phe Ala Gly Cys Val
        115                 120                 125

Val Arg Lys Ser Thr Val Val Gly Asp His Glu Ile Val Leu Gly Glu
    130                 135                 140

Val His Glu Val Val Arg Glu His Asp Leu Pro Leu Leu Tyr Gly Met
145                 150                 155                 160

Arg Glu Phe Ala Val Trp Thr Pro Glu Gly
            165                 170
```

<210> SEQ ID NO 16
<211> LENGTH: 426
<212> TYPE: PRT
<213> ORGANISM: ARTIFICIAL
<220> FEATURE:
<223> OTHER INFORMATION: OrfD10

<400> SEQUENCE: 16

```
Met Ser Val His Ile Glu Pro Ile Gly Arg Phe Leu Leu Ala Val Gly
1               5                   10                  15

Val Ile Val Ala Val Cys His Leu Gly Gly Leu Leu Cys His Arg Ile
                20                  25                  30

Arg Gln Pro Pro Val Ile Gly Glu Ile Ala Ala Gly Leu Leu Leu Gly
            35                  40                  45

Pro Thr Leu Leu Gly Ala Val Ala Pro Ser Leu Gln Arg Ala Leu Phe
    50                  55                  60

Pro Glu Glu Val Leu Gln Ala Val Gly Met Ala Ala Gln Leu Gly Leu
65                  70                  75                  80

Val Thr Phe Met Phe Leu Leu Gly Ser Glu Leu Arg Val Asp His Val
                85                  90                  95

Arg Gly Asn Gly Lys Val Val Trp Ala Leu Val Ala Gly Ser Ile Leu
            100                 105                 110

Leu Pro Phe Leu Ala Gly Thr Gly Phe Ala Leu Leu Thr Arg Pro Ala
        115                 120                 125

Phe Gly Thr Pro Gln Val Ser Thr Thr Ala Tyr Ala Leu Phe Val Gly
    130                 135                 140

Leu Ala Met Ser Ile Thr Ala Leu Pro Val Leu Ala Arg Ile Leu Ala
145                 150                 155                 160

Asp Phe Arg Ala Asp Gln Ser Phe Leu Gly Thr Leu Ala Leu Met Ala
                165                 170                 175

Ala Ala Val Gly Asp Ala Leu Ala Trp Ala Ala Leu Thr Val Ile Leu
            180                 185                 190

Ala Val Thr Gly Ser Gly Ser Thr Gly Glu Leu Val Leu Arg Ser Ala
        195                 200                 205

Leu Ala Leu Thr Leu Val Leu Leu Thr Val Phe Val Val Lys Pro Ala
    210                 215                 220

Leu Arg Thr Leu Leu His Arg Leu Pro Val Asn Ser Arg Val Thr Val
225                 230                 235                 240

Pro Ala Leu Val Val Gly Thr Thr Ala Phe Ala Ala Thr Thr Glu Val
                245                 250                 255

Ile Gly Leu His Pro Val Ile Gly Ala Phe Leu Phe Gly Cys Ala Met
            260                 265                 270

Pro Arg Gly Ser Ala Val Leu Gln Arg Ala Ser Ala Gln Leu Arg Gly
        275                 280                 285

Phe Thr Val Ser Val Leu Leu Pro Leu Phe Phe Ala Gly Val Ala Met
    290                 295                 300
```

```
Lys Thr Ala Phe Asp Ala Phe Gly Thr Ala Gly Asn Trp Leu Leu Phe
305                 310                 315                 320

Ala Ala Ala Leu Ala Val Ala Thr Val Thr Lys Phe Val Gly Ala Ser
                325                 330                 335

Ser Gly Ala Leu Leu Ala Gly Leu Asp Arg Ala Arg Ala Phe Gln Leu
            340                 345                 350

Gly Ala Leu Met Asn Cys Arg Gly Val Thr Glu Leu Val Val Ala Thr
        355                 360                 365

Val Gly Leu Gln Asn Gly Phe Val Asn Glu Phe Gly Tyr Thr Val Leu
370                 375                 380

Val Leu Ile Ala Leu Val Thr Thr Ala Leu Thr Gly Pro Leu Ala Arg
385                 390                 395                 400

Leu Arg Ala Glu Glu Ala Pro Gln Glu Asn His Arg Ile Pro Met Lys
                405                 410                 415

His Gly Gly Thr Phe His Val Arg Gln Asp
            420                 425

<210> SEQ ID NO 17
<211> LENGTH: 530
<212> TYPE: PRT
<213> ORGANISM: ARTIFICIAL
<220> FEATURE:
<223> OTHER INFORMATION: OrfD11

<400> SEQUENCE: 17

Met Ser Gly Lys Ile Asp Lys Ile Leu Ile Val Gly Gly Thr Ala
1               5                   10                  15

Gly Trp Met Ala Ala Ser Tyr Leu Gly Lys Ala Leu Gln Gly Thr Ala
                20                  25                  30

Asp Ile Thr Leu Leu Gln Ala Pro Asp Ile Pro Thr Leu Gly Val Gly
            35                  40                  45

Glu Ala Thr Ile Pro Asn Leu Gln Thr Ala Phe Phe Asp Phe Leu Gly
        50                  55                  60

Ile Pro Glu Asp Glu Trp Met Arg Glu Cys Asn Ala Ser Tyr Lys Val
65                  70                  75                  80

Ala Ile Lys Phe Ile Asn Trp Arg Thr Ala Gly Glu Gly Thr Ser Glu
                85                  90                  95

Ala Arg Glu Leu Asp Gly Gly Pro Asp His Phe Tyr His Ser Phe Gly
            100                 105                 110

Leu Leu Lys Tyr His Glu Gln Ile Pro Leu Ser His Tyr Trp Phe Asp
        115                 120                 125

Arg Ser Tyr Arg Gly Lys Thr Val Glu Pro Phe Asp Tyr Ala Cys Tyr
130                 135                 140

Lys Glu Pro Val Ile Leu Asp Ala Asn Arg Ser Pro Arg Arg Leu Asp
145                 150                 155                 160

Gly Ser Lys Val Thr Asn Tyr Ala Trp His Phe Asp Ala His Leu Val
                165                 170                 175

Ala Asp Phe Leu Arg Arg Phe Ala Thr Glu Lys Leu Gly Val Arg His
            180                 185                 190

Val Glu Asp Arg Val Glu His Val Gln Arg Asp Ala Asn Gly Asn Ile
        195                 200                 205

Glu Ser Val Arg Thr Ala Thr Gly Arg Val Phe Asp Ala Asp Leu Phe
210                 215                 220

Val Asp Cys Ser Gly Phe Arg Gly Leu Leu Ile Asn Lys Ala Met Glu
225                 230                 235                 240

Glu Pro Phe Leu Asp Met Ser Asp His Leu Leu Asn Asp Ser Ala Val
```

```
                245                 250                 255
Ala Thr Gln Val Pro His Asp Asp Ala Asn Gly Val Glu Pro Phe
            260                 265                 270

Thr Ser Ala Ile Ala Met Lys Ser Gly Trp Thr Trp Lys Ile Pro Met
        275                 280                 285

Leu Gly Arg Phe Gly Thr Gly Tyr Val Tyr Ser Ser Arg Phe Ala Thr
        290                 295                 300

Glu Asp Glu Ala Val Arg Glu Phe Cys Glu Met Trp His Leu Asp Pro
305                 310                 315                 320

Glu Thr Gln Pro Leu Asn Arg Ile Arg Phe Arg Val Gly Arg Asn Arg
            325                 330                 335

Arg Ala Trp Val Gly Asn Cys Val Ser Ile Gly Thr Ser Ser Cys Phe
            340                 345                 350

Val Glu Pro Leu Glu Ser Thr Gly Ile Tyr Phe Val Tyr Ala Ala Leu
            355                 360                 365

Tyr Gln Leu Val Lys His Phe Pro Asp Lys Ser Leu Asn Pro Val Leu
        370                 375                 380

Thr Ala Arg Phe Asn Arg Glu Ile Glu Thr Met Phe Asp Asp Thr Arg
385                 390                 395                 400

Asp Phe Ile Gln Ala His Phe Tyr Phe Ser Pro Arg Thr Asp Thr Pro
            405                 410                 415

Phe Trp Arg Ala Asn Lys Glu Leu Leu Ala Asp Gly Met Gln Glu
            420                 425                 430

Lys Ile Asp Met Tyr Arg Ala Gly Met Ala Ile Asn Ala Pro Ala Ser
        435                 440                 445

Asp Asp Ala Gln Leu Tyr Tyr Gly Asn Phe Glu Glu Phe Arg Asn
450                 455                 460

Phe Trp Asn Asn Ser Asn Tyr Tyr Cys Val Leu Ala Gly Leu Gly Leu
465                 470                 475                 480

Val Pro Asp Ala Pro Ser Pro Arg Leu Ala His Met Pro Gln Ala Thr
            485                 490                 495

Glu Ser Val Asp Glu Val Phe Gly Ala Val Lys Asp Arg Gln Arg Asn
            500                 505                 510

Leu Leu Glu Thr Leu Pro Ser Leu His Glu Phe Leu Arg Gln Gln His
        515                 520                 525

Gly Arg
    530

<210> SEQ ID NO 18
<211> LENGTH: 473
<212> TYPE: PRT
<213> ORGANISM: ARTIFICIAL
<220> FEATURE:
<223> OTHER INFORMATION: OrfR1

<400> SEQUENCE: 18

Met Thr Ala Asp Glu Arg Asp Arg Ala Arg Ser Ala Leu Pro Phe Leu
1               5                   10                  15

Val Ile Thr Gln Leu Met Ile Val Leu Asp Ala Ser Ile Val Asn Ile
            20                  25                  30

Ala Leu Pro Ser Met Gly Arg Glu Leu Gly Met Asp Gln Thr Gly Leu
        35                  40                  45

Gln Trp Val Val Asn Ala Tyr Thr Leu Thr Phe Gly Gly Phe Leu Met
    50                  55                  60

Leu Gly Gly Arg Met Ala Asp Leu Ile Gly Arg Arg Leu Val Phe Val
65                  70                  75                  80
```

Ser Gly Ile Cys Leu Phe Gly Ala Ala Ser Leu Ala Ala Ala Leu Ala
                85                  90                  95

Pro Val Ala Gly Val Leu Val Ala Ala Arg Ala Val Gln Gly Leu Ser
                100                 105                 110

Ala Ala Val Ala Ser Ala Ala Leu Ser Ile Ile Val Ala Thr Phe
            115                 120                 125

Pro Glu Gly Lys Gly Arg Asn Gln Ala Leu Ala Met Trp Gly Ala Val
130                 135                 140

Ser Gly Val Gly Gly Ala Val Gly Val Leu Leu Gly Gly Val Leu Thr
145                 150                 155                 160

Ser Gly Pro Gly Trp Pro Trp Ile Phe Tyr Ile Asn Val Pro Ile Val
                165                 170                 175

Val Val Val Val Leu Gly Val Phe Arg Ser Val Ser Gly Ala Arg Gly
                180                 185                 190

Asp Thr Arg Gly Arg Leu Asp Val Ala Gly Ala Val Thr Leu Thr Gly
                195                 200                 205

Gly Leu Thr Leu Leu Val Tyr Ala Ile Val Ser Gly Gln Ser Gly Asp
                210                 215                 220

Pro Val Thr Ile Leu Leu Ala Leu Gly Leu Ala Val Val Leu Leu Val
225                 230                 235                 240

Ser Phe Phe Leu Val Gln Arg Lys Val Arg Glu Pro Leu Val Pro Leu
                245                 250                 255

Ser Ser Phe Arg Asn Arg Asn Leu Ser Val Ala Ser Val Val Gly Leu
                260                 265                 270

Phe Ala Gly Ala Ala Pro Tyr Ala Met Phe Phe Leu Leu Ser Leu His
                275                 280                 285

Leu Gln Asn Val Val Gly Leu Thr Pro Leu Gln Thr Gly Leu Gly Phe
                290                 295                 300

Leu Pro Val Ser Leu Ile Ser Met Val Gly Ala Ala Leu Ala Pro
305                 310                 315                 320

Leu Ala Met Ala Arg Ile Gly Met Arg Phe Thr Leu Leu Ser Leu
                325                 330                 335

Gly Val Leu Ala Val Gly Leu Val Leu Ser Arg Leu Thr Glu Glu
                340                 345                 350

Asp Gly Phe Gly Ala Thr Val Ala Gly Gln Leu Val Ala Gly Leu Gly
                355                 360                 365

Leu Gly Thr Thr Phe Val Ala Val Thr Thr Ala Ala Val Ala Gly Leu
370                 375                 380

Ala Glu Asn Glu Ser Gly Leu Ala Ser Gly Leu Ile Asn Thr Ala Gln
385                 390                 395                 400

Gln Leu Gly Gly Ala Leu Gly Leu Gly Ala Leu Ala Ala Leu Ser Gly
                405                 410                 415

Ala Tyr Ser Ala Ala Glu Leu Ala Lys Glu Pro Pro Val Ser Glu Val
                420                 425                 430

Ala Ala Leu Ser Ser Gly Tyr Gln Val Ala Phe Leu Gly Ala Ala Val
                435                 440                 445

Phe Ala Val Ala Gly Ala Leu Ile Ala Leu Ala Leu Pro Arg Arg Glu
                450                 455                 460

Ser Val Pro Ala Thr Thr Pro His Glu
465                 470

<210> SEQ ID NO 19
<211> LENGTH: 81
<212> TYPE: PRT

```
<213> ORGANISM: ARTIFICIAL
<220> FEATURE:
<223> OTHER INFORMATION: OrfD12

<400> SEQUENCE: 19

Met Ala Ala Glu Pro Asp Ala Arg Pro Leu Asp Gly Pro Ala Gly Gly
1               5                   10                  15

Asp Ala Gly Leu Pro Tyr Leu Ile Ala Arg Val Glu His Ala Ile Ala
            20                  25                  30

Gly Arg Ala Asn Leu Ala Leu Gly Ala Leu Gly Leu Thr Ile Arg Gln
        35                  40                  45

Met Gly Ala Leu Asp Ile Val Ser Arg Asn Pro Gly Ile Ser Ser Val
    50                  55                  60

Glu Leu Ala Arg Gln Val Leu Val Thr Arg Gln Thr Met Asn Ser Met
65              70                  75                  80

Ile

<210> SEQ ID NO 20
<211> LENGTH: 23
<212> TYPE: DNA
<213> ORGANISM: ARTIFICIAL
<220> FEATURE:
<223> OTHER INFORMATION: Sythetic oligonucleotide CS003

<400> SEQUENCE: 20
tagaattcat cgaacccgcg gcc                                    23

<210> SEQ ID NO 21
<211> LENGTH: 24
<212> TYPE: DNA
<213> ORGANISM: ARTIFICIAL
<220> FEATURE:
<223> OTHER INFORMATION: Synthetic oligonucleotide CS004

<400> SEQUENCE: 21
tataagcttc ggctgccagc gctc                                   24
```

The invention claimed is:

1. A method for producing indolocarbazoles comprising the following steps:
   (a) isolating from the genome of an indolocarbazole producing organism a DNA molecule comprising the polynucleotide as set forth in SEQ ID NO: 1 or a fragment of SEQ ID NO: 1 encoding the polypeptide as set forth in SEQ ID NO: 11;
   (b) inserting said DNA molecule into a recombinant vector suitable for host cells;
   (c) introducing said recombinant vector into host cells, in a way that it can be stably maintained; and
   (d) culturing the host cells with the recombinant vector in a culture medium suitable for indolocarbazole production.

2. An isolated nucleic acid molecule comprising the polynucleotide as set forth in SEQ ID NO: 1 or a fragment of SEQ ID NO: 1 encoding the polypeptide as set forth in SEQ ID NO: 11.

3. The isolated nucleic acid molecule according to claim 2, comprising the polynucleotide as set forth in SEQ ID NO: 1.

4. The isolated nucleic acid molecule according to claim 2, comprising the polynucleotide encoding the polypeptide as set forth in SEQ ID NO: 11.

5. A vector comprising the nucleic acid molecule as defined in claim 4.

6. An isolated host cell or transgenic microorganism comprising the nucleic acid molecule as defined in claim 4.

7. An isolated host cell or transgenic microorganism comprising the vector as defined in claim 5.

8. The host cell according to claim 6, consisting of a strain of *Streptomyces* spp., its mutants, or its transformed derivatives.

9. The host cell according to claim 8, consisting of a strain of *Streptomyces albus*, its mutants, or its transformed derivatives.

10. The host cell according to claim 6, expressing resistance to rebeccamycin.

11. The host cell according claim 6, expressing resistance to an indolocarbazole.

12. A method for producing indolocarbazoles, indolocarbazole derivatives, or indolocarbazole precursors comprising culturing the host cell of claim 6.

13. A method for producing rebeccamycin, rebeccamycin derivatives, or rebeccamycin precursors comprising culturing the host cell of claim 6.

14. A method for increasing the production of indolocarbazoles comprising culturing the host cell of claim 6.

15. A method for obtaining host cells expressing resistance to an indolocarbazole comprising culturing the host cell of claim 6.

16. A method for the isolation and/or utilization of indolocarbazole biosynthetic genes comprising performing a polymerase chain reaction (PCR) using the nucleic acid molecule as defined in claim 2.

17. A method for producing indolocarbazoles, indolocarbazole derivatives, or indolocarbazole precursors comprising culturing the host cell of claim 6.

18. A method for producing rebeccamycin, rebeccamycin derivatives, or rebeccamycin precursors comprising culturing the host cell or transgenic microorganism of claim 6.

19. A method for production of indolocarbazoles comprising the following steps:
  (a) isolating from the genome of an indolocarbazole producing organism a DNA molecule comprising the polynucleotide as set forth in SEQ ID NO: 1 or a fragment thereof encoding the polypeptide as set forth in SEQ ID NO: 11;
  (b) inserting said DNA molecule into a recombinant vector suitable for a *Streptomyces* host cell;
  (c) introducing said recombinant vector into the *Streptomyces* host cell in a way that it can be stably maintained; and
  (d) culturing the *Streptomyces* host cell with the recombinant vector in a culture medium suitable for indolocarbazole production.

20. The method according to claim 19, wherein the host cell is a strain of *Streptomyces albus*.

21. The method according to claim 19, wherein the DNA molecule isolated in step (a) comprises the polynucleotide encoding the polypeptide as set forth in SEQ ID NO: 11.

22. The method according to claim 19, wherein the DNA molecule isolated in step (a) comprises the polynucleotide as set forth in SEQ ID NO: 1.

23. A vector comprising the nucleic acid molecule defined in claim 3.

24. An isolated host cell or transgenic microorganism comprising the nucleic acid molecule defined in claim 3.

25. An isolated host cell consisting of a strain of *Streptomyces* comprising the vector of claim 23.

26. The host cell according to claim 25 which is a strain of *Streptomyces albus*.

27. The isolated nucleic acid molecule according to claim 2 that consists of the polynucleotide encoding the polypeptide as set forth in SEQ ID NO: 11.

28. The isolated nucleic acid molecule according to claim 2 that consists of the polynucleotide as set forth in SEQ ID NO: 1.

29. The method according to claim 1, wherein the DNA molecule isolated in step (a) consists of the polynucleotide encoding the polypeptide as set forth in SEQ ID NO: 11.

30. The method according to claim 1, wherein the DNA molecule isolated in step (a) consists of the polynucleotide as set forth in SEQ ID NO: 1.

* * * * *